United States Patent
Mason et al.

(10) Patent No.: US 12,065,700 B2
(45) Date of Patent: Aug. 20, 2024

(54) SINGLE SPERM GENE EXPRESSION AND MUTATION ANALYSIS FOR PREDICTION OF DISEASES

(71) Applicants: CORNELL UNIVERSITY, Ithaca, NY (US); RUTGERS, THE STATE UNIVERSITY OF NEW JERSEY, New Brunswick, NJ (US)

(72) Inventors: Christopher E. Mason, Ithaca, NY (US); Jeffrey Rosenfeld, Bergenfield, NJ (US); Delia Tomoiaga, Ithaca, NY (US)

(73) Assignees: CORNELL UNIVERSITY, Ithaca, NY (US); Rutgers, The State University of New Jersey, New Brunswick, NJ (US)

( * ) Notice: Subject to any disclaimer, the term of this patent is extended or adjusted under 35 U.S.C. 154(b) by 280 days.

(21) Appl. No.: 16/486,611

(22) PCT Filed: Feb. 17, 2018

(86) PCT No.: PCT/US2018/018534
§ 371 (c)(1),
(2) Date: Aug. 16, 2019

(87) PCT Pub. No.: WO2018/152432
PCT Pub. Date: Aug. 23, 2018

(65) Prior Publication Data
US 2020/0010896 A1   Jan. 9, 2020

Related U.S. Application Data

(60) Provisional application No. 62/460,408, filed on Feb. 17, 2017.

(51) Int. Cl.
| | |
|---|---|
| *C12Q 1/68* | (2018.01) |
| *C12Q 1/6827* | (2018.01) |
| *C12Q 1/6883* | (2018.01) |
| *G16B 20/20* | (2019.01) |
| *G16B 30/20* | (2019.01) |
| *G16H 50/30* | (2018.01) |

(52) U.S. Cl.
CPC ......... *C12Q 1/6883* (2013.01); *C12Q 1/6827* (2013.01); *G16B 20/20* (2019.02); *G16B 30/20* (2019.02); *G16H 50/30* (2018.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2010/0298154 A1 | 11/2010 | Simmet et al. |
| 2013/0288993 A1 | 10/2013 | Walsh et al. |
| 2014/0194300 A1* | 7/2014 | Song et al. .......... C12Q 1/6869 |

OTHER PUBLICATIONS

Milekic et al. Age-related sperm DNA methylation changes are transmitted to offspring and associate with abnormal behavior and dysregulated gene expression (2015) Molecular Psychiatry 20, 995-1001. (Year: 2015).*
Haque et al. A practical guide to single-cell RNA-sequencing for biomedical research and clinical applications (2017) Genome Medicine 9:75. 12 pages. (Year: 2017).*
Gandal et al. Transcriptome-wide isoform-level dysregulation in ASD, schizophrenia, and bipolar disorder (2018) Science 362:1265, 12 pages. (Year: 2018).*
Spiess et al Journal fur Reproduktionsmedizin und Endokrinologie, (2017) vol. 14, No. 5, pp. 239. Abstract No. p. 42. Meeting Info: 7. DVR-Kongress 2017. Munchen, Germany. Dec. 7, 2017-Dec. 9, 2017 ISSN: 1810-9292 (Year: 2017).*
Yu et al. (Biology of Reproduction, 2017, 97(3), 490-496; (Year: 2017).*
Zheng et al. (Nature Communications, 8, 14049, doi: 10.1038/ncomms14049 (2017), 12 pages; (Year: 2017).*
Kimoto (Mol. Gen. Genet (1998) 258:233-239) (Year: 1998).*
Milekic et al. Molecular Psychiatry (2015) 20, 995-1001 (Year: 2015).*
Akers "Does Older Sperm Cause Autism?" Healthline.com (2017) (Year: 2017).*
Extended Supplementary European Search Report dated Oct. 29, 2020 in European Patent Application No. 18 75 4777.3.
Chen, J. et al., Single-cell SNP analyses and interpretations based on RNA-Seq data for colon cancer research, Scientific Reports, vol. 6, No. 1, pp. 1-14 (Sep. 28, 2016).
Katz-Jaffe, M.G. et al., "Aging sperm negatively impacts in vivo and in vitro reproduction: a longitudinal murine study", Fertility and Sterility, vol. 100, No. 1, pp. 262-268 (Jul. 1, 2013).
Mao, S. et al., A comparison of sperm RNA-seq methods, Systems Biology in Reproductive Medicine, vol. 60, No. 5, pp. 308-315 (Jul. 31, 2014).
Sharma, R. et al., Effects of increased paternal age on sperm quality, reproductive outcome and associated epigenetic risks to offspring, Reproductive Biology and Endocrinology,vol. 13: 35, pp. 1-20 (Apr. 9, 2015).
Spiess, A.N. et al., "Gene expression analysis of single human spermatozoa: approaches and caveats", J Reproduktions Med Endokrinol_Online 2017, vol. 14, No. 5, p. 239 (2017).
Tomoiaga, D. et al., Single-cell sperm transcriptomes and variants from fathers of children with and without autism spectrum disorder, NPJ Genomic Medicine, vol. 5, No. 1, pp. 1-7 (Feb. 21, 2020).
Yu, T. et al., "Microfluidics-based digital quantitative PCR for single-cell small RNA quantification+", Biology of Reproduction, vol. 97, No. 3, pp. 490-496 (Aug. 31, 2017).

(Continued)

*Primary Examiner* — Juliet C Switzer
(74) *Attorney, Agent, or Firm* — Scully, Scott, Murphy & Presser, P.C.

(57) ABSTRACT

The present disclosure is directed to methods for typing and characterizing sperm. The technology employs a sequencing-based method for detecting and measuring RNA transcripts from single sperm cells and the analysis of the sequencing data for the prediction of male parent contribution to autism.

21 Claims, 12 Drawing Sheets
(11 of 12 Drawing Sheet(s) Filed in Color)

(56) References Cited

OTHER PUBLICATIONS

Zheng, G. X.Y. et al., "Massively parallel digital transcriptional profiling of single cells", Nature Communications, 8(1), 1-12 (2017).
Wilkinson, B. et al., "Contribution of Long Noncoding RNAs to Autism Spectrum Disorder Risk", International Review of Neurobiology, vol. 113, pp. 35-59, Academic Press (2013).
International Search Report dated Jun. 22, 2018 issued in International Application No. PCT/US18/18534.
Written Opinion of the International Searching Authority from International Application No. PCT/US18/18534 dated Jun. 22, 2018.
Aitken R.J. et al., "The Sins of Our Forefathers: Paternal Impacts on De Novo Mutation Rate and Development", Annual Reviews of Genetics 54:1-24 (2020).
Janecka M. et al., "Advanced Paternal Age Effects in Neurodevelopmental Disorders—Review of Potential Underlying Mechanisms", Translational Psychiatry 7:e1019 (2017).
Krug A. et al., "Advanced Paternal Age as a Risk Factor for Neurodevelopmental Disorders: A Translational Study", Molecular Autism 11:54 (2020).
Vervoort I. et al., "A Multifactorial Model for the Etiology of Neuropsychiatric Disorders: The Role of Advanced Paternal Age", Pediatric Research doi: 10.1038/s41390-021-01435-4 (Mar. 5, 2021).

* cited by examiner

A

| Name | Sample Type | Est. No. of Cells | Mean Reads per Cell | Median Genes per Cell |
|---|---|---|---|---|
| num1 | PBMC/control | 5,671 | 7,725 | 253 |
| num3 | ASD | 24,095 | 7,281 | 9 |
| num4 | Normal | 11,245 | 2,452 | 9 |
| num5 | Normal | 5,869 | 61,489 | 82 |
| num6 | Normal | 51,419 | 7,299 | 28 |
| num7 | Normal | 50,569 | 5,943 | 28 |
| num8 | Normal | 36,639 | 6,422 | 32 |
| num9 | ASD | 65,404 | 4,164 | 25 |
| num10 | ASD | 2,747 | 87,366 | 92 |

B

| Sample ID | Donors | Single Cell 3' Reagent and library kit version | Cell Ranger version | Estimated Number of Cells from Cell Ranger | Mean Reads per Cell | Median Genes per Cell | Number of Reads |
|---|---|---|---|---|---|---|---|
| 5 | Normal | 2 | 1.2 | 5,869 | 61,489 | 82 | 360,882,628 |
| 6 | Normal | 2 | 1.2 | 51,419 | 7,299 | 28 | 375,345,710 |
| 7 | Normal | 2 | 1.2 | 50,569 | 5,943 | 28 | 300,552,645 |
| 8 | Normal | 2 | 1.2 | 41,638 | 8,158 | 37 | 339,682,902 |
| 9 | Autistic | 2 | 1.2 | 65,364 | 4,972 | 28 | 325,033,861 |
| 10 | Autistic | 2 | 1.2 | 2,661 | 115,854 | 112 | 308,289,121 |

FIG. 4A – 4B

SINGLE SPERM GENE EXPRESSION AND MUTATION ANALYSIS FOR PREDICTION OF DISEASES

CROSS REFERENCE TO RELATED APPLICATION

This application claims the benefit of priority from U.S. Provisional Application No. 62/460,408, filed Feb. 17, 2017, the entire contents of which are incorporated herein by reference.

BACKGROUND

While the human egg is one of the largest cells in the human body, sperm is the smallest human cell. The average male produces tens of millions of sperms per day and even a male with low sperm count has over a million sperms per mL of semen. The need for this large number of sperm to achieve fertilization is not clearly understood, but may be related to chemical conditions in the uterus and female anatomy (Reynaud K. et al, Communicative & Integrative Biology, 2015. 8(3): p. e1017156). An additional reason for the large number of sperm may be their high mutation rate (Rahbari R. et al., Nat Genet, 2016. 48(2): p. 126-133) and the need for a sperm with normal genotypes to successfully fertilize an egg and produce a viable offspring.

The human sperm is one of the most important cells since they serve as the entire paternal genetic contribution to a child. For any disease that the child inherits form the father the mutation must be contained in the sperm. This is especially important for a disease such as autism, which has been correlated with advance paternal age. Up until now, most studies of sperm have focused on the assessment of a bulk sperm sample. This bulk sample would contain millions of individual sperm and only variants that show up in a large percentage of the cells would be detected.

There are many health problems that are related to an increase in paternal age. Psychological and genetic explanations have been offered for this observation (de Kluvier, H. et al., American Journal of Medical Genetics Part B: Neuropsychiatric Genetics, 2016). A father who has a psychological illness that leads him to delay marriage and procreation will by definition have children at an older age. Alternatively, there could be an accumulation of mutation in a male's testes as he ages and these mutations will be present in the sperm that produce his children. The older a father is, the more mutations he will have. Multiple studies (Kong, A. et al., Nature, 2012. 488(7412): p. 471-475, Francioli L. C. et al, Nature Genetics, 2015. 47(7): p. 822-826) have found that the number of de novo mutations in offspring increase roughly linearly as the fathers' age increases. The results vary by study but there is approximately one additional de novo mutation added to the genome of a child per year of the father's age. These mutations are distributed throughout the genome (Acuna-Hildago R. et al. Genome Biology, 2016. 17(1): p. 241) though there is some evidence of mutational hotspots (Michaelson, J. J. et al., Cell, 2012. 151(7): p. 1431-1442). Since the vast majority of the genome is not responsible for coding genes or gene regulation, most paternal de novo mutations will not result in a phenotype in the offspring.

Researchers have previously attempted to detect these mutations in sperm, but they have been limited by the investigation of bulk sperm samples. A bulk sperm sample contains millions of cells and the mutations that are responsible for the diseases in the offspring are only found in a fraction of the sperm (Gorieli A. et al., Science, 2003. 301(5633): p. 643-646). Using current Illumina sequencing techniques, variations present in less than 5% of the bulk sperm samples cannot be reliably detected because of the error rates of the sequencer (Fox E. J. et al., Next Gen. Seq. & App., 2014. 1: p. 1000106). In bulk sample sequencing, when a sequence variation occurs in a small sample of the reads, it is not possible to determine whether this variation is due to heterogeneity in the sample or the random errors of the sequencing chemistry and detection.

There is mounting recent evidence that the spermatozoa have a role in the regulation of early embryonic development by way of delivering functional RNAs to the oocyte during fertilization (Jodar, M. et al., Human Reproduction Update 19(6), 2013, pp. 604-624.; Krawetz, S. A., Nature Reviews Genetics. 2005 6(8), pp. 633-642; Krawetz et al., Human Reproduction, 2011, 26(12), pp. 3401-3412).

SUMMARY OF THE DISCLOSURE

Herein disclosed are systems and methods for typing and characterizing sperm and sperm donors. The technology employs a sequencing-based method for detecting and measuring RNA transcripts from single sperm cells, using reverse transcribed cDNA, and the analysis of the sequencing data for the prediction of autism risk in the offspring. The methods of the present disclosure can apply not only to human sperm, but to any other animal's sperm with RNA present.

The inventors herein performed single-cell RNA sequencing of six sperm samples obtained from a sperm bank on the 10X Genomics Chromium platform (FIG. 1A) to exploring putative differential transcriptome expression between spermatozoa from 4 donors who have had healthy offspring (Normal) versus 2 donors who have had autistic children (Autistic).

BRIEF DESCRIPTION OF THE DRAWINGS

The patent or application file contains at least one drawing executed in color. Copies of this paper or patent application publication with color drawing(s) will be provided by the Office upon request and payment of the necessary fee.

FIG. 4A-4B. Sample sperm sequencing data. (A) for sample 1, 3-10; and (B) for samples 5-10. Samples number 3, 9 and 10 are sperm samples from fathers with at least 2 autistic children. Other samples are control (1) or normal (4-10) samples.

DETAILED DESCRIPTION

Figure 1:
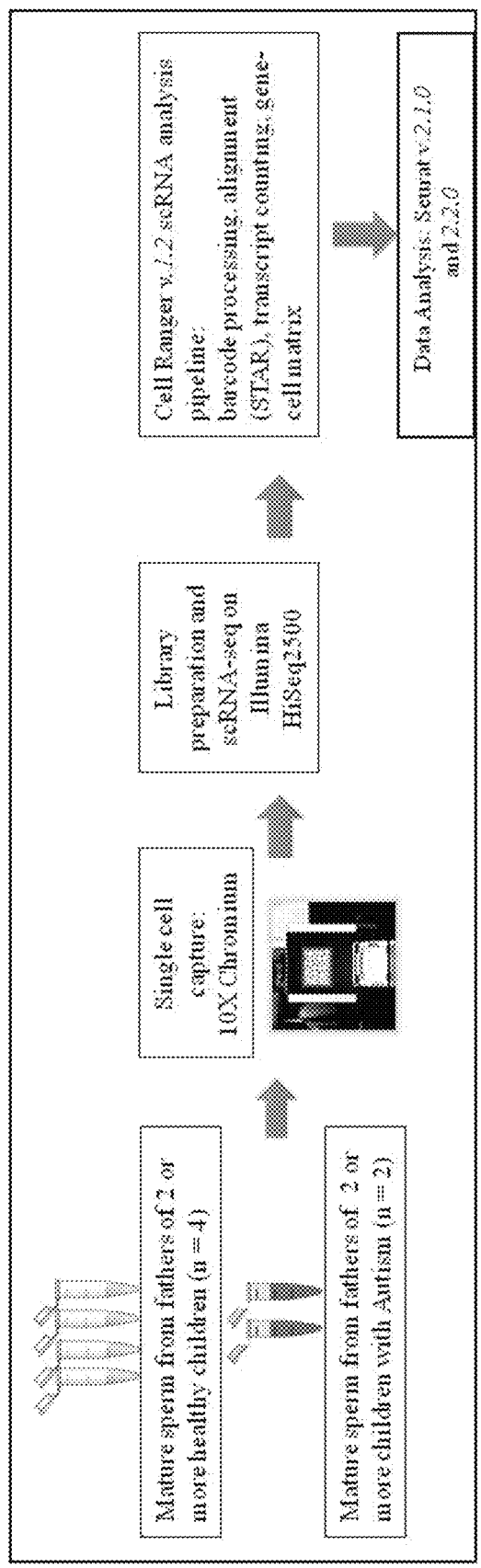
FIG. 1. Schematic of the experimental design. Single-cell RNAseq experimental setup. Mature, motile human sperm fraction from two cohorts, i.e., males who fathered 2 or more children with Autism (Autism) and males who fathered 2 or more healthy, non-Autistic children (Normal), was loaded onto a Chromium by 10X Genomics single-cell capture unit, then the library was prepped and sequenced. The CellRanger pipeline was used to calculate the expression matrix. Downstream data analysis, including log and batch normalization and sample alignment and integration was performed with Seurat in R open source software.
Figures 2A, 2B:
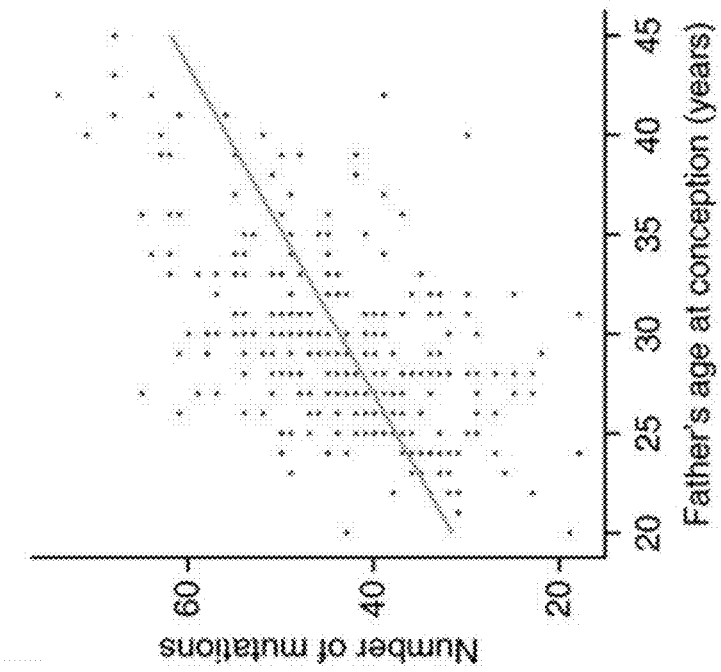
FIGS. 2A-2B. Risk of inherited diseases associated with Paternal Age Effect. (A) The number of mutations in sperm cells increases as father's age at conception increases. (B) Effect of paternal age on several disorders. The offspring's risk of disease increases with older father at the time of conception.
Figure 3:
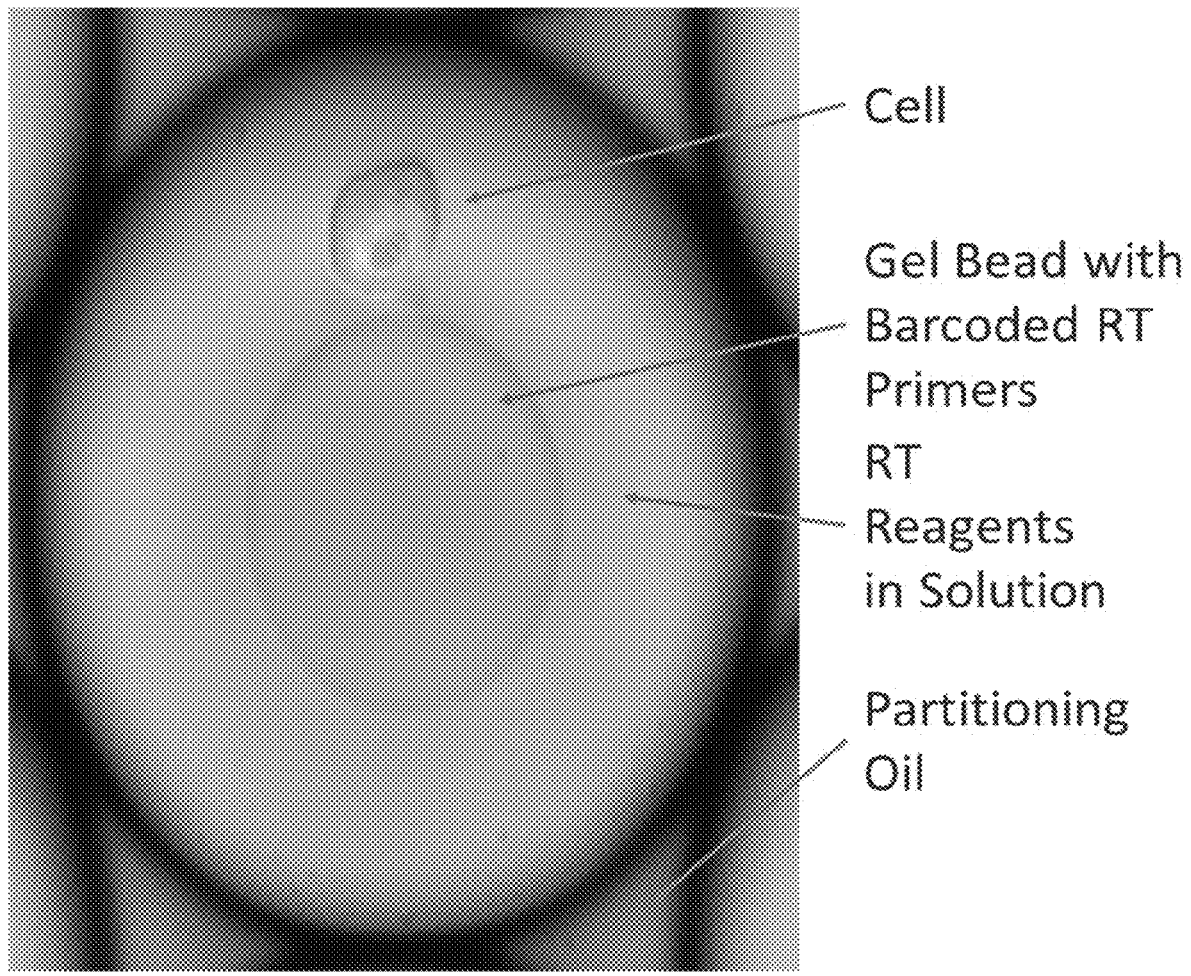
FIG. 3. Single Cell Partitioning in GEMs.
Figures 5A, 5B:
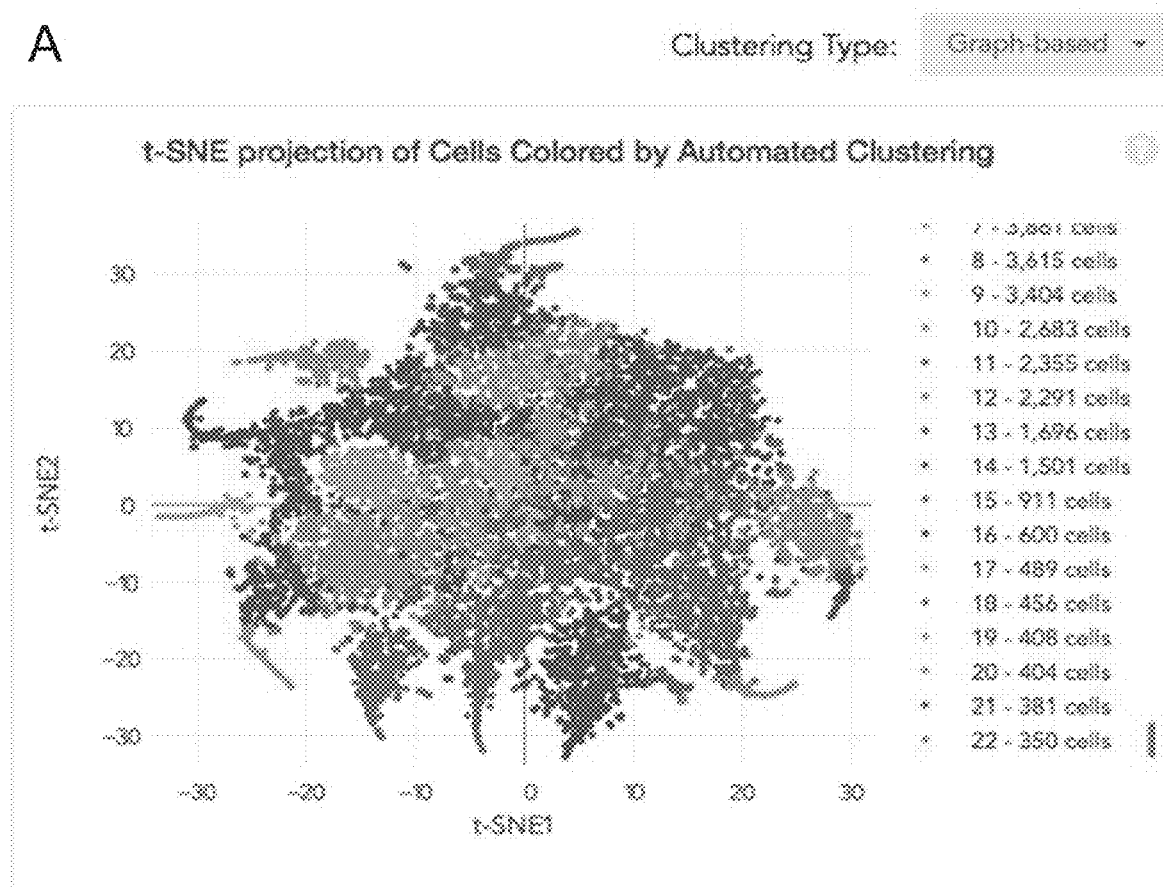
FIGS. 5A-5H. t-distributed stochastic neighbor embedding (t-SNE) analysis of cells in a single sample. (A) t-SNE projection of cells colored by automatic clustering. (B) Number of clusters identified in different samples. (C) t-SNE projection of single-cells, showing 42 individual clusters. (D) t-SNE analysis of single-cells in the batch-corrected and integrated 4 Normal samples. (E) Heat map of top cluster markers for each cluster. Each rectangle represents the normalized scaled average expression values of the single cells in the sample for the specific gene. (F) t-SNE projection of single-cells, showing 43 individual clusters. (G) t-distributed stochastic neighbor embedding (t-SNE) analysis of single-cells in the batch-corrected and integrated 2 Autistic samples. (H) Heat map of top cluster markers for each cluster. Each rectangle represents the normalized scaled average expression values of the single cells in the sample for the specific gene.
Figure 5C:
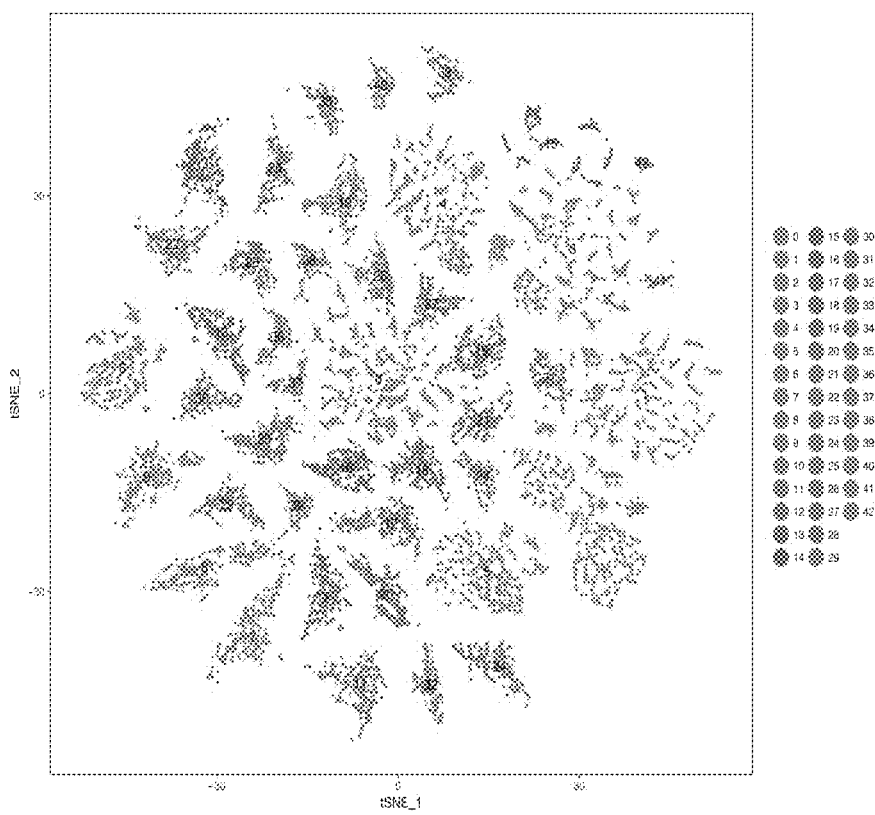
Figure 5D:
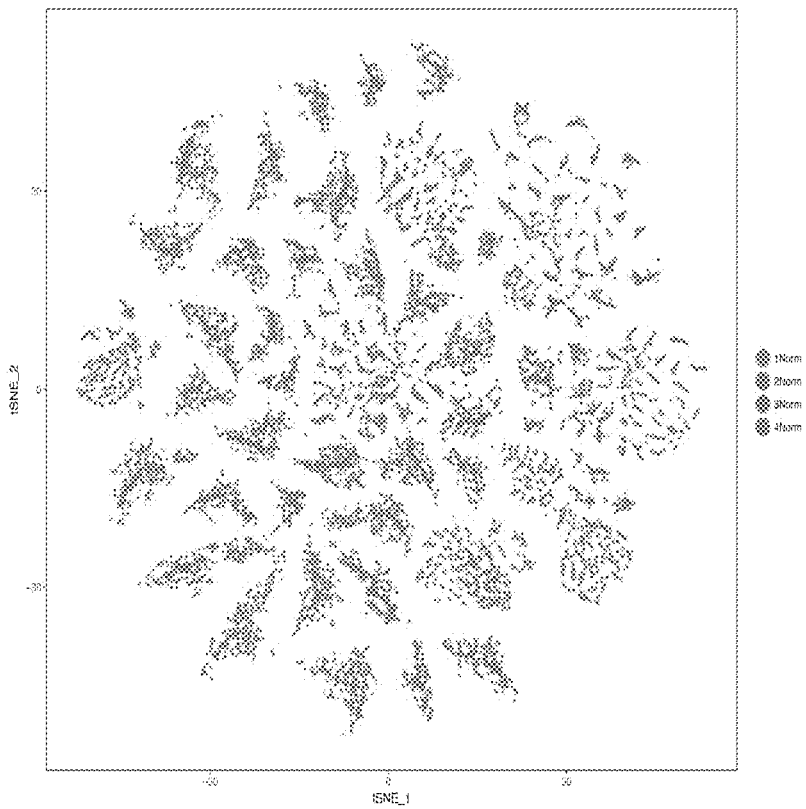
Figure 5E:
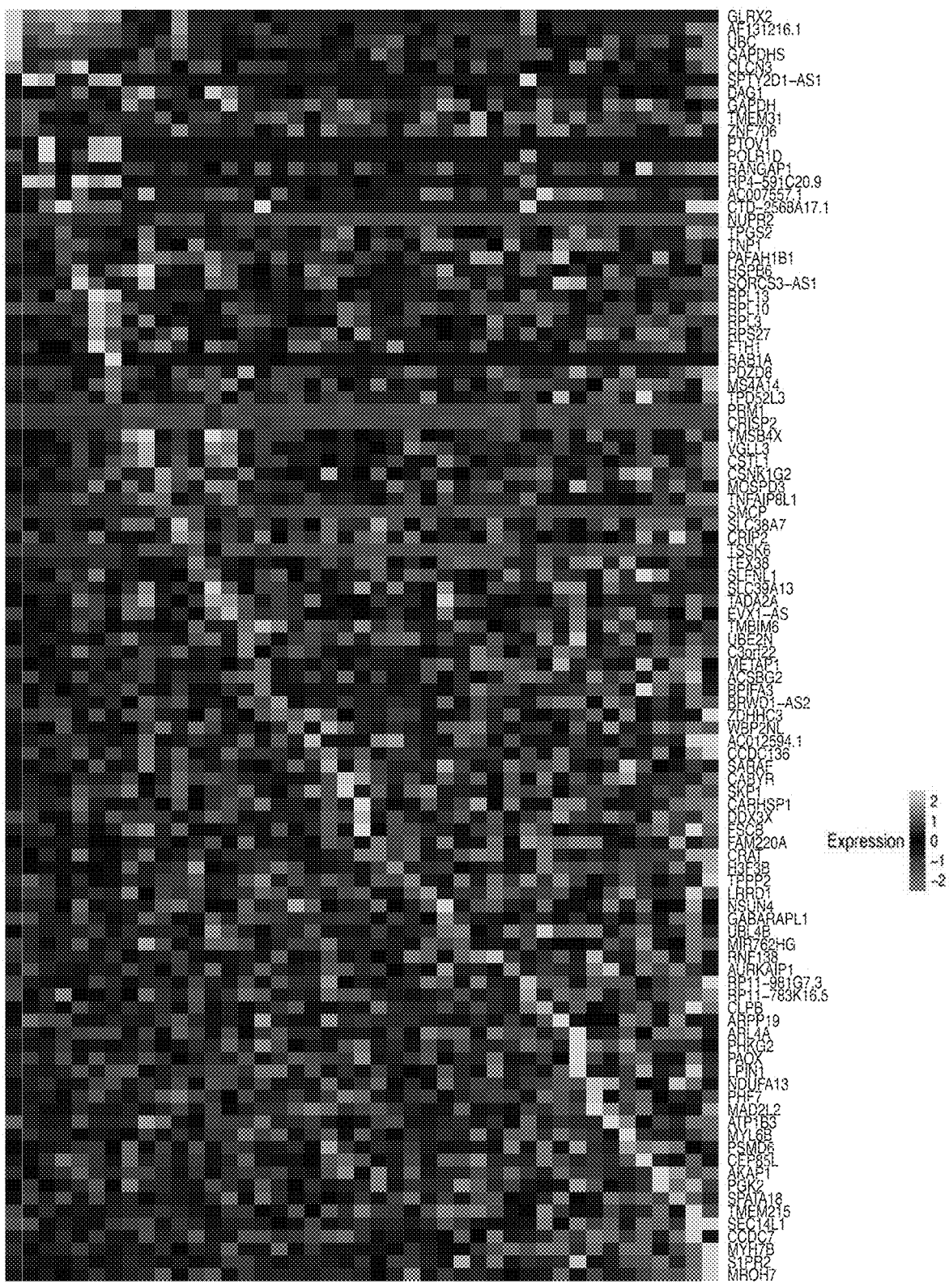
Figures 5F, 5G:
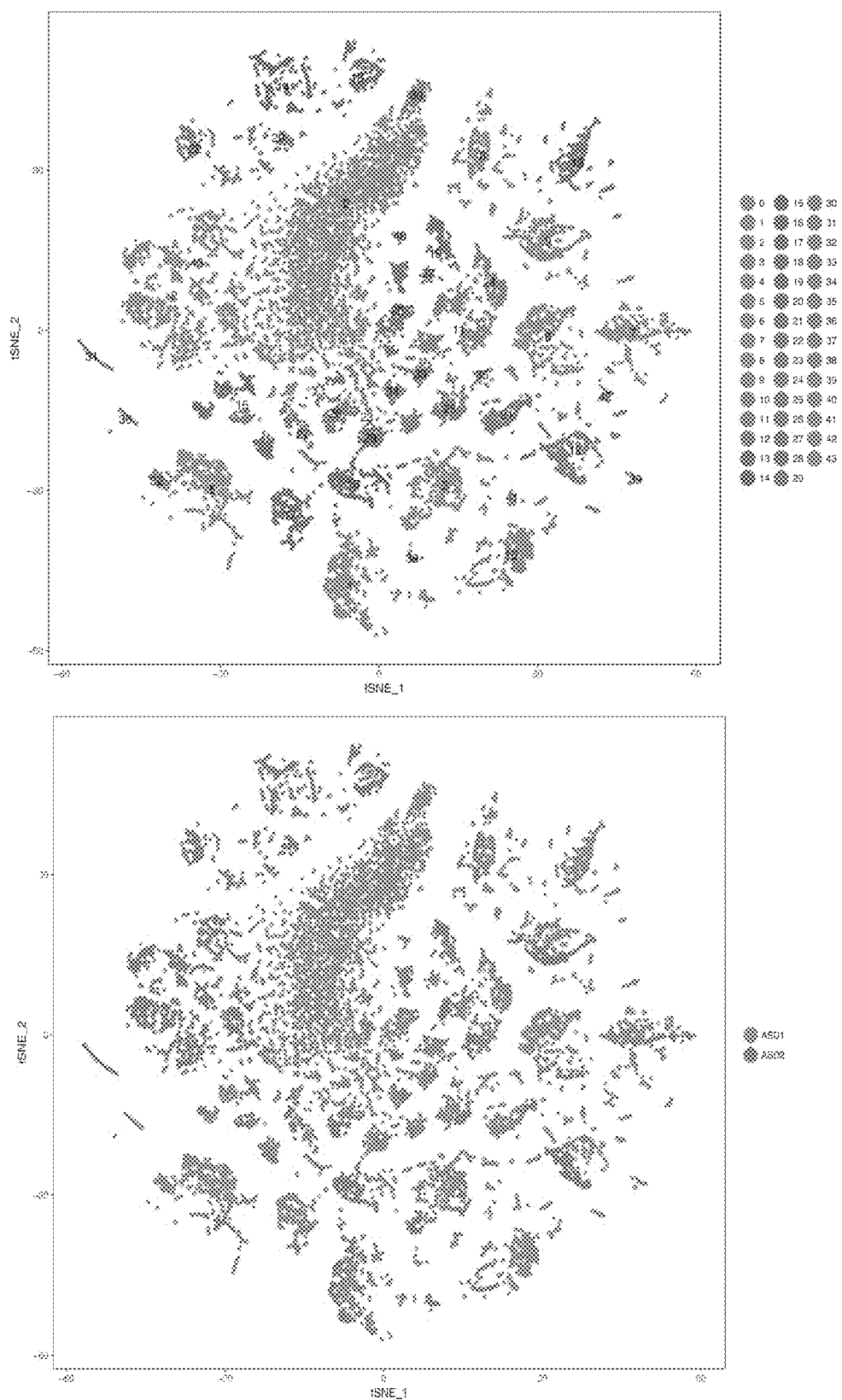
Figure 5H:
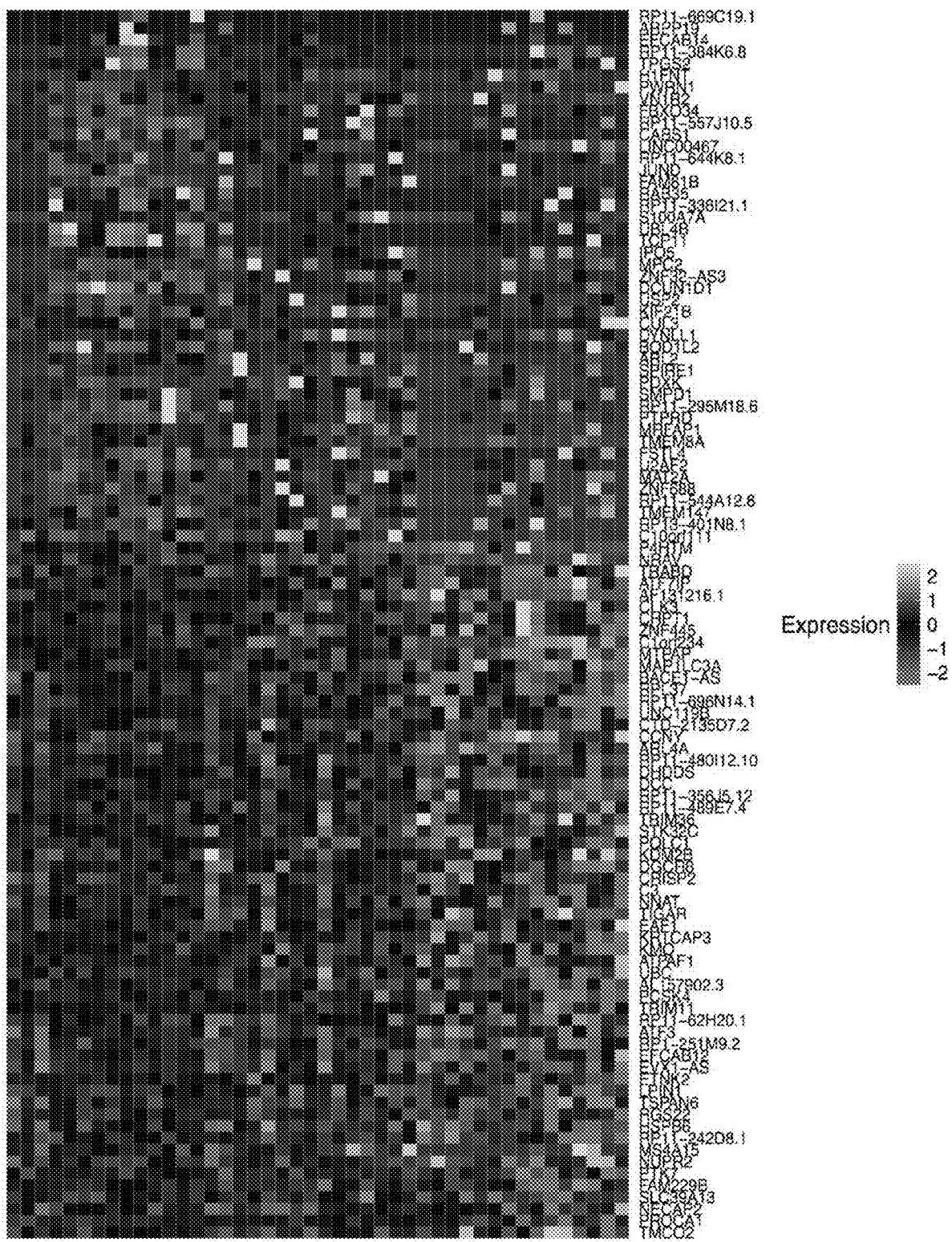
Figure 6A:
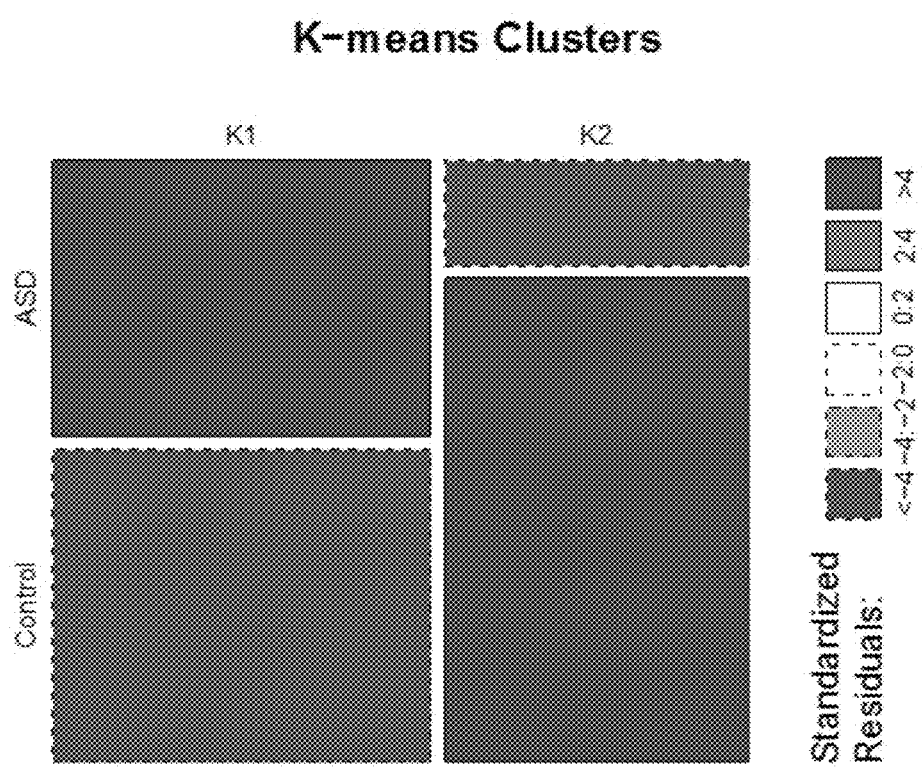
FIG. 6. Differential expression of genes in Autism vs. Normal Control Group. Sperm samples were obtained from sperm banks and separated into two cohorts: sperm samples from fathers of at least 2 children with Autism (Autism) vs. sperm samples from fathers of at least 2 children without Autism (Normal). Top differentially expressed genes between the two cohorts, increased in the Autism group, and that are also expressed in more than 5% of the cells in at least one group, are BACE1-AS, UNC119B, RP11-338I21.1. Top differentially expressed genes between the two cohorts, decreased in Autism group, and that are also expressed in more than 5% of the cells in at least one group, are AKAP1, VRK2, CRISP2. PRM1 gene shows increased expression in the Autistic samples while PRM2 transcript shows decreased expression in the Autistic samples.
Figure 6B:
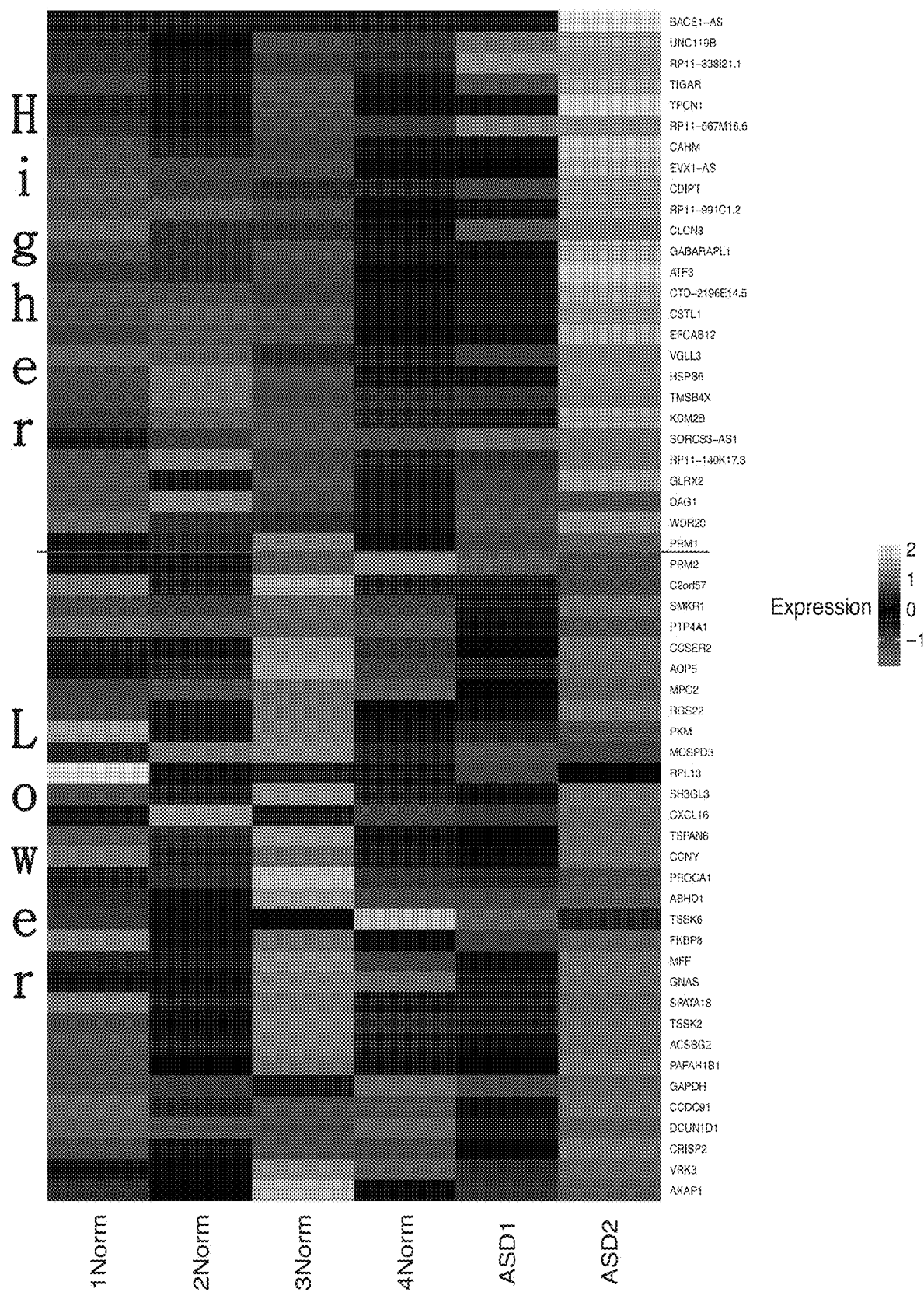
Figure 7:
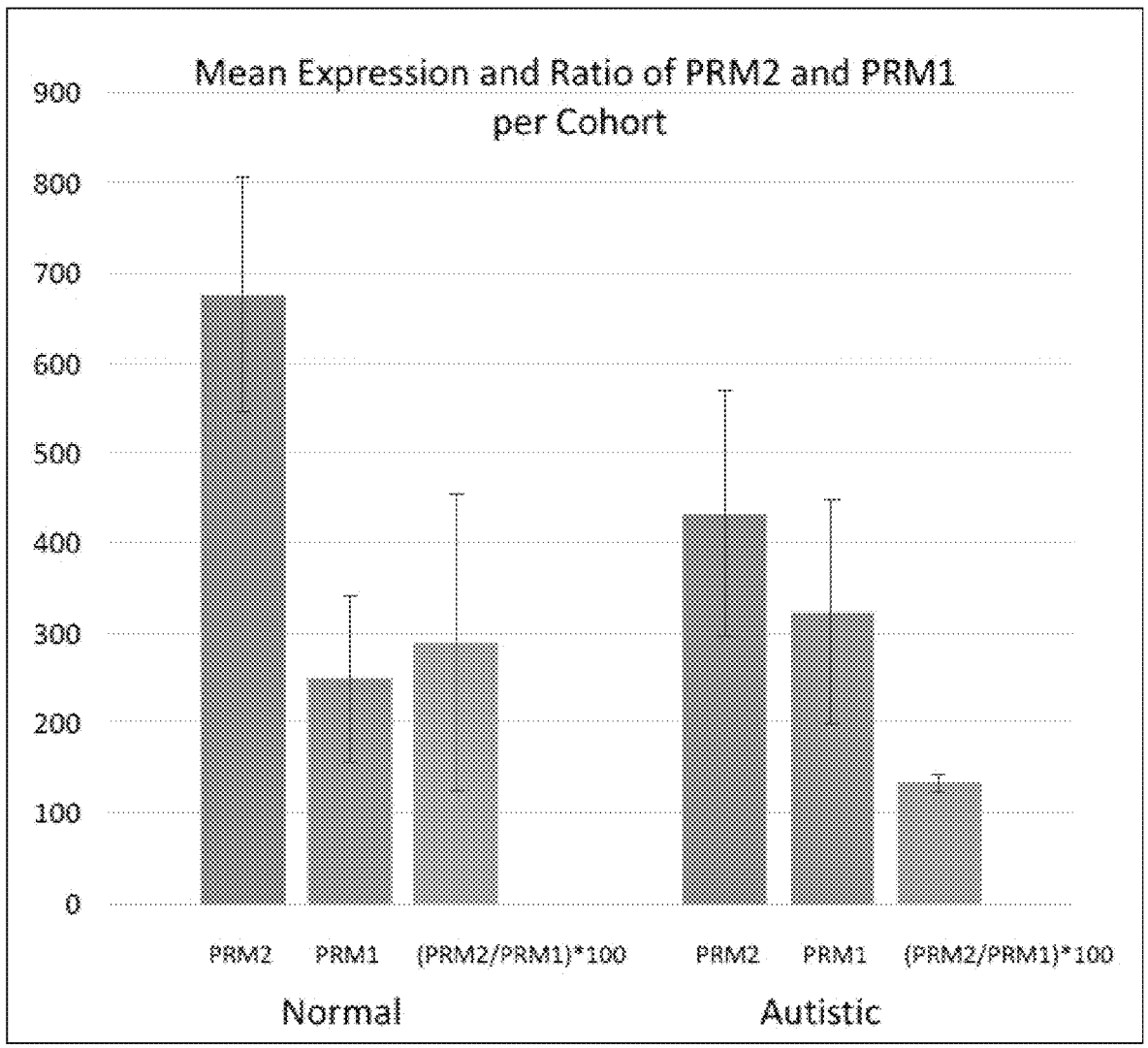
FIG. 7. The average expression levels for PRM2 and PRM1 genes, and PRM2/PRM1 ratios between Autistic and Normal cohorts. In the Normal samples, average normalized scaled expression of PRM2 is 676+/−130, of PRM1 248+/−135, while in the Autistic Samples, PRM2 average is 433+/−125 and of PRM1 is 324+/−164. The ratio of PRM2 to PRM1 in Normal samples is 2.89+/−0.92 and for the Autistic samples, it is lower, at 1.33+/−0.09. The error bars are based on a 95% confidence interval. The average ratio of PRM2 to PRM1 in Normal samples can be as much as 3.5 times higher than in Autistic samples and that these three features (individual protamine expression and their ratio) are useful markers for assessing risk of Autism in progeny from sperm.

The term "control autistic sperm" refers to a sperm sample from a father having at least two autistic children. The term "control healthy sperm" defines a sperm sample from a father having no autistic children.

The term "gene expression" refers to the process by which a nucleic acid sequence undergoes successful transcription and in most instances translation to produce a protein or peptide. For clarity, when reference is made to measurement of "gene expression", this should be understood to mean that measurements may be of the nucleic acid product of transcription, e.g., RNA or mRNA or of the amino acid product of translation, e.g., polypeptides or peptides. Methods of measuring the amount or levels of RNA, mRNA, polypeptides and peptides are well known in the art.

The terms "gene expression profile" or "GEP" refer to the presence, absence and/or levels of expression of a large number of genes, often hundreds or thousands of genes, expressed by a particular cell or tissue type. The gene expression profile of a cell or tissue presents a global picture of cellular function and can serve as a fingerprint or pattern that distinguishes the cell or tissue from other cells or tissues.

As used herein, the term "risk" refers to the probability that an event will occur.

The term "Unique molecular identifiers (UMIs)" refers to short sequences or "barcodes" added to each read in some next generation sequencing protocols. They serve to reduce the quantitative bias introduced by replication, which is necessary to get enough reads for detection (see, Kivioja T. et al., Nat. Methods. 9 (1): 72-4). UMIs are especially useful for single cell RNA-Seq (see, Islam S. et al., Nat. Methods. 11 (2): 163-6).

This disclosure provides methods of generating a gene expression profile of a single sperm cell. The disclosed method utilizes RNA transcripts from single sperm cells in generating gene expression profiles. The present method has several advantages over other methods: Haploid cells only have one copy of each chromosome; it is easy to obtain in large amounts (the average adult male produces millions per day); and the biological contribution is only from the father and contains any mutations that may be passed from the father to the children.

In some embodiments, a gene expression profile is generated by RNA-Seq (RNA sequencing). In some embodiments, a gene expression profile is generated by direct RNA measurement. In some embodiments, a gene expression profile is generated from cDNA (RNA converted in to DNA). In a specific embodiment, the cDNA can be sequenced to generate a gene expression profile.

In some embodiments, generating a gene expression profile of a single sperm comprises constructing a single cell RNA-Seq library, direct RNA measurement library or cDNA library from the sperm.

In some embodiments, an automated cDNA synthesis protocol from the 10X Genomics platform is employed for generating single sperm gene expression profiles. In other embodiments, other suitable automated and droplet-based systems may be used. In a specific embodiment, the method involves isolating individual sperm within an oil-based, membrane-based, or lipid-driven droplet, or placed into a well. In some embodiments, the method further includes, mixing the sample with a reverse transcriptase (RT), a unique molecular index (UMI), and then sequencing the cDNA from the uniquely-labeled cells. These sequence reads are then aligned to the human genome, bar-code corrected, counted, and mapped to all known GENECODE genes.

In some embodiments, generating a gene expression profile from a single sperm comprises isolating a single sperm cell. In some embodiments, single sperm isolation is achieved from agarose films, by FACs or by using Gel Bead Emulsions (As described in Lien, Sigbjorn, et al., Current Protocols in Human Genetics (2002): 1-6; and Zheng et al., Nature Communications, 8. 2017:14049).

In some embodiments, the sperm is a human sperm. In some embodiments, the sperm is a non-human animal sperm (e.g., non-human mammal such as cows, pigs, horses).

In some embodiments, a gene expression profile of a single sperm is further analyzed for mutations. In some embodiments, the mutations comprise Single Nucleotide Polymorphisms (SNPs), insertions, deletions, copy-number variations, or any other genetic alterations.

In some embodiments, generating a gene expression profile of a single sperm cell comprises the steps of (a) isolating a single sperm cell; (b) constructing a single cell RNA-Seq library direct RNA measurement, or cDNA; and (c) generating a gene expression profile of the single sperm cell by RNA-Seq direct RNA measurement, or cDNA.

In some embodiments the method further comprises (d) comparing the gene expression profile in step (c) with a reference gene expression profile in a control healthy sperm, and (e) determining, based on step (d), a risk of paternal age effect disorders in the offspring. In a specific embodiment, the method further comprises (f) deciding whether or not to use the sperm for in vitro fertilization based on the determination in step (e).

In some embodiments, a gene expression profile of a single sperm comprises the expression level(s) of at least one gene, i.e., one or more (e.g., at least 5, 10, 15, 20, 25, 30, 35, 40, 45, 50, 55, 60, 65, 70, 100, 200, 300, 400, 500, 600 or all of the) genes, selected from the group consisting of BACE1-AS, UNC119B, RP11-338I21.1, MEIS1, WDR55, IL6R, RP11-62H20.1, RP11-356J5.12, RP1-251M9.2, DNAJB4, MALSU1, EFCAB14, C3, RAB35, DNAJB7, DYNLL2, TIGAR, SSUH2, TPCN1, AL157902.3, STK32C, MED30, CTD-2083E4.6, LHX2, RP11-567M16.6, PHKB, CAHM, RP11-17A4.2, SIPA1L1, TMEM260, CDC42BPA, EVX1-AS, RP11-242D8.1, CDIPT, RP11-991C1.2, AP006216.5, RP11-696N14.1, TRABD, AC074391.1, CLCN3, RP11-644K8.1, GABA-RAPL1, ATF3, RFPL3S, CTD-2196E14.5, RP11-496I9.1, RP11-347D21.1, TRMT5, RP11-712B9.2, CSTL1, XXbac-BPG249D20.9, RP11-669C19.1, NRDE2, MAPT-AS1, EFCAB12, VGLL3, DCC, HSPB6, S100A7A, CTD-2135D7.2, KRT15, RP11-403A21.3, RP11-396C23.4, C10orf90, GMFG, KDM2B, TMSB4X, RP11-381K20.4, OR2H1, ZNF445, TEPP, CTC-543D15.8, CCDC155, MAPK3, RP5-1030M6.3, SORCS3-AS1, RP11-489E7.4, AC007163.3, XXyac-YX155B6.5, TP53TG5, C9orf3, APOL6, ARL4C, AC093627.10, SERPINB6, PIBF1, CDK19, RBBP6, RP11-140K17.3, EAF1, GLRX2, RP11-557J10.5, DAG1, RP11-96K19.5, WDR20, AC093818.1, NECAP2, RP11-375N15.2, DHDDS, LRRC52, WTIP, TNKS, CFAP157, COX8C, XPNPEP3, NOLC1, RARA-AS1, RP4-625H18.2, FANK1, PPP2R1B, RP11-168K9.1, MIR762HG, RP11-315I20.1, TADA2A, MEST, RP11-480I12.10, TMCO2, ZFP36L1, ATP1B3, CRAMP1, SPTY2D1-AS1, TNP1, AC007557.1, ACAP1, MARCKS, CTD-2568A17.1, PRM1, TCEB2, TMEM31, PHOSPHO1, ETNK2, C17orf74, DGCR6L, ODF3L2, CIB1, NUPR2, C16orf82, UBXN6, DNAJC4, UBA52, REEP6, LELP1, RANGAP1, TNFAIP8L1, ARL4A, PRM2, TPGS2, CSNK1G2, LPIN1, ZNHIT2, PCSK4, PCYT2, OAZ3, TPPP2, SMCP, FBXW5, TCP11, BOD1L2, CARHSP1, GLUL, C2orf57, SMKR1, PTP4A1, CCSER2, AQP5, MPC2, RGS22, PKM, MOSPD3, CCDC136, AC012370.3, VTI1B, INCA1, SPATC1L, CXCL16, METAP1, USP25, SH3GL3, MAP2K2, CRAT, RPS27A, RPL29, RPL13, ANKRD12, TUBB4B, NRAV, FAM220A, FXR1, BSG, TSPAN6, RPL12, PWRN1, SRP54, CCNY, PVRL3, BPIFA3, PTOV1, ADO, NSUN4, SRPK2, RIOK3, SPCS1, GPR137, UBE2N, RPL8, WASF1, FUNDC2, HDLBP, SPTBN2, SLFNL1, GSG1, NT5C1B, PPP2R5A, PHKG2, PROCA1, INPP5K, PDZD8, ABHD1, SLAIN2, SPATA3, TSSK6, UBE2D2, PRC1-AS1, VWA3B, HSPA4L, FKBP8, MFF, LINC00901, GNAS, RNF138, CABYR, TSSK1B, TSSK2, SPATA18, RPS18, SLC38A7, TPD52L3, ACSBG2, RP11-14J7.7, RPLP1, TPP2, PSMD6, PAFAH1B1, UBA5, RPL37A, GAPDH, RPS8, C17orf97, CCDC91, SEC14L1, MTFR1L, DCUN1D1, RAB1A, CRISP2, RPS6, PGK2, VRK3, BAZ1A, TPT1, AKAP1, MS4A14, CCDC7, SEMG1, SARAF, RPL13A, FTH1, CUL3, POLR1D, MT-CO2, FSCB, RPS4X, CLU, RPL3, PLBD2, RPL10, ARL6IP4, AACS, RSRC2, ZCCHC8, CTD-2363C16.1, KLHL12, CEP152, RP11-295M18.6, AC084219.4, HDAC4, DPP3, OVOS2, MAMDC2-AS1, FAM186A, ACSS1, CDIP1, INPP5B, PPP1R12B, RP11-527L4.6, ATP6V1A, EFCAB11, VN1R2, FAM179A, PELP1, STOML2, PCOLCE-AS1, AC004490.1, EVX2, RP11-258F1.1, CDKN1C, RP5-971N18.3, LAPTM4A, RP11-369E15.3, EIF5A2, PTPRD, RNF139-AS1, FAM71F1, CLK3, UGT1A6, C21orf91, DES, IBA57-AS1, HNRNPR, CCDC168, AC013436.6, ZNF32-AS3, LINC01095, MAPKAPK5-AS1, RP11-2F20.1, DGCR8, AC007563.1, UBE4A, AC004510.3, SYNCRIP, HSPH1, CTD-2206N4.2, LINC00919, RP11-17M16.2, ADGRG1, KRTCAP3, JARID2-AS1, CREB3L2, AC092168.3, RP11-493E12.1, SETD9, MRC2, AC008937.3, RP11-159D12.10, CCSER1, RP11-1018N14.1, FILIP1L, KIAA1217, RNFT2, NDUFA11, AC015971.2, CDH23, RP11-98D18.16, HNRNPH1, CTB-55O6.13, P4HTM, SMIM6, TTLL1, UQCRB, AC097495.2, RP11-796E2.4, LYSMD2, MGAT4C, RP11-862G15.1, PFN3, FAM212B, RBM15B, RNF103, RP11-396F22.1, C10orf82, SYS1, RP11-404L6.2, DDX5, LINC00906, PSMD3, PPP1R3E, PTK7, LINC01487, MAP3K14-AS1, MRPL9, ZFYVE28, KRTDAP, OSBP2, NUMBL, FKBP7, LMX1A, TXNDC2, ZCCHC8, RP11-666A8.9, RP5-1051H14.2, NRBP1, FAM170B-AS1, RP11-439E19.9, RPL37, MGST3, CTD-2020K17.4, SCRT1, RP11-173A6.3, FBXO34, MRFAP1, TRIM11, PCBP4, RANBP2, FAM229A, EQTN, GOLGA6L10, AC116609.1, MTPAP, GSTO1, PACS2, CTD-3035K23.7, RP11-73K9.2, FAM153A, CCDC80, ACTL7B, CFL1, RP11-1O10.1, GTSF1L, AC007557.4, SPIRE1, MRPS7, EAF1-AS1, RP11-545G3.1, IQCF3, CLIC5, SLC37A1, RP11-394A14.2, MYH7B, FKBP3, MINOS1, CENPJ, CFAP44, BRD2, RP11-684B21.1, AGAP1, FARP2, MIR7515HG, RP11-544A12.8, KMO, FAM209A, TMEM160, TAF5L, PSMA4, LINC01198, LDLRAD4, LINC00442, HYAL1, ATPAF1, C20orf144, ARF4-AS1, APOPT1, DNAAF3, EIF5A, NFIB, HPCA, CSPP1, IPO5, RP11-360D2.1, KATNBL1, EIF2B4, WI2-2373I1.2, POLB, FAM229B, RP11-326K13.4, FAM81B, PLCE1-AS2, BAZ2A, GNAI2, ZEB1, FAM83C, NDUFS8, DYNLL1, HMGB4, LMNTD2, C1orf43, LINC00943, RP1-266L20.2, SAMD4A, SNHG9, TLE4, CITED4, HDAC11, RP11-192H23.7, TMEM191C, TUBGCP4, PGP, PRM3, NDUFB6, RND2, WDR74, RP11-666O2.2, PIN1, ZNRD1, TAF10, H3F3B, COX7C, C3orf22, CLPB, NDUFA13, MYL6B, AURKAIP1, TMBIM6, GKAP1, CEP85L, DUSP15, TMEM38B, RP11-109E10.1, RNF139, ZMIZ2, CIB2, GDPD5, RCOR3, PPM1G, C7orf73, ZNF706, SNX13, DZIP1, HBP1, ZNF571-AS1, CPTP, C9orf173, BAG5, IZUMO4, C6orf120, MFAP3L, ZC3H15, LRRD1, ENO1, C9orf16, NAT6, BRK1, POLD2, SORBS3, RPL23A, AGPAT2, SMPD2, DMWD, ODC1, PCGF5, AC007325.4, CCDC37-AS1, PEX10, ACTL10, PAOX, ACTL7A, KDM5B, C11orf68, USP2, TMEM120A, EIF4E, EPN1, TCP1, UBAC1, TTC7A, C10orf62, RUVBL2, MAD2L2, AP2B1, MAATS1, RAD23B, PPP2R2B, ST13, KLHDC3, EEF1D, PTDSS2, SLC5A2, TP53I11, SLC2A8, C12orf50, RPL36, STARD10, TBC1D10B, CDHR2, ACE, ITPKA, DGCR14, RNF38, UBQLN3, DDX20, CCDC169, PARP6, PODXL2, RAB11FIP5, PDXK, PPDPF, FAM217A, GGN, GABRG3-AS1, RPS15, TPI1, AZIN2, RBCK1, DPP7, MLF1, ELOF1, PDXDC1, KTN1, ICA1, OPLAH, BZW1, RAD21, SPZ1, RTN4, CDIPT-AS1, SHARPIN, ZFAND3, ARF1, FNDC8, TOLLIP, MIS12, ATAD1, MEIOC, RP11-2C24.7, CCDC187, CTSF, SPPL2B, TTLL10, HAGLR, CCHCR1, CYB5R4, FBXL13, CCDC7.1, RPS9, CABS1, RNF11, FAM104A, EIFS, DYRK1B, ZMYM2, C21orf2, DDX3Y, C1orf159, DNAJC18, ZDHHC3, IL13, GINM1, CDV3, ZFAND4, C12orf75, CCPG1, STK35, AF131216.1, FAM76B, FAM234A, PSMF1, TEX38, GTSF1, VPRBP, RNF32, LCA5L, RPL41, CYB5R2, MROH7, TSPAN16, LRTOMT, AHCY, EGLN2, AC012594.1, USPL1, DDX3X, ITCH, WBP2NL, RPL19, CAMLG, NBR1, ARHGAP5, RAB3IP, IGSF11-AS1, SERF2, C6orf201, COL9A3, BRWD1-AS2, CENPU, TMEM215, STT3B, DHX57, RMND5B, SKP1, SLC25A39, CFAP221, PHACTR2-AS1, ZDHHC19, RPL15, ISG20L2, ESPN, PRKCZ, COPS5, TSPAN1, ZNF688, RP11-73G16.3, DCAF10, C17orf50, and YPEL5.

In some embodiments, the disclosure provides a method of determining a risk of paternal age effect (PAE) diseases in the offspring of the sperm donor. In a specific embodiment, the paternal age effect diseases include autism.

In some embodiments, the disclosed methods employ analysis and use of RNA for the genesis of cDNA and can include the use of an automated system. The methods further utilize analysis of a novel combination of genes as markers.

In some embodiments, it is determined that the sperm carries a risk for autism for the progeny if the expression level of at least one gene, i.e., one or more (e.g., at least 5, 10, 15, 20, 25, 30, 35, 40, 45, 50, 55, 60, 65, 70, 100, 200, 300 or all of the) genes, selected from the following group is upregulated in the sperm as compared to the level of expression of the same gene in a healthy control sperm: BACE1-AS, UNC119B, RP11-338I21.1, MEIS1, WDR55, IL6R, RP11-62H20.1, RP11-356J5.12, RP1-251M9.2, DNAJB4, MALSU1, EFCAB14, C3, RAB35, DNAJB7, DYNLL2, TIGAR, SSUH2, TPCN1, AL157902.3, STK32C, MED30, CTD-2083E4.6, LHX2, RP11-567M16.6, PHKB, CAHM, RP11-17A4.2, SIPA1L1, TMEM260, CDC42BPA, EVX1-AS, RP11-242D8.1, CDIPT, RP11-991C1.2, AP006216.5, RP11-696N14.1, TRABD, AC074391.1, CLCN3, RP11-644K8.1, GABARAPL1, ATF3, RFPL3S, CTD-2196E14.5, RP11-496I9.1, RP11-347D21.1, TRMT5, RP11-712B9.2, CSTL1, XXbac-BPG249D20.9, RP11-669C19.1, NRDE2, MAPT-AS1, EFCAB12, VGLL3, DCC, HSPB6, S100A7A, CTD-2135D7.2, KRT15, RP11-403A21.3, RP11-396C23.4, C10orf90, GMFG, KDM2B, TMSB4X, RP11-381K20.4, OR2H1, ZNF445, TEPP, CTC-543D15.8, CCDC155, MAPK3, RP5-1030M6.3, SORCS3-AS1, RP11-489E7.4, AC007163.3, XXyac-YX155B6.5, TP53TG5, C9orf3, APOL6, ARL4C, AC093627.10, SERPINB6, PIBF1, CDK19, RBBP6, RP11-140K17.3, EAF1, GLRX2, RP11-557J10.5, DAG1, RP11-96K19.5, WDR20, AC093818.1, NECAP2, RP11-375N15.2, DHDDS, LRRC52, WTIP, TNKS, CFAP157, COX8C, XPNPEP3, NOLC1, RARA-AS1, RP4-625H18.2, FANK1, PPP2R1B, RP11-168K9.1, MIR762HG, RP11-315I20.1, TADA2A, MEST, RP11-480I12.10, TMCO2, ZFP36L1, ATP1B3, CRAMP1, SPTY2D1-AS1, TNP1, AC007557.1, ACAP1, MARCKS, CTD-2568A17.1, PRM1, TCEB2, TMEM31, ARL6IP4, AACS, RSRC2, ZCCHC8, CTD-2363C16.1, KLHL12, CEP152, RP11-295M18.6, AC084219.4, HDAC4, DPP3, OVOS2, MAMDC2-AS1, FAM186A, ACSS1, CDIP1, INPP5B, PPP1R12B, RP11-527L4.6, ATP6V1A, EFCAB11, VN1R2, FAM179A, PELP1, STOML2, PCOLCE-AS1, AC004490.1, EVX2, RP11-258F1.1, CDKN1C, RP5-971N18.3, LAPTM4A, RP11-369E15.3, EIF5A2, PTPRD, RNF139-AS1, FAM71F1, CLK3, UGT1A6, C21orf91, DES, IBA57-AS1, HNRNPR, CCDC168, AC013436.6, ZNF32-AS3, LINC01095, MAPKAPK5-AS1, RP11-2F20.1, DGCR8, AC007563.1, UBE4A, AC004510.3, SYNCRIP, HSPH1, CTD-2206N4.2, LINC00919, RP11-17M16.2, ADGRG1, KRTCAP3, JARID2-AS1, CREB3L2, AC092168.3, RP11-493E12.1, SETD9, MRC2, AC008937.3, RP11-159D12.10, CCSER1, RP11-1018N14.1, FILIP1L, KIAA1217, RNFT2, NDUFA11, AC015971.2, CDH23, RP11-98D18.16, HNRNPH1, CTB-5506.13, P4HTM, SMIM6, TTLL1, UQCRB, AC097495.2, RP11-796E2.4, LYSMD2, MGAT4C, RP11-862G15.1, PFN3, FAM212B, RBM15B, RNF103, RP11-396F22.1, C10orf82, SYS1, RP11-404L6.2, DDX5, LINC00906, PSMD3, PPP1R3E, PTK7, LINC01487, MAP3K14-AS1, MRPL9, ZFYVE28, KRTDAP, OSBP2, NUMBL, FKBP7, LMX1A, TXNDC2, ZCCHC8, RP11-666A8.9, RP5-1051H14.2, NRBP1, FAM170B-AS1, RP11-439E19.9, RPL37, MGST3, CTD-2020K17.4, SCRT1, RP11-173A6.3, FBXO34, MRFAP1, TRIM11, PCBP4, RANBP2, FAM229A, EQTN, GOLGA6L10, AC116609.1, MTPAP, GSTO1, PACS2, CTD-3035K23.7, RP11-73K9.2, FAM153A, CCDC80, ACTL7B, CFL1, RP11-1O10.1, GTSF1L, AC007557.4, SPIRE1, MRPS7, EAF1-AS1, RP11-545G3.1, IQCF3, CLIC5, SLC37A1, RP11-394A14.2, MYH7B, FKBP3, MINOS1, CENPJ, CFAP44, BRD2, RP11-684B21.1, AGAP1, FARP2, MIR7515HG, RP11-544A12.8, KMO, FAM209A, TMEM160, TAF5L, PSMA4, LINC01198, LDLRAD4, LINC00442, HYAL1, ATPAF1, C20orf144, ARF4-AS1, APOPT1, DNAAF3, EIF5A, NFIB, HPCA, CSPP1, IPO5, RP11-360D2.1, KATNBL1, EIF2B4, WI2-2373I1.2, POLB, FAM229B, RP11-326K13.4, FAM81B, PLCE1-AS2, BAZ2A, GNAI2, ZEB1, FAM83C, NDUFS8, DYNLL1, HMGB4, LMNTD2, C1orf43, LINC00943, RP1-266L20.2, SAMD4A, SNHG9, TLE4, CITED4, HDAC11, RP11-192H23.7, TMEM191C, TUBGCP4, PGP, PRM3, NDUFB6, RND2, WDR74, RP11-666O2.2, PIN1, ZNRD1, TAF10, H3F3B, and COX7C.

In some embodiments, it is determined that the sperm carries a risk for autism for the progeny if the expression level of at least one gene, i.e., one or more (e.g., at least 5, 10, 15, 20, 25, 30, 35, 40, 45, 50, 55, 60, 65, 70, 100 or all of the) genes, selected from the following group is upregulated in the sperm as compared to the level of expression of the same gene in a healthy control sperm: BACE1-AS, UNC119B, RP11-338I21.1, MEIS1, WDR55, IL6R, RP11-62H20.1, RP11-356J5.12, RP1-251M9.2, DNAJB4, MALSU1, EFCAB14, C3, RAB35, DNAJB7, DYNLL2, TIGAR, SSUH2, TPCN1, AL157902.3, STK32C, MED30, CTD-2083E4.6, LHX2, RP11-567M16.6, PHKB, CAHM, RP11-17A4.2, SIPA1L1, TMEM260, CDC42BPA, EVX1-AS, RP11-242D8.1, CDIPT, RP11-991C1.2, AP006216.5, RP11-696N14.1, TRABD, AC074391.1, CLCN3, RP11-644K8.1, GABARAPL1, ATF3, RFPL3S, CTD-2196E14.5, RP11-496I9.1, RP11-347D21.1, TRMT5, RP11-712B9.2, CSTL1, XXbac-BPG249D20.9, RP11-669C19.1, NRDE2, MAPT-AS1, EFCAB12, VGLL3, DCC, HSPB6, S100A7A, CTD-2135D7.2, KRT15, RP11-403A21.3, RP11-396C23.4, C10orf90, GMFG, KDM2B, TMSB4X, RP11-381K20.4, OR2H1, ZNF445, TEPP, CTC-543D15.8, CCDC155, MAPK3, RP5-1030M6.3, SORCS3-AS1, RP11-489E7.4, AC007163.3, XXyac-YX155B6.5, TP53TG5, C9orf3, APOL6, ARL4C, AC093627.10, SERPINB6, PIBF1, CDK19, RBBP6, RP11-140K17.3, EAF1, GLRX2, RP11-557J10.5, DAG1, RP11-96K19.5, WDR20, AC093818.1, NECAP2, RP11-375N15.2, DHDDS, LRRC52, WTIP, TNKS, CFAP157, COX8C, XPNPEP3, NOLC1, RARA-AS1, RP4-625H18.2, FANK1, PPP2R1B, RP11-168K9.1, ARL6IP4, AACS, RSRC2, and ZCCHC8.

In some embodiments, it is determined that the sperm carries a risk for autism for the progeny if the expression level of at least one gene, i.e., one or more (e.g., at least 5, 10, 15, or all of the) genes, selected from the following group is upregulated in the sperm as compared to the level of expression of the same gene in a healthy control sperm: MIR762HG, RP11-315I20.1, TADA2A, MEST, RP11-480I12.10, TMCO2, ZFP36L1, ATP1B3, CRAMP1, SPTY2D1-AS1, TNP1, AC007557.1, ACAP1, MARCKS, CTD-2568A17.1, PRM1, TCEB2, and TMEM31.

In some embodiments, it is determined that the sperm carries a risk for autism for the progeny if the expression level of at least one gene, i.e., one or more (e.g., at least 5, 10, 15, 20, 25, 30, 35, 40, 45, 50, 55, 60, 65, 70, 100, 150, 200 or all of the) genes, selected from the following group is upregulated in the sperm as compared to the level of expression of the same gene in a healthy control sperm: CTD-2363C16.1, KLHL12, CEP152, RP11-295M18.6, AC084219.4, HDAC4, DPP3, OVOS2, MAMDC2-AS1, FAM186A, ACSS1, CDIP1, INPP5B, PPP1R12B, RP11-527L4.6, ATP6V1A, EFCAB11, VN1R2, FAM179A, PELP1, STOML2, PCOLCE-AS1, AC004490.1, EVX2, RP11-258F1.1, CDKN1C, RP5-971N18.3, LAPTM4A, RP11-369E15.3, EIF5A2, PTPRD, RNF139-AS1, FAM71F1, CLK3, UGT1A6, C21orf91, DES, IBA57-AS1, HNRNPR, CCDC168, AC013436.6, ZNF32-AS3, LINC01095, MAPKAPK5-AS1, RP11-2F20.1, DGCR8, AC007563.1, UBE4A, AC004510.3, SYNCRIP, HSPH1, CTD-2206N4.2, LINC00919, RP11-17M16.2, ADGRG1, KRTCAP3, JARID2-AS1, CREB3L2, AC092168.3, RP11-493E12.1, SETD9, MRC2, AC008937.3, RP11-159D12.10, CCSER1, RP11-1018N14.1, FILIP1L, KIAA1217, RNFT2, NDUFA11, AC015971.2, CDH23, RP11-98D18.16, HNRNPH1, CTB-5506.13, P4HTM, SMIM6, TTLL1, UQCRB, AC097495.2, RP11-796E2.4, LYSMD2, MGAT4C, RP11-862G15.1, PFN3, FAM212B, RBM15B, RNF103, RP11-396F22.1, C10orf82, SYS1, RP11-404L6.2, DDX5, LINC00906, PSMD3, PPP1R3E, PTK7, LINC01487, MAP3K14-AS1, MRPL9, ZFYVE28, KRTDAP, OSBP2, NUMBL, FKBP7, LMX1A, TXNDC2, ZCCHC8, RP11-666A8.9, RP5-1051H14.2, NRBP1, FAM170B-AS1, RP11-439E19.9, RPL37, MGST3, CTD-2020K17.4, SCRT1, RP11-173A6.3, FBXO34, MRFAP1, TRIM11, PCBP4, RANBP2, FAM229A, EQTN, GOLGA6L10, AC116609.1, MTPAP, GSTO1, PACS2, CTD-3035K23.7, RP11-73K9.2, FAM153A, CCDC80, ACTL7B, CFL1, RP11-1O10.1, GTSF1L, AC007557.4, SPIRE1, MRPS7, EAF1-AS1, RP11-545G3.1, IQCF3, CLIC5, SLC37A1, RP11-394A14.2, MYH7B, FKBP3, MINOS1, CENPJ, CFAP44, BRD2, RP11-684B21.1, AGAP1, FARP2, MIR7515HG, RP11-544A12.8, KMO, FAM209A, TMEM160, TAF5L, PSMA4, LINC01198, LDLRAD4, LINC00442, HYAL1, ATPAF1, C20orf144, ARF4-AS1, APOPT1, DNAAF3, EIF5A, NFIB, HPCA, CSPP1, IPO5, RP11-360D2.1, KATNBL1, EIF2B4, WI2-237I1.2, POLB, FAM229B, RP11-326K13.4, FAM81B, PLCE1-AS2, BAZ2A, GNAI2, ZEB1, FAM83C, NDUFS8, DYNLL1, HMGB4, LMNTD2, C1orf43, LINC00943, RP1-266L20.2, SAMD4A, SNHG9, TLE4, CITED4, HDAC11, RP11-192H23.7, TMEM191C, TUBGCP4, PGP, PRM3, NDUFB6, RND2, WDR74, RP11-666O2.2, PIN1, ZNRD1, TAF10, H3F3B, and COX7C.

In some embodiments, it is determined that the sperm carries a risk for autism for the progeny if the expression level of at least one gene, i.e., one or more (e.g., at least 5, 10, 15, 20, 25, 30, 35, 40, 45, or all of the) genes, selected from the following group is upregulated in the sperm as compared to the level of expression of the same gene in a healthy control sperm: BACE1-AS, UNC119B, RP11-338I21.1, TIGAR, TPCN1, RP11-567M16.6, CAHM, EVX1-AS, CDIPT, RP11-991C1.2, CLCN3, GABARAPL1, ATF3, CTD-2196E14.5, CSTL1, EFCAB12, VGLL3, HSPB6, TMSB4X, KDM2B, SORCS3-AS1, RP11-140K17.3, GLRX2, DAG1, WDR20, DHDDS, LRRC52, MIR762HG, RP11-315I20.1, TADA2A, MEST, RP11-480I12.10, TMCO2, ZFP36L1, ATP1B3, CRAMP1, SPTY2D1-AS1, TNP1, AC007557.1, ACAP1, MARCKS, CTD-2568A17.1, PRM1, TCEB2, TMEM31, and MEX3D.

In some embodiments, it is determined that the sperm carries a risk for autism for the progeny if the expression level of at least one gene, i.e., one or more (e.g., at least 5, 10, 15, 20, 25, 30, 35, 40, 45, 50, 55, 60, 65, 70, 100, 150, 200, 250, 300 or all of the) genes, selected from the following group is downregulated in the sperm as compared to the level of expression of the same gene in a healthy control sperm: PHOSPHO1, ETNK2, C17orf74, DGCR6L, ODF3L2, CIB1, NUPR2, C16orf82, UBXN6, DNAJC4, UBA52, REEP6, LELP1, RANGAP1, TNFAIP8L1, ARL4A, PRM2, TPGS2, CSNK1G2, LPIN1, ZNHIT2, PCSK4, PCYT2, OAZ3, TPPP2, SMCP, FBXW5, TCP11, BOD1L2, CARHSP1, GLUL, C2orf57, SMKR1, PTP4A1, CCSER2, AQP5, MPC2, RGS22, PKM, MOSPD3, CCDC136, AC012370.3, VTI1B, INCA1, SPATC1L, CXCL16, METAP1, USP25, SH3GL3, MAP2K2, CRAT, RPS27A, RPL29, RPL13, ANKRD12, TUBB4B, NRAV, FAM220A, FXR1, BSG, TSPAN6, RPL12, PWRN1, SRP54, CCNY, PVRL3, BPIFA3, PTOV1, ADO, NSUN4, SRPK2, RIOK3, SPCS1, GPR137, UBE2N, RPL8, WASF1, FUNDC2, HDLBP, SPTBN2, SLFNL1, GSG1, NT5C1B, PPP2R5A, PHKG2, PROCA1, INPP5K, PDZD8, ABHD1, SLAIN2, SPATA3, TSSK6, UBE2D2, PRC1-AS1, VWA3B, HSPA4L, FKBP8, MFF, LINC00901, GNAS, RNF138, CABYR, TSSK1B, TSSK2, SPATA18, RPS18, SLC38A7, TPD52L3, ACSBG2, RP11-14J7.7, RPLP1, TPP2, PSMD6, PAFAH1B1, UBA5, RPL37A, GAPDH, RPS8, C17orf97, CCDC91, SEC14L1, MTFR1L, DCUN1D1, RAB1A, CRISP2, RPS6, PGK2, VRK3, BAZ1A, TPT1, AKAP1, MS4A14, CCDC7, SEMG1, SARAF, RPL13A, FTH1, CUL3, POLR1D, MT-CO2, FSCB, RPS4X, CLU, RPL3, PLBD2, RPL10, C3orf22, CLPB, NDUFA13, MYL6B, AURKAIP1, TMBIM6, GKAP1, CEP85L, DUSP15, TMEM38B, RP11-109E10.1, RNF139, ZMIZ2, CIB2, GDPD5, RCOR3, PPM1G, C7orf73, ZNF706, SNX13, DZIP1, HBP1, ZNF571-AS1, CPTP, C9orf173, BAG5, IZUMO4, C6orf120, MFAP3L, ZC3H15, LRRD1, ENO1, C9orf16, NAT6, BRK1, POLD2, SORBS3, RPL23A, AGPAT2, SMPD2, DMWD, ODC1, PCGF5, AC007325.4, CCDC37-AS1, PEX10, ACTL10, PAOX, ACTL7A, KDM5B, C11orf68, USP2, TMEM120A, EIF4E, EPN1, TCP1, UBAC1, TTC7A, C10orf62, RUVBL2, MAD2L2, AP2B1, MAATS1, RAD23B, PPP2R2B, ST13, KLHDC3, EEF1D, PTDSS2, SLC5A2, TP53I11, SLC2A8, C12orf50, RPL36, STARD10, TBC1D10B, CDHR2, ACE, ITPKA, DGCR14, RNF38, UBQLN3, DDX20, CCDC169, PARP6, PODXL2, RAB11FIP5, PDXK, PPDPF, FAM217A, GGN, GABRG3-AS1, RPS15, TPI1, AZIN2, RBCK1, DPP7, MLF1, ELOF1, PDXDC1, KTN1, ICA1, OPLAH, BZW1, RAD21, SPZ1, RTN4, CDIPT-AS1, SHARPIN, ZFAND3, ARF1, FNDC8, TOLLIP, MIS12, ATAD1, MEIOC, RP11-2C24.7, CCDC187, CTSF, SPPL2B, TTLL10, HAGLR, CCHCR1, CYB5R4, FBXL13, CCDC7.1, RPS9, CABS1, RNF11, FAM104A, EIF5, DYRK1B, ZMYM2, C21orf2, DDX3Y, C1orf159, DNAJC18, ZDHHC3, IL13, GINM1, CDV3, ZFAND4, C12orf75, CCPG1, STK35, AF131216.1, FAM76B, FAM234A, PSMF1, TEX38, GTSF1, VPRBP, RNF32, LCA5L, RPL41, CYB5R2, MROH7, TSPAN16, LRTOMT, AHCY, EGLN2, AC012594.1, USPL1, DDX3X, ITCH, WBP2NL, RPL19, CAMLG, NBR1, ARHGAP5, RAB3IP, IGSF11-AS1, SERF2, C6orf201, COL9A3, BRWD1-AS2, CENPU, TMEM215, STT3B, DHX57, RMND5B, SKP1, SLC25A39, CFAP221, PHACTR2-AS1, ZDHHC19, RPL15, ISG20L2, ESPN, PRKCZ, COPS5, TSPAN1, ZNF688, RP11-73G16.3, DCAF10, C17orf50, and YPEL5.

In some embodiments, it is determined that the sperm carries a risk for autism for the progeny if the expression level of at least one gene, i.e., one or more (e.g., at least 5, 10, 15, 20, 25, 30, 35, 40, or all of the) genes, selected from the following group is downregulated in the sperm as compared to the level of expression of the same gene in a healthy control sperm: PHOSPHO1, ETNK2, C17orf74, DGCR6L, ODF3L2, CIB1, NUPR2, C16orf82, UBXN6, DNAJC4, UBA52, REEP6, LELP1, RANGAP1, TNFAIP8L1, ARL4A, PRM2, TPGS2, CSNK1G2, LPIN1, ZNHIT2, PCSK4, PCYT2, OAZ3, TPPP2, SMCP, FBXW5, TCP11, BOD1L2, CARHSP1, GLUL, C2orf57, SMKR1, PTP4A1, CCSER2, AQP5, MPC2, RGS22, PKM, and MOSPD3.

In some embodiments, it is determined that the sperm carries a risk for autism for the progeny if the expression level of at least one gene, i.e., one or more (e.g., at least 5, 10, 15, 20, 25, 30, 35, 40, 45, 50, 55, 60, 65, 70, 100 or all of the) genes, selected from the following group is downregulated in the sperm as compared to the level of expression of the same gene in a healthy control sperm: CCDC136, AC012370.3, VTI1B, INCA1, SPATC1L, CXCL16, METAP1, USP25, SH3GL3, MAP2K2, CRAT, RPS27A, RPL29, RPL13, ANKRD12, TUBB4B, NRAV, FAM220A, FXR1, BSG, TSPAN6, RPL12, PWRN1, SRP54, CCNY, PVRL3, BPIFA3, PTOV1, ADO, NSUN4, SRPK2, RIOK3, SPCS1, GPR137, UBE2N, RPL8, WASF1, FUNDC2, HDLBP, SPTBN2, SLFNL1, GSG1, NT5C1B, PPP2R5A, PHKG2, PROCA1, INPP5K, PDZD8, ABHD1, SLAIN2, SPATA3, TSSK6, UBE2D2, PRC1-AS1, VWA3B, HSPA4L, FKBP8, MFF, LINC00901, GNAS, RNF138, CABYR, TSSK1B, TSSK2, SPATA18, RPS18, SLC38A7, TPD52L3, ACSBG2, RP11-14J7.7, RPLP1, TPP2, PSMD6, PAFAH1B1, UBA5, RPL37A, GAPDH, RPS8, C17orf97, CCDC91, SEC14L1, MTFR1L, DCUN1D1, RAB1A, CRISP2, RPS6, PGK2, VRK3, BAZ1A, TPT1, AKAP1, MS4A14, CCDC7, SEMG1, SARAF, RPL13A, FTH1, CUL3, POLR1D, MT-CO2, FSCB, RPS4X, CLU, RPL3, PLBD2, and RPL10.

In some embodiments, it is determined that the sperm carries a risk for autism for the progeny if the expression level of at least one gene, i.e., one or more (e.g., at least 5, 10, 15, 20, 25, 30, 35, 40, 45, 50, 55, 60, 65, 70, 100, 150, 170 or all of the) genes, selected from the following group is downregulated in the sperm as compared to the level of expression of the same gene in a healthy control sperm: C3orf22, CLPB, NDUFA13, MYL6B, AURKAIP1, TMBIM6, GKAP1, CEP85L, DUSP15, TMEM38B, RP11-109E10.1, RNF139, ZMIZ2, CIB2, DSPD5, RCOR3, PPM1G, C7orf73, ZNF706, SNX13, DZIP1, HBP1, ZNF571-AS1, CPTP, C9orf173, BAG5, IZUMO4, C6orf120, MFAP3L, ZC3H15, LRRD1, ENO1, C9orf16, NAT6, BRK1, POLD2, SORBS3, RPL23A, AGPAT2, SMPD2, DMWD, ODC1, PCGF5, AC007325.4, CCDC37-AS1, PEX10, ACTL10, PAOX, ACTL7A, KDMSB, C11orf68, USP2, TMEM120A, EIF4E, EPN1, TCP1, UBAC1, TTC7A, C10orf62, RUVBL2, MAD2L2, AP2B1, MAATS1, RAD23B, PPP2R2B, ST13, KLHDC3, EEF1D, PTDSS2, SLC5A2, TP53I11, SLC2A8, C12orf50, RPL36, STARD10, TBC1D10B, CDHR2, ACE, ITPKA, DGCR14, RNF38, UBQLN3, DDX20, CCDC169, PARP6, PODXL2, RAB11FIP5, PDXK, PPDPF, FAM217A, GGN, GABRG3-AS1, RPS15, TPI1, AZIN2, RBCK1, DPP7, MLF1, ELOF1, PDXDC1, KTN1, ICA1, OPLAH, BZW1, RAD21, SPZ1, RTN4, CDIPT-AS1, SHARPIN, ZFAND3, ARF1, FNDC8, TOLLIP, MIS12, ATAD1, MEIOC, RP11-2C24.7, CCDC187, CTSF, SPPL2B, TTLL10, HAGLR, CCHCR1, CYB5R4, FBXL13, CCDC7.1, RPS9, CABS1, RNF11, FAM104A, EIFS, DYRK1B, ZMYM2, C21orf2, DDX3Y, C1orf159, DNAJC18, ZDHHC3, IL13, GINM1, CDV3, ZFAND4, C12orf75, CCPG1, STK35, AF131216.1, FAM76B, FAM234A, PSMF1, TEX38, GTSF1, VPRBP, RNF32, LCA5L, RPL41, CYB5R2, MROH7, TSPAN16, LRTOMT, AHCY, EGLN2, AC012594.1, USPL1, DDX3X, ITCH, WBP2NL, RPL19, CAMLG, NBR1, ARHGAP5, RAB3IP, IGSF11-AS1, SERF2, C6orf201, COL9A3, BRWD1-AS2, CENPU, TMEM215, STT3B, DHX57, RMND5B, SKP1, SLC25A39, CFAP221, PHACTR2-AS1, ZDHHC19, RPL15, ISG20L2, ESPN, PRKCZ, COPS5, TSPAN1, ZNF688, RP11-73G16.3, DCAF10, C17orf50, and YPEL5.

In some embodiments, it is determined that the sperm carries a risk for autism for the progeny if the expression level of at least one gene, i.e., one or more (e.g., at least 5, 10, 15, 20, 25, 30, 35, 40, 45, 50, 55, 60, or all of the) genes, selected from the following group is upregulated as compared to the expression of the same gene in a autistic control sperm: PHOSPHO1, ETNK2, SLC39A13, C17orf74, DGCR6L, CRIP2, ODF3L2, CIB1, NUPR2, C16orf82, UBXN6, DNAJC4, UBA52, REEP6, LELP1, RANGAP1, TNFAIP8L1, ARL4A, PRM2, TPGS2, CSNK1G2, LPIN1, ZNHIT2, PCSK4, PCYT2, OAZ3, TPPP2, SMCP, FBXW5, TCP11, BOD1L2, CARHSP1, GLUL, C2orf57, SMKR1, PTP4A1, CCSER2, AQP5, MPC2, RGS22, PKM, MOSPD3, RPL13, SH3GL3, CXCL16, TSPAN6, CCNY, PROCA1, ABHD1, TSSK6, FKBP8, MFF, GNAS, SPATA18, TSSK2, ACSBG2, PAFAH1B1, GAPDH, CCDC91, DCUN1D1, CRISP2, VRK3, and AKAP1.

In some embodiments, the sperm which, based on the gene profile analysis of any of the above-disclosed methods, is determined to carry a risk of autism will not be used for in vitro fertilization and conception of a new child.

In some embodiments, this invention will represent a DNA or RNA sperm analysis which can be automated.

In some embodiments, the sperm is not human but rather from another mammal such as a pig, horse, sheep or a cow. The analysis is suitable to determine the optimal sperm to use for artificial insemination or IVF in the farm animals.

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The specific examples listed below are only illustrative and by no means limiting.

EXAMPLES

Example 1: Materials and Methods

Samples

The sperm samples were purchased from the California Cryobank (Los Angeles, CA). All of the donors signed an informed consent with the Cryobank where they agreed that their samples could be used in research. Since the donors of sperm at Cryobank are purchased by women to have a child, many of the donors have a large number of children. Interestingly, there are cases where a donor will have one of his many children having autism and the rest will be unaffected, indicating that there are other causes of autism besides paternal genetics. For this reason, we required that our Autism Spectrum Disorder (ASD) donors have evidence of at least 2 children with ASD. The control donors needed to have multiple children with no evidence of ASD. The samples were sent on liquid nitrogen from the Cryobank to our lab where they were thawed for analysis.

Cell Preparation

Frozen sperm cell vials were obtained from California Cryobank Biotech. Sperm cells were provided with expected post-thaw cell count. Frozen cells were rapidly thawed in a 37° C. water bath. Thawed cells were centrifuged at 300 r.c.f. for 10 minutes and 1x PBS with 0.04% bovine serum albumin was used for washing the cells twice as well as resuspension of the cells at room temperature.

Single Cell Library Construction and Sequencing

Cell suspensions post washing was loaded on the 10X Chromium System (10x Genomics, Pleasanton, CA) for single cell isolation into Gel Bead Emulsions (GEMs) as per manufacturer's instruction in Chromium Single Cell 3' Reagent Kits v2 User Guide, Rev A (Zheng et al., *Nature Communications*, 8. 2017:14049) using Chromium Single Cell 3' Solution (Chromium Single Cell 3' Chip Kit v2 [PN-120236], Gel Bead kit v2 [PN-120235]. The input cells per channel in the chip were targeted around ~1 million cells based on provided initial post-thaw cell count from California Cryobank biotech. Target of ~1 million cells was to increase the poor RNA yield from sperm cells. However, the loss of cells during washing would reduce the actual cell counts to input significantly less than targeted cells. Peripheral Blood Mononuclear Cells (PBMC) was loaded on each single cell chip as a control to determine sample type associated failures on the Chromium System. PBMCs were freshly isolated from whole blood with Ficoll method and washed twice with 1xPBS with 0.04% bovine serum albumin Approximately, 10,000 cells of PBMC were loaded in a channel per chip.

Eight sperm samples failed to generate uniform GEMs due to "reagent clogs", "Wetting Failures" and "Pressure not at Setpoint", which are possible failure modes during GEM generation described with details in manufacturer's protocol. These failed samples were removed from further library construction and sequencing.

Sperm samples that successfully generated proper GEMS were further processed for GEM-RT incubation, cDNA amplification and subsequent single cell library construction using Chromium™ Single Cell 3' library Kit v2 [PN-120234] following the manufacturer's protocol. Barcoded final libraries were quantified by QUBIT® 2.0 Fluorometer (Invitrogen) and qPCR (KAPA Biosystems Library Quantification kit) and fragment size profiles were assessed from Agilent 2100 Bioanalyzer. All libraries were sequenced on Illumina HiSeq 2500 with 2X 100 paired-end kits using following read length: 26 bp read 1, 8 bp i7 index and 98 bp Read 2.

Cell Ranger (version 1.2) Single Cell pipeline (10X Genomics) was used for de-multiplexing libraries using cellranger mkfastq to generate FASTQ files. STAR alignment, Barcode and UMI processing and counting were conducted by cellranger count pipeline. Filtering of the barcodes, UMI and duplicates are described in Zheng et al. (*Nature Communications*, 8. 2017:14049).

Assessment of Background Cell-Free RNA

Thawed Sperm cells that was not used for single cell isolation were frozen as aliquots and stored in liquid nitrogen storage dewar. At a later date, the frozen sperm aliquots were thawed in a water bath at 37° C. and centrifuged at 300 r.c.f for 10 min In order to investigate the presence of background cell-free RNA in sperm samples, the supernatant was acquired to assess for any presence of RNA. 5 µl of the supernatant was used to amplify any present RNA using Ovation® RNA-Seq system V2 amplification kit (NuGen Technologies, San Carlos, CA) using manufacturer's instruction. Five control samples with input ranging ~0.75-4 ng were amplified in the same batch. The amplified product was purified using MinElute PCR Purification. Final yield and quality was checked using QUBIT® 2.0 Fluorometer and on the Agilent 2100 Bioanalyzer, respectively. Approximately, 2 µg amplified cDNA from each sample was sheared on a Covaris S200 focused-ultrasonicator (Woburn, MA, USA) with a target yield of 200 bp fragment size. Fragmented DNA was taken into standard library preparation using NEBNext® DNA Library Prep Master Mix Set for ILLUMINA® (New England BioLabs Inc., Ipswich, MA, USA) with slight modifications. Briefly, after sonication "End-repair" was done followed by "polyA addition" and "adapter ligation". Post-ligated samples were individually barcoded with unique in-house GSL primers and amplified through 6 cycles of PCR using KAPA HiFi HotStart Ready Mix (Kapa Biosystems, Inc., Woburn, MA, USA). The concentration and quality of the libraries were assessed by QUBIT® 2.0 Fluorometer and Agilent 2100 Bioanalyzer, respectively. Accurate quantification for sequencing applications was determined using the qPCR-based KAPA Biosystems Library Quantification kit (Kapa Biosystems, Inc., Woburn, MA, USA). 50 bp Paired End (PE) sequencing was performed to generate approximately 50 million reads per sample.

Example 2

In order to provide greater clarity as to the variation between individual sperm in a sample, the inventors used a single-cell sequencing approach. Single-cell sequencing provides for a method of determine the nucleotide sequences in each individual cell. In general, the techniques work by separating the individual cells either physically or chemically. The nucleic acids from each cell are then given a unique tag that will allow them to be de-convoluted from a mixture of DNA or RNA that has been sequenced. Currently, the tools for high-throughput whole genome single-cell RNA sequencing are much more advanced than those for DNA sequencing. One main reason for this is that in contrast to the 2 copies of each chromosome in a normal cell, there are hundreds or thousands of copies of the RNA of genes that are being expressed. Therefore, the inventors performed single-cell RNA sequencing of individual sperm cells.

Sperm samples were obtained from 2 donors that have multiple children with Autism Spectrum Disorders (ASD) and from 4 donors who do not have any children with ASD. Using the 10X Chromium platform, the inventors have been able to sequence tens of thousands of individual sperms from each donor. The inventors performed inter- and intra-individual analysis and found that there are a substantial number of genes whose expression is variable in the sperm samples. In addition, the inventors used a unique approach to perform variant calling on the RNA reads to detect evidence of mutations occurring in the sperm cell development. This is the first case of mutational detection based upon single-cell RNA-seq. Based upon the small sample size, the inventors found evidence that there are mutations occurring in sperm on both an expression and a variant level that correlate with ASD in offspring/progeny children.

Variant Calling

Since the inventors performed RNA-sequencing, the main goal is generally expression analysis, but the inventors realized that there is sufficient depth from the sequencing to investigate sequence variants. These variants will be limited to the genes that are highly expressed in the sperm and to those in the 3' ends of the RNAs that are sequenced. While this is a small fraction of the genome, it is sufficient to get a rough picture of DNA variation in sperm. It also serves as a pilot to investigate variant calling in other single-cell RNA datasets.

The BAM file produced by the CellRanger software is not designed to easily allow for variant calling and needs to be modified. In particular, the reads from each individual cell are marked with the CB tag in the BAM file whereas a typical BAM file would record each set of reads from the same source as a read-group with the RG tag. The inventors developed a perl script that converted the BAM file and also removed any of the cells that had less than 100 reads per cell. The standard freebayes variant caller was then run on the converted BAM files and we removed any variants with a quality of <20 and required that a SNP be present in 100 individual single cells to report it. Thus, the identified SNPs were rare in the sperm population, but were not only found in an individual cell. For each sample there were between 194 and 302 SNPs that were found in a sufficient number of cells. Non-synonymous SNPS were found in the CARHSP1, CRISP2, DNAJC4, NUPR2, PRM1, PRM2, SMCP genes.

One of the main goals of single-cell sequencing is to uncover information that cannot be detected in the bulk sample. Due to the need for multiple sequencing reads to call a variant and the errors in the sequencing machines, variants generally cannot be called below a 10% minor allele frequency. This means that for a cell population, a variant needs to be present in a least 1 in 10 cells for it to be detectable from standard sequencing. In a single-cell approach this is not the case since we are able to look at the reads from each cell individually. A SNP that appears in only an individual cell would be detectable.

To determine whether the SNPs that the inventors identified would have been found from standard sequencing, the inventors ran freebayes on all of the reads from each sample without distinguishing between those that came from a particular cell. This produced a rough equivalent of what would have been found had an RNA-seq of the bulk sperm sample been done. Over 95% of the SNPs that were detected from the single-cell variant calling (Table 1) were not found in the bulk sperm variant calling. These SNPs were only found from the single cell sequencing are represent rare populations that would be missed from bulk sequencing.

TABLE 1

Comparison of single sperm variant calling and bulk sperm variant calling

| Sample | # of SNPs only in Single Cells | Total # of Single Cell SNPs | Percentage |
| --- | --- | --- | --- |
| num5 | 299 | 302 | 99% |
| num6 | 183 | 193 | 95% |
| num7 | 239 | 249 | 96% |
| num8 | 188 | 194 | 97% |
| num9 | 186 | 188 | 99% |
| num10 | 201 | 206 | 98% |

TABLE 2

Tier 1 genes (ranked by Average log Fold Change (avg_logFC)).

| | GeneName | p_val | avg_logFC | pct.1 | pct.2 | p_val_adj | Marker Type | Tier |
| --- | --- | --- | --- | --- | --- | --- | --- | --- |
| 1 | BACE1-AS | 3.16E−255 | 2.69963958 | 0.053 | 0 | 2.12E−251 | Higher in Autistic Samples | I |
| 2 | UNC119B | 3.67E−215 | 2.16063592 | 0.053 | 0.003 | 2.46E−211 | Higher in Autistic Samples | I |
| 3 | RP11-338I21.1 | 3.03E−204 | 2.0182836 | 0.055 | 0.004 | 2.03E−200 | Higher in Autistic Samples | I |
| 4 | MEIS1 | 1.30E−120 | 1.95000939 | 0.028 | 0.001 | 8.71E−117 | Higher in Autistic Samples | I |
| 5 | WDR55 | 9.09E−117 | 1.81805974 | 0.031 | 0.002 | 6.09E−113 | Higher in Autistic Samples | I |
| 6 | IL6R | 3.75E−114 | 1.81393765 | 0.029 | 0.002 | 2.51E−110 | Higher in Autistic Samples | I |
| 7 | RP11-62H20.1 | 1.39E−114 | 1.73993774 | 0.03 | 0.002 | 9.35E−111 | Higher in Autistic Samples | I |
| 8 | RP11-356J5.12 | 6.09E−166 | 1.72576531 | 0.05 | 0.006 | 4.08E−162 | Higher in Autistic Samples | I |
| 9 | RP1-251M9.2 | 1.15E−111 | 1.74475127 | 0.028 | 0.002 | 7.70E−108 | Higher in Autistic Samples | I |
| 10 | DNAJB4 | 5.67E−140 | 1.69517492 | 0.039 | 0.004 | 3.80E−136 | Higher in Autistic Samples | I |
| 11 | MALSU1 | 1.15E−93 | 1.63612258 | 0.027 | 0.003 | 7.71E−90 | Higher in Autistic Samples | I |
| 12 | EFCAB14 | 1.93E−125 | 1.62727825 | 0.037 | 0.004 | 1.29E−121 | Higher in Autistic Samples | I |
| 13 | C3 | 1.49E−127 | 1.59881396 | 0.038 | 0.004 | 9.99E−124 | Higher in Autistic Samples | I |
| 14 | RAB35 | 2.17E−140 | 1.59781958 | 0.043 | 0.005 | 1.45E−136 | Higher in Autistic Samples | I |
| 15 | DNAJB7 | 9.57E−88 | 1.58377721 | 0.026 | 0.003 | 6.42E−84 | Higher in Autistic Samples | I |
| 16 | DYNLL2 | 4.04E−132 | 1.57333063 | 0.042 | 0.005 | 2.71E−128 | Higher in Autistic Samples | I |
| 17 | TIGAR | 5.57E−219 | 1.57265917 | 0.08 | 0.014 | 3.73E−215 | Higher in Autistic Samples | I |
| 18 | SSUH2 | 2.75E−107 | 1.55372491 | 0.03 | 0.003 | 1.84E−103 | Higher in Autistic Samples | I |
| 19 | TPCN1 | 2.47E−155 | 1.52994606 | 0.051 | 0.007 | 1.65E−151 | Higher in Autistic Samples | I |
| 20 | AL157902.3 | 1.66E−98 | 1.51782264 | 0.031 | 0.004 | 1.11E−94 | Higher in Autistic Samples | I |
| 21 | STK32C | 1.38E−101 | 1.49442151 | 0.032 | 0.004 | 9.28E−98 | Higher in Autistic Samples | I |

TABLE 2-continued

Tier 1 genes (ranked by Average log Fold Change (avg_logFC)).

| | GeneName | p_val | avg_logFC | pct.1 | pct.2 | p_val_adj | Marker Type | Tier |
|---|---|---|---|---|---|---|---|---|
| 22 | MED30 | 4.78E−58 | 1.48022813 | 0.012 | 0 | 3.21E−54 | Higher in Autistic Samples | I |
| 23 | CTD-2083E4.6 | 2.75E−82 | 1.4801585 | 0.024 | 0.003 | 1.84E−78 | Higher in Autistic Samples | I |
| 24 | LHX2 | 2.00E−78 | 1.47496469 | 0.021 | 0.002 | 1.34E−74 | Higher in Autistic Samples | I |
| 25 | RP11-567M16.6 | 3.06E−157 | 1.44873057 | 0.06 | 0.011 | 2.05E−153 | Higher in Autistic Samples | I |
| 26 | PHKB | 1.81E−75 | 1.43121654 | 0.024 | 0.003 | 1.21E−71 | Higher in Autistic Samples | I |
| 27 | CAHM | 1.35E−158 | 1.41545555 | 0.061 | 0.011 | 9.07E−155 | Higher in Autistic Samples | I |
| 28 | RP11-17A4.2 | 4.87E−122 | 1.3941909 | 0.046 | 0.009 | 3.27E−118 | Higher in Autistic Samples | I |
| 29 | SIPA1L1 | 3.83E−74 | 1.36924674 | 0.024 | 0.003 | 2.56E−70 | Higher in Autistic Samples | I |
| 30 | TMEM260 | 4.96E−95 | 1.34016046 | 0.036 | 0.007 | 3.33E−91 | Higher in Autistic Samples | I |
| 31 | CDC42BPA | 9.42E−71 | 1.31190904 | 0.024 | 0.004 | 6.31E−67 | Higher in Autistic Samples | I |
| 32 | EVX1-AS | 3.39E−213 | 1.285473 | 0.095 | 0.022 | 2.27E−209 | Higher in Autistic Samples | I |
| 33 | RP11-242D8.1 | 1.41E−71 | 1.25986343 | 0.024 | 0.004 | 9.48E−68 | Higher in Autistic Samples | I |
| 34 | CDIPT | 9.37E−156 | 1.23303731 | 0.072 | 0.017 | 6.28E−152 | Higher in Autistic Samples | I |
| 35 | RP11-991C1.2 | 2.01E−131 | 1.22884725 | 0.058 | 0.013 | 1.35E−127 | Higher in Autistic Samples | I |
| 36 | AP006216.5 | 2.99E−73 | 1.22515747 | 0.028 | 0.005 | 2.00E−69 | Higher in Autistic Samples | I |
| 37 | RP11-696N14.1 | 1.06E−67 | 1.22372877 | 0.025 | 0.004 | 7.09E−64 | Higher in Autistic Samples | I |
| 38 | TRABD | 1.34E−96 | 1.21573485 | 0.038 | 0.007 | 8.96E−93 | Higher in Autistic Samples | I |
| 39 | AC074391.1 | 1.29E−76 | 1.2149634 | 0.028 | 0.005 | 8.66E−73 | Higher in Autistic Samples | I |
| 40 | CLCN3 | 1.61E−230 | 1.19988443 | 0.119 | 0.034 | 1.08E−226 | Higher in Autistic Samples | I |
| 41 | RP11-644K8.1 | 9.76E−96 | 1.19071369 | 0.04 | 0.008 | 6.55E−92 | Higher in Autistic Samples | I |
| 42 | GABARAPL1 | 1.76E−225 | 1.19057882 | 0.115 | 0.032 | 1.18E−221 | Higher in Autistic Samples | I |
| 43 | ATF3 | 1.56E−196 | 1.18212567 | 0.093 | 0.023 | 1.05E−192 | Higher in Autistic Samples | I |
| 44 | RFPL3S | 2.03E−61 | 1.16726779 | 0.024 | 0.004 | 1.36E−57 | Higher in Autistic Samples | I |
| 45 | CTD-2196E14.5 | 8.31E−136 | 1.1497306 | 0.062 | 0.015 | 5.57E−132 | Higher in Autistic Samples | I |
| 46 | RP11-496I9.1 | 3.11E−70 | 1.1490926 | 0.031 | 0.007 | 2.09E−66 | Higher in Autistic Samples | I |
| 47 | RP11-347D21.1 | 7.53E−59 | 1.14476166 | 0.022 | 0.004 | 5.05E−55 | Higher in Autistic Samples | I |
| 48 | TRMT5 | 6.30E−61 | 1.14311561 | 0.025 | 0.005 | 4.23E−57 | Higher in Autistic Samples | I |
| 49 | RP11-712B9.2 | 1.17E−55 | 1.14169429 | 0.02 | 0.003 | 7.83E−52 | Higher in Autistic Samples | I |
| 50 | CSTL1 | 3.48E−220 | 1.13989834 | 0.115 | 0.033 | 2.33E−216 | Higher in Autistic Samples | I |
| 51 | XXbac-BPG249D20.5 | 1.01E−43 | 1.13052803 | 0.011 | 0.001 | 6.76E−40 | Higher in Autistic Samples | I |
| 52 | RP11-669C19.1 | 2.91E−64 | 1.12245973 | 0.028 | 0.006 | 1.95E−60 | Higher in Autistic Samples | I |
| 53 | NRDE2 | 1.40E−59 | 1.1210956 | 0.024 | 0.005 | 9.36E−56 | Higher in Autistic Samples | I |
| 54 | MAPT-AS1 | 9.56E−49 | 1.11555659 | 0.019 | 0.004 | 6.41E−45 | Higher in Autistic Samples | I |
| 55 | EFCAB12 | 1.50E−176 | 1.11407129 | 0.093 | 0.026 | 1.01E−172 | Higher in Autistic Samples | I |
| 56 | VGLL3 | 1.12E−173 | 1.10526943 | 0.097 | 0.029 | 7.52E−170 | Higher in Autistic Samples | I |
| 57 | DCC | 6.97E−78 | 1.10476144 | 0.034 | 0.008 | 4.68E−74 | Higher in Autistic Samples | I |
| 58 | HSPB6 | 1.25E−274 | 1.10012731 | 0.148 | 0.043 | 8.37E−271 | Higher in Autistic Samples | I |
| 59 | S100A7A | 1.21E−56 | 1.09290423 | 0.025 | 0.005 | 8.09E−53 | Higher in Autistic Samples | I |
| 60 | CTD-2135D7.2 | 2.19E−98 | 1.09057325 | 0.051 | 0.014 | 1.47E−94 | Higher in Autistic Samples | I |
| 61 | KRT15 | 1.96E−63 | 1.08305757 | 0.032 | 0.008 | 1.31E−59 | Higher in Autistic Samples | I |
| 62 | RP11-403A21.3 | 7.62E−49 | 1.07058919 | 0.02 | 0.004 | 5.11E−45 | Higher in Autistic Samples | I |
| 63 | RP11-396C23.4 | 2.27E−45 | 1.06538973 | 0.018 | 0.004 | 1.52E−41 | Higher in Autistic Samples | I |
| 64 | C10orf90 | 1.32E−45 | 1.06530284 | 0.015 | 0.002 | 8.88E−42 | Higher in Autistic Samples | I |
| 65 | GMFG | 1.73E−43 | 1.06009029 | 0.017 | 0.003 | 1.16E−39 | Higher in Autistic Samples | I |
| 66 | KDM2B | 5.67E−108 | 1.05574061 | 0.058 | 0.017 | 3.80E−104 | Higher in Autistic Samples | I |
| 67 | TMSB4X | 1.94E−173 | 1.04997256 | 0.1 | 0.031 | 1.30E−169 | Higher in Autistic Samples | I |
| 68 | RP11-381K20.4 | 6.06E−44 | 1.04865813 | 0.016 | 0.003 | 4.06E−40 | Higher in Autistic Samples | I |
| 69 | OR2H1 | 1.14E−78 | 1.03963444 | 0.039 | 0.01 | 7.63E−75 | Higher in Autistic Samples | I |
| 70 | ZNF445 | 3.24E−47 | 1.03810017 | 0.024 | 0.006 | 2.17E−43 | Higher in Autistic Samples | I |
| 71 | TEPP | 7.57E−43 | 1.0318368 | 0.016 | 0.003 | 5.08E−39 | Higher in Autistic Samples | I |
| 72 | CTC-543D15.8 | 2.49E−77 | 1.03146247 | 0.038 | 0.01 | 1.67E−73 | Higher in Autistic Samples | I |
| 73 | CCDC155 | 5.62E−45 | 1.02388409 | 0.018 | 0.003 | 3.77E−41 | Higher in Autistic Samples | I |
| 74 | MAPK3 | 6.48E−70 | 1.02365775 | 0.04 | 0.012 | 4.34E−66 | Higher in Autistic Samples | I |
| 75 | RP5-1030M6.3 | 3.76E−37 | 1.0163131 | 0.013 | 0.002 | 2.52E−33 | Higher in Autistic Samples | I |
| 76 | SORCS3-AS1 | 2.91E−158 | 1.01615799 | 0.103 | 0.036 | 1.95E−154 | Higher in Autistic Samples | I |
| 77 | RP11-489E7.4 | 4.29E−67 | 1.01323687 | 0.033 | 0.009 | 2.88E−63 | Higher in Autistic Samples | I |
| 78 | AC007163.3 | 8.96E−64 | 1.00882926 | 0.03 | 0.007 | 6.01E−60 | Higher in Autistic Samples | I |
| 79 | XXyac-YX155B6.5 | 1.57E−56 | 1.00805736 | 0.027 | 0.007 | 1.05E−52 | Higher in Autistic Samples | I |
| 80 | TP53TG5 | 3.15E−39 | 1.00139654 | 0.013 | 0.002 | 2.11E−35 | Higher in Autistic Samples | I |
| 81 | C9orf3 | 2.21E−49 | 0.99088318 | 0.02 | 0.004 | 1.48E−45 | Higher in Autistic Samples | I |
| 82 | APOL6 | 4.37E−48 | 0.98945229 | 0.02 | 0.004 | 2.93E−44 | Higher in Autistic Samples | I |
| 83 | ARL4C | 9.68E−61 | 0.98894839 | 0.031 | 0.008 | 6.49E−57 | Higher in Autistic Samples | I |
| 84 | AC093627.10 | 1.04E−49 | 0.98827207 | 0.023 | 0.005 | 7.00E−46 | Higher in Autistic Samples | I |
| 85 | SERPINB6 | 5.59E−50 | 0.98712056 | 0.021 | 0.005 | 3.75E−46 | Higher in Autistic Samples | I |
| 86 | PIBF1 | 2.86E−41 | 0.98657936 | 0.018 | 0.004 | 1.92E−37 | Higher in Autistic Samples | I |
| 87 | CDK19 | 7.25E−46 | 0.98642127 | 0.024 | 0.006 | 4.86E−42 | Higher in Autistic Samples | I |
| 88 | RBBP6 | 2.96E−45 | 0.98026907 | 0.025 | 0.008 | 1.98E−41 | Higher in Autistic Samples | I |
| 89 | RP11-140K17.3 | 7.75E−135 | 0.97751947 | 0.081 | 0.026 | 5.20E−131 | Higher in Autistic Samples | I |
| 90 | EAF1 | 3.87E−81 | 0.9748147 | 0.044 | 0.013 | 2.59E−77 | Higher in Autistic Samples | I |
| 91 | GLRX2 | 1.28E−244 | 0.97392993 | 0.172 | 0.064 | 8.57E−241 | Higher in Autistic Samples | I |
| 92 | RP11-557J10.5 | 1.59E−48 | 0.96371754 | 0.025 | 0.007 | 1.07E−44 | Higher in Autistic Samples | I |
| 93 | DAG1 | 0 | 0.95875727 | 0.212 | 0.077 | 0 | Higher in Autistic Samples | I |
| 94 | RP11-96K19.5 | 1.98E−68 | 0.95577436 | 0.041 | 0.013 | 1.33E−64 | Higher in Autistic Samples | I |
| 95 | WDR20 | 4.28E−126 | 0.95518325 | 0.088 | 0.031 | 2.87E−122 | Higher in Autistic Samples | I |
| 96 | AC093818.1 | 2.00E−46 | 0.94682842 | 0.024 | 0.007 | 1.34E−42 | Higher in Autistic Samples | I |
| 97 | NECAP2 | 2.16E−58 | 0.9446339 | 0.032 | 0.009 | 1.45E−54 | Higher in Autistic Samples | I |

TABLE 2-continued

Tier 1 genes (ranked by Average log Fold Change (avg_logFC)).

| | GeneName | p_val | avg_logFC | pct.1 | pct.2 | p_val_adj | Marker Type | Tier |
|---|---|---|---|---|---|---|---|---|
| 98 | RP11-375N15.2 | 2.49E-43 | 0.93688248 | 0.019 | 0.005 | 1.67E-39 | Higher in Autistic Samples | I |
| 99 | DHDDS | 2.40E-94 | 0.93475774 | 0.06 | 0.02 | 1.61E-90 | Higher in Autistic Samples | I |
| 100 | LRRC52 | 4.38E-118 | 0.93256198 | 0.076 | 0.025 | 2.93E-114 | Higher in Autistic Samples | I |
| 101 | WTIP | 3.02E-44 | 0.93227058 | 0.021 | 0.005 | 2.02E-40 | Higher in Autistic Samples | I |
| 102 | TNKS | 5.32E-36 | 0.93128563 | 0.016 | 0.004 | 3.57E-32 | Higher in Autistic Samples | I |
| 103 | CFAP157 | 4.59E-68 | 0.93025919 | 0.039 | 0.012 | 3.08E-64 | Higher in Autistic Samples | I |
| 104 | COX8C | 1.85E-71 | 0.92895792 | 0.046 | 0.015 | 1.24E-67 | Higher in Autistic Samples | I |
| 105 | XPNPEP3 | 4.17E-43 | 0.92804404 | 0.021 | 0.006 | 2.79E-39 | Higher in Autistic Samples | I |
| 106 | NOLC1 | 7.90E-30 | 0.92085538 | 0.011 | 0.002 | 5.29E-26 | Higher in Autistic Samples | I |
| 107 | RARA-AS1 | 1.10E-37 | 0.91771325 | 0.016 | 0.003 | 7.38E-34 | Higher in Autistic Samples | I |
| 108 | RP4-625H18.2 | 1.67E-46 | 0.91287331 | 0.025 | 0.007 | 1.12E-42 | Higher in Autistic Samples | I |
| 109 | FANK1 | 2.16E-43 | 0.90825249 | 0.025 | 0.007 | 1.45E-39 | Higher in Autistic Samples | I |
| 110 | PPP2R1B | 4.51E-32 | 0.90629363 | 0.013 | 0.003 | 3.02E-28 | Higher in Autistic Samples | I |
| 111 | RP11-168K9.1 | 1.71E-71 | 0.90317287 | 0.043 | 0.013 | 1.14E-67 | Higher in Autistic Samples | I |
| 112 | MIR762HG | 4.94E-226 | 0.89464445 | 0.171 | 0.066 | 3.31E-222 | Higher in Autistic Samples | I |
| 113 | RP11-315I20.1 | 9.52E-74 | 0.81224041 | 0.057 | 0.022 | 6.38E-70 | Higher in Autistic Samples | I |
| 114 | TADA2A | 3.27E-90 | 0.74340972 | 0.078 | 0.032 | 2.19E-86 | Higher in Autistic Samples | I |
| 115 | MEST | 8.32E-68 | 0.71354339 | 0.063 | 0.027 | 5.58E-64 | Higher in Autistic Samples | I |
| 116 | RP11-480I12.10 | 3.78E-59 | 0.68708428 | 0.053 | 0.022 | 2.54E-55 | Higher in Autistic Samples | I |
| 117 | TMCO2 | 2.87E-71 | 0.67872596 | 0.088 | 0.044 | 1.92E-67 | Higher in Autistic Samples | I |
| 118 | ZFP36L1 | 2.05E-74 | 0.67610838 | 0.081 | 0.037 | 1.37E-70 | Higher in Autistic Samples | I |
| 119 | ATP1B3 | 1.83E-173 | 0.64339015 | 0.221 | 0.114 | 1.23E-169 | Higher in Autistic Samples | I |
| 120 | CRAMP1 | 1.19E-67 | 0.60669297 | 0.081 | 0.039 | 7.96E-64 | Higher in Autistic Samples | I |
| 121 | SPTY2D1-AS1 | 1.38E-92 | 0.59500785 | 0.156 | 0.09 | 9.25E-89 | Higher in Autistic Samples | I |
| 122 | TNP1 | 5.14E-125 | 0.59133532 | 0.199 | 0.112 | 3.44E-121 | Higher in Autistic Samples | I |
| 123 | AC007557.1 | 3.02E-99 | 0.59123502 | 0.153 | 0.084 | 2.02E-95 | Higher in Autistic Samples | I |
| 124 | ACAP1 | 3.36E-31 | 0.57124888 | 0.051 | 0.028 | 2.25E-27 | Higher in Autistic Samples | I |
| 125 | MARCKS | 7.66E-77 | 0.52885638 | 0.127 | 0.071 | 5.13E-73 | Higher in Autistic Samples | I |
| 126 | CTD-2568A17.1 | 1.85E-40 | 0.35883504 | 0.175 | 0.128 | 1.24E-36 | Higher in Autistic Samples | I |
| 127 | PRM1 | 5.95E-194 | 0.3057173 | 0.665 | 0.537 | 3.99E-190 | Higher in Autistic Samples | I |
| 128 | TCEB2 | 5.52E-14 | 0.27295501 | 0.066 | 0.048 | 3.70E-10 | Higher in Autistic Samples | I |
| 129 | TMEM31 | 6.82E-06 | 0.17468959 | 0.064 | 0.053 | 0.04572819 | Higher in Autistic Samples | I |
| 130 | PHOSPHO1 | 8.73E-08 | -0.19081991 | 0.096 | 0.112 | 0.00058503 | Higher in Normal/Healthy Samples | I |
| 131 | ETNK2 | 5.40E-08 | -0.1960796 | 0.054 | 0.067 | 0.00036225 | Higher in Normal/Healthy Samples | I |
| 132 | C17orf74 | 1.83E-09 | -0.21237853 | 0.074 | 0.091 | 1.23E-05 | Higher in Normal/Healthy Samples | I |
| 133 | DGCR6L | 2.33E-13 | -0.21246435 | 0.139 | 0.165 | 1.56E-09 | Higher in Normal/Healthy Samples | I |
| 134 | ODF3L2 | 2.70E-09 | -0.24128677 | 0.066 | 0.082 | 1.81E-05 | Higher in Normal/Healthy Samples | I |
| 135 | CIB1 | 1.28E-12 | -0.24246239 | 0.075 | 0.095 | 8.59E-09 | Higher in Normal/Healthy Samples | I |
| 136 | NUPR2 | 4.93E-94 | -0.32594691 | 0.349 | 0.44 | 3.31E-90 | Higher in Normal/Healthy Samples | I |
| 137 | C16orf82 | 5.81E-32 | -0.3277931 | 0.089 | 0.127 | 3.89E-28 | Higher in Normal/Healthy Samples | I |
| 138 | UBXN6 | 1.51E-14 | -0.3307218 | 0.047 | 0.065 | 1.01E-10 | Higher in Normal/Healthy Samples | I |
| 139 | DNAJC4 | 7.46E-54 | -0.34251473 | 0.213 | 0.275 | 5.00E-50 | Higher in Normal/Healthy Samples | I |
| 140 | UBA52 | 1.65E-26 | -0.36757107 | 0.082 | 0.114 | 1.11E-22 | Higher in Normal/Healthy Samples | I |
| 141 | REEP6 | 6.29E-35 | -0.4119588 | 0.082 | 0.12 | 4.22E-31 | Higher in Normal/Healthy Samples | I |
| 142 | LELP1 | 2.83E-64 | -0.41891807 | 0.137 | 0.202 | 1.90E-60 | Higher in Normal/Healthy Samples | I |
| 143 | RANGAP1 | 9.28E-27 | -0.43269108 | 0.051 | 0.078 | 6.22E-23 | Higher in Normal/Healthy Samples | I |
| 144 | TNFAIP8L1 | 2.02E-20 | -0.44160621 | 0.035 | 0.055 | 1.36E-16 | Higher in Normal/Healthy Samples | I |
| 145 | ARL4A | 3.24E-46 | -0.45607688 | 0.047 | 0.084 | 2.17E-42 | Higher in Normal/Healthy Samples | I |
| 146 | PRM2 | 0 | -0.47146124 | 0.771 | 0.888 | 0 | Higher in Normal/Healthy Samples | I |
| 147 | TPGS2 | 1.19E-31 | -0.4824332 | 0.043 | 0.071 | 7.96E-28 | Higher in Normal/Healthy Samples | I |
| 148 | CSNK1G2 | 2.54E-30 | -0.50314872 | 0.036 | 0.062 | 1.70E-26 | Higher in Normal/Healthy Samples | I |
| 149 | LPIN1 | 2.29E-32 | -0.50601869 | 0.03 | 0.055 | 1.54E-28 | Higher in Normal/Healthy Samples | I |
| 150 | ZNHIT2 | 2.10E-26 | -0.50875957 | 0.034 | 0.057 | 1.41E-22 | Higher in Normal/Healthy Samples | I |
| 151 | PCSK4 | 8.83E-38 | -0.50900876 | 0.058 | 0.093 | 5.92E-34 | Higher in Normal/Healthy Samples | I |
| 152 | PCYT2 | 4.06E-78 | -0.51326763 | 0.116 | 0.183 | 2.72E-74 | Higher in Normal/Healthy Samples | I |
| 153 | OAZ3 | 7.74E-32 | -0.53203866 | 0.029 | 0.053 | 5.19E-28 | Higher in Normal/Healthy Samples | I |
| 154 | TPPP2 | 2.04E-40 | -0.5489612 | 0.038 | 0.069 | 1.37E-36 | Higher in Normal/Healthy Samples | I |
| 155 | SMCP | 4.80E-251 | -0.55900819 | 0.319 | 0.469 | 3.22E-247 | Higher in Normal/Healthy Samples | I |
| 156 | FBXW5 | 3.86E-62 | -0.56068959 | 0.073 | 0.123 | 2.59E-58 | Higher in Normal/Healthy Samples | I |
| 157 | TCP11 | 5.93E-53 | -0.56545781 | 0.046 | 0.085 | 3.97E-49 | Higher in Normal/Healthy Samples | I |
| 158 | BOD1L2 | 2.80E-75 | -0.56946859 | 0.064 | 0.119 | 1.88E-71 | Higher in Normal/Healthy Samples | I |
| 159 | CARHSP1 | 5.92E-119 | -0.58931111 | 0.126 | 0.214 | 3.97E-115 | Higher in Normal/Healthy Samples | I |
| 160 | GLUL | 2.99E-103 | -0.63251552 | 0.088 | 0.161 | 2.01E-99 | Higher in Normal/Healthy Samples | I |
| 161 | C2orf57 | 3.94E-43 | -0.64003804 | 0.03 | 0.06 | 2.64E-39 | Higher in Normal/Healthy Samples | I |
| 162 | SMKR1 | 5.78E-97 | -0.65230975 | 0.06 | 0.122 | 3.88E-93 | Higher in Normal/Healthy Samples | I |
| 163 | PTP4A1 | 1.21E-72 | -0.65925521 | 0.048 | 0.097 | 8.11E-69 | Higher in Normal/Healthy Samples | I |
| 164 | CCSER2 | 3.15E-48 | -0.65930973 | 0.024 | 0.054 | 2.11E-44 | Higher in Normal/Healthy Samples | I |
| 165 | AQP5 | 3.83E-69 | -0.67280678 | 0.049 | 0.095 | 2.57E-65 | Higher in Normal/Healthy Samples | I |
| 166 | MPC2 | 2.68E-63 | -0.67943352 | 0.036 | 0.075 | 1.80E-59 | Higher in Normal/Healthy Samples | I |
| 167 | RGS22 | 3.68E-67 | -0.67970344 | 0.039 | 0.081 | 2.47E-63 | Higher in Normal/Healthy Samples | I |
| 168 | PKM | 2.27E-48 | -0.69167852 | 0.032 | 0.064 | 1.52E-44 | Higher in Normal/Healthy Samples | I |
| 169 | MOSPD3 | 2.41E-63 | -0.69992461 | 0.046 | 0.089 | 1.61E-59 | Higher in Normal/Healthy Samples | I |
| 170 | CCDC136 | 1.36E-35 | -0.70078715 | 0.015 | 0.035 | 9.09E-32 | Higher in Normal/Healthy Samples | I |
| 171 | AC012370.3 | 4.76E-16 | -0.70120883 | 0.004 | 0.011 | 3.19E-12 | Higher in Normal/Healthy Samples | I |
| 172 | VTI1B | 1.08E-25 | -0.70305115 | 0.009 | 0.022 | 7.25E-22 | Higher in Normal/Healthy Samples | I |
| 173 | INCA1 | 4.98E-18 | -0.70556214 | 0.005 | 0.013 | 3.34E-14 | Higher in Normal/Healthy Samples | I |

TABLE 2-continued

Tier 1 genes (ranked by Average log Fold Change (avg_logFC)).

| | GeneName | p_val | avg_logFC | pct.1 | pct.2 | p_val_adj | Marker Type | Tier |
|---|---|---|---|---|---|---|---|---|
| 174 | SPATC1L | 4.09E−20 | −0.7105641 | 0.009 | 0.021 | 2.74E−16 | Higher in Normal/Healthy Samples | I |
| 175 | CXCL16 | 4.34E−102 | −0.71432249 | 0.068 | 0.134 | 2.91E−98 | Higher in Normal/Healthy Samples | I |
| 176 | METAP1 | 2.31E−42 | −0.7150351 | 0.019 | 0.044 | 1.55E−38 | Higher in Normal/Healthy Samples | I |
| 177 | USP25 | 6.00E−37 | −0.71630367 | 0.014 | 0.034 | 4.03E−33 | Higher in Normal/Healthy Samples | I |
| 178 | SH3GL3 | 5.39E−64 | −0.71853478 | 0.033 | 0.072 | 3.61E−60 | Higher in Normal/Healthy Samples | I |
| 179 | MAP2K2 | 1.24E−36 | −0.71938501 | 0.019 | 0.042 | 8.29E−33 | Higher in Normal/Healthy Samples | I |
| 180 | CRAT | 9.90E−37 | −0.71965925 | 0.02 | 0.042 | 6.64E−33 | Higher in Normal/Healthy Samples | I |
| 181 | RPS27A | 4.81E−15 | −0.71969121 | 0.005 | 0.012 | 3.23E−11 | Higher in Normal/Healthy Samples | I |
| 182 | RPL29 | 9.78E−16 | −0.72187685 | 0.005 | 0.013 | 6.56E−12 | Higher in Normal/Healthy Samples | I |
| 183 | RPL13 | 2.93E−44 | −0.73196118 | 0.025 | 0.053 | 1.96E−40 | Higher in Normal/Healthy Samples | I |
| 184 | ANKRD12 | 1.23E−19 | −0.73264099 | 0.003 | 0.011 | 8.27E−16 | Higher in Normal/Healthy Samples | I |
| 185 | TUBB4B | 6.30E−21 | −0.73989247 | 0.007 | 0.017 | 4.23E−17 | Higher in Normal/Healthy Samples | I |
| 186 | NRAV | 1.55E−22 | −0.74189508 | 0.006 | 0.016 | 1.04E−18 | Higher in Normal/Healthy Samples | I |
| 187 | FAM220A | 6.62E−38 | −0.74267453 | 0.016 | 0.037 | 4.44E−34 | Higher in Normal/Healthy Samples | I |
| 188 | FXR1 | 2.40E−33 | −0.74665403 | 0.012 | 0.029 | 1.61E−29 | Higher in Normal/Healthy Samples | I |
| 189 | BSG | 1.41E−30 | −0.75021813 | 0.012 | 0.029 | 9.45E−27 | Higher in Normal/Healthy Samples | I |
| 190 | TSPAN6 | 1.85E−148 | −0.75052612 | 0.076 | 0.163 | 1.24E−144 | Higher in Normal/Healthy Samples | I |
| 191 | RPL12 | 8.53E−23 | −0.75161566 | 0.006 | 0.016 | 5.72E−19 | Higher in Normal/Healthy Samples | I |
| 192 | PWRN1 | 2.39E−27 | −0.75658483 | 0.007 | 0.02 | 1.60E−23 | Higher in Normal/Healthy Samples | I |
| 193 | SRP54 | 1.22E−36 | −0.75928469 | 0.011 | 0.03 | 8.20E−33 | Higher in Normal/Healthy Samples | I |
| 194 | CCNY | 7.18E−98 | −0.7594678 | 0.045 | 0.101 | 4.82E−94 | Higher in Normal/Healthy Samples | I |
| 195 | PVRL3 | 7.41E−19 | −0.76309265 | 0.004 | 0.013 | 4.96E−15 | Higher in Normal/Healthy Samples | I |
| 196 | BPIFA3 | 2.52E−44 | −0.76545175 | 0.017 | 0.041 | 1.69E−40 | Higher in Normal/Healthy Samples | I |
| 197 | PTOV1 | 1.26E−41 | −0.76745999 | 0.018 | 0.042 | 8.42E−38 | Higher in Normal/Healthy Samples | I |
| 198 | ADO | 9.27E−30 | −0.77367563 | 0.008 | 0.022 | 6.22E−26 | Higher in Normal/Healthy Samples | I |
| 199 | NSUN4 | 1.41E−39 | −0.7738613 | 0.015 | 0.036 | 9.42E−36 | Higher in Normal/Healthy Samples | I |
| 200 | SRPK2 | 7.52E−44 | −0.77780582 | 0.014 | 0.037 | 5.04E−40 | Higher in Normal/Healthy Samples | I |
| 201 | RIOK3 | 4.81E−24 | −0.77797707 | 0.004 | 0.013 | 3.22E−20 | Higher in Normal/Healthy Samples | I |
| 202 | SPCS1 | 5.94E−27 | −0.78165814 | 0.006 | 0.018 | 3.98E−23 | Higher in Normal/Healthy Samples | I |
| 203 | GPR137 | 1.83E−46 | −0.78390659 | 0.019 | 0.045 | 1.23E−42 | Higher in Normal/Healthy Samples | I |
| 204 | UBE2N | 2.69E−51 | −0.78786144 | 0.017 | 0.044 | 1.81E−47 | Higher in Normal/Healthy Samples | I |
| 205 | RPL8 | 2.53E−23 | −0.79006755 | 0.008 | 0.02 | 1.69E−19 | Higher in Normal/Healthy Samples | I |
| 206 | WASF1 | 3.64E−47 | −0.79208478 | 0.016 | 0.041 | 2.44E−43 | Higher in Normal/Healthy Samples | I |
| 207 | FUNDC2 | 1.26E−32 | −0.79518607 | 0.008 | 0.024 | 8.45E−29 | Higher in Normal/Healthy Samples | I |
| 208 | HDLBP | 2.47E−28 | −0.79814225 | 0.007 | 0.02 | 1.66E−24 | Higher in Normal/Healthy Samples | I |
| 209 | SPTBN2 | 9.32E−23 | −0.8011329 | 0.006 | 0.017 | 6.25E−19 | Higher in Normal/Healthy Samples | I |
| 210 | SLFNL1 | 5.80E−47 | −0.80387147 | 0.019 | 0.045 | 3.89E−43 | Higher in Normal/Healthy Samples | I |
| 211 | GSG1 | 1.20E−30 | −0.8052964 | 0.008 | 0.022 | 8.02E−27 | Higher in Normal/Healthy Samples | I |
| 212 | NT5C1B | 7.18E−24 | −0.80575973 | 0.003 | 0.012 | 4.82E−20 | Higher in Normal/Healthy Samples | I |
| 213 | PPP2R5A | 1.89E−30 | −0.80771337 | 0.006 | 0.02 | 1.27E−26 | Higher in Normal/Healthy Samples | I |
| 214 | PHKG2 | 4.02E−32 | −0.80805201 | 0.011 | 0.028 | 2.70E−28 | Higher in Normal/Healthy Samples | I |
| 215 | PROCA1 | 4.03E−122 | −0.81825215 | 0.054 | 0.123 | 2.70E−118 | Higher in Normal/Healthy Samples | I |
| 216 | INPP5K | 1.75E−20 | −0.82107041 | 0.003 | 0.012 | 1.17E−16 | Higher in Normal/Healthy Samples | I |
| 217 | PDZD8 | 4.06E−44 | −0.821542 | 0.013 | 0.035 | 2.72E−40 | Higher in Normal/Healthy Samples | I |
| 218 | ABHD1 | 8.50E−90 | −0.82702038 | 0.041 | 0.092 | 5.70E−86 | Higher in Normal/Healthy Samples | I |
| 219 | SLAIN2 | 9.84E−29 | −0.83224107 | 0.004 | 0.016 | 6.60E−25 | Higher in Normal/Healthy Samples | I |
| 220 | SPATA3 | 5.73E−53 | −0.83684109 | 0.017 | 0.045 | 3.84E−49 | Higher in Normal/Healthy Samples | I |
| 221 | TSSK6 | 0 | −0.83965111 | 0.258 | 0.471 | 0 | Higher in Normal/Healthy Samples | I |
| 222 | UBE2D2 | 5.05E−24 | −0.84183562 | 0.003 | 0.012 | 3.39E−20 | Higher in Normal/Healthy Samples | I |
| 223 | PRC1-AS1 | 3.65E−25 | −0.84456348 | 0.003 | 0.012 | 2.44E−21 | Higher in Normal/Healthy Samples | I |
| 224 | VWA3B | 3.73E−30 | −0.86101318 | 0.005 | 0.017 | 2.50E−26 | Higher in Normal/Healthy Samples | I |
| 225 | HSPA4L | 3.49E−57 | −0.86880782 | 0.015 | 0.042 | 2.34E−53 | Higher in Normal/Healthy Samples | I |
| 226 | FKBP8 | 9.32E−73 | −0.86979184 | 0.024 | 0.061 | 6.25E−69 | Higher in Normal/Healthy Samples | I |
| 227 | MFF | 2.67E−86 | −0.88041252 | 0.028 | 0.073 | 1.79E−82 | Higher in Normal/Healthy Samples | I |
| 228 | LINC00901 | 7.63E−27 | −0.8912922 | 0.003 | 0.014 | 5.12E−23 | Higher in Normal/Healthy Samples | I |
| 229 | GNAS | 2.74E−80 | −0.89525422 | 0.026 | 0.067 | 1.84E−76 | Higher in Normal/Healthy Samples | I |
| 230 | RNF138 | 2.66E−58 | −0.9007048 | 0.014 | 0.041 | 1.79E−54 | Higher in Normal/Healthy Samples | I |
| 231 | CABYR | 3.41E−57 | −0.90725229 | 0.013 | 0.039 | 2.29E−53 | Higher in Normal/Healthy Samples | I |
| 232 | TSSK1B | 1.39E−46 | −0.91245516 | 0.01 | 0.032 | 9.30E−43 | Higher in Normal/Healthy Samples | I |
| 233 | TSSK2 | 3.88E−100 | −0.92353024 | 0.032 | 0.083 | 2.60E−96 | Higher in Normal/Healthy Samples | I |
| 234 | SPATA18 | 6.37E−75 | −0.92454626 | 0.018 | 0.053 | 4.27E−71 | Higher in Normal/Healthy Samples | I |
| 235 | RPS18 | 5.80E−26 | −0.93014933 | 0.003 | 0.013 | 3.89E−22 | Higher in Normal/Healthy Samples | I |
| 236 | SLC38A7 | 1.42E−65 | −0.95784225 | 0.016 | 0.047 | 9.49E−62 | Higher in Normal/Healthy Samples | I |
| 237 | TPD52L3 | 2.32E−64 | −0.97302049 | 0.015 | 0.044 | 1.55E−60 | Higher in Normal/Healthy Samples | I |
| 238 | ACSBG2 | 5.23E−89 | −0.97438147 | 0.019 | 0.06 | 3.51E−85 | Higher in Normal/Healthy Samples | I |
| 239 | RP11-14J7.7 | 2.82E−28 | −0.97832614 | 0.002 | 0.011 | 1.89E−24 | Higher in Normal/Healthy Samples | I |
| 240 | RPLP1 | 6.85E−29 | −0.9889916 | 0.002 | 0.011 | 4.59E−25 | Higher in Normal/Healthy Samples | I |
| 241 | TPP2 | 5.72E−38 | −0.99773959 | 0.004 | 0.018 | 3.84E−34 | Higher in Normal/Healthy Samples | I |
| 242 | PSMD6 | 4.91E−51 | −1.00758998 | 0.01 | 0.033 | 3.29E−47 | Higher in Normal/Healthy Samples | I |
| 243 | PAFAH1B1 | 5.55E−97 | −1.00866807 | 0.019 | 0.062 | 3.72E−93 | Higher in Normal/Healthy Samples | I |
| 244 | UBA5 | 1.06E−33 | −1.02551362 | 0.002 | 0.013 | 7.13E−30 | Higher in Normal/Healthy Samples | I |
| 245 | RPL37A | 2.13E−31 | −1.03668382 | 0.002 | 0.012 | 1.43E−27 | Higher in Normal/Healthy Samples | I |
| 246 | GAPDH | 1.66E−111 | −1.05561606 | 0.025 | 0.076 | 1.11E−107 | Higher in Normal/Healthy Samples | I |
| 247 | RPS8 | 1.99E−32 | −1.07601884 | 0.001 | 0.011 | 1.34E−28 | Higher in Normal/Healthy Samples | I |
| 248 | C17orf97 | 2.80E−42 | −1.07626006 | 0.004 | 0.019 | 1.88E−38 | Higher in Normal/Healthy Samples | I |
| 249 | CCDC91 | 8.92E−184 | −1.11278663 | 0.034 | 0.113 | 5.98E−180 | Higher in Normal/Healthy Samples | I |

TABLE 2-continued

Tier 1 genes (ranked by Average log Fold Change (avg_logFC)).

| | GeneName | p_val | avg_logFC | pct.1 | pct.2 | p_val_adj | Marker Type | Tier |
|---|---|---|---|---|---|---|---|---|
| 250 | SEC14L1 | 1.72E−44 | −1.12671924 | 0.004 | 0.02 | 1.16E−40 | Higher in Normal/Healthy Samples | I |
| 251 | MTFR1L | 1.72E−38 | −1.13493473 | 0.002 | 0.015 | 1.15E−34 | Higher in Normal/Healthy Samples | I |
| 252 | DCUN1D1 | 1.14E−304 | −1.14363712 | 0.055 | 0.18 | 7.63E−301 | Higher in Normal/Healthy Samples | I |
| 253 | RAB1A | 2.06E−71 | −1.16077628 | 0.008 | 0.035 | 1.38E−67 | Higher in Normal/Healthy Samples | I |
| 254 | CRISP2 | 0 | −1.16278049 | 0.237 | 0.598 | 0 | Higher in Normal/Healthy Samples | I |
| 255 | RPS6 | 3.58E−55 | −1.18916375 | 0.005 | 0.025 | 2.40E−51 | Higher in Normal/Healthy Samples | I |
| 256 | PGK2 | 1.44E−66 | −1.19637517 | 0.007 | 0.031 | 9.68E−63 | Higher in Normal/Healthy Samples | I |
| 257 | VRK3 | 1.54E−113 | −1.19897607 | 0.017 | 0.064 | 1.03E−109 | Higher in Normal/Healthy Samples | I |
| 258 | BAZ1A | 7.59E−55 | −1.21881058 | 0.004 | 0.023 | 5.09E−51 | Higher in Normal/Healthy Samples | I |
| 259 | TPT1 | 1.66E−41 | −1.22666545 | 0.002 | 0.014 | 1.11E−37 | Higher in Normal/Healthy Samples | I |
| 260 | AKAP1 | 2.70E−126 | −1.23200407 | 0.018 | 0.068 | 1.81E−122 | Higher in Normal/Healthy Samples | I |
| 261 | MS4A14 | 4.48E−81 | −1.30521052 | 0.006 | 0.033 | 3.00E−77 | Higher in Normal/Healthy Samples | I |
| 262 | CCDC7 | 1.92E−62 | −1.38123071 | 0.003 | 0.022 | 1.29E−58 | Higher in Normal/Healthy Samples | I |
| 263 | SEMG1 | 5.93E−43 | −1.41266698 | 0 | 0.011 | 3.98E−39 | Higher in Normal/Healthy Samples | I |
| 264 | SARAF | 1.67E−100 | −1.43075908 | 0.008 | 0.042 | 1.12E−96 | Higher in Normal/Healthy Samples | I |
| 265 | RPL13A | 9.71E−54 | −1.46902294 | 0.001 | 0.017 | 6.51E−50 | Higher in Normal/Healthy Samples | I |
| 266 | FTH1 | 6.83E−69 | −1.46908693 | 0.002 | 0.023 | 4.58E−65 | Higher in Normal/Healthy Samples | I |
| 267 | CUL3 | 1.76E−78 | −1.48330996 | 0.003 | 0.027 | 1.18E−74 | Higher in Normal/Healthy Samples | I |
| 268 | POLR1D | 2.19E−81 | −1.51690954 | 0.004 | 0.029 | 1.47E−77 | Higher in Normal/Healthy Samples | I |
| 269 | MT-CO2 | 2.20E−54 | −1.57181674 | 0 | 0.013 | 1.48E−50 | Higher in Normal/Healthy Samples | I |
| 270 | FSCB | 2.53E−100 | −1.65854764 | 0.003 | 0.033 | 1.69E−96 | Higher in Normal/Healthy Samples | I |
| 271 | RPS4X | 1.64E−62 | −1.70057668 | 0 | 0.016 | 1.10E−58 | Higher in Normal/Healthy Samples | I |
| 272 | CLU | 1.88E−91 | −1.7436342 | 0.003 | 0.031 | 1.26E−87 | Higher in Normal/Healthy Samples | I |
| 273 | RPL3 | 3.79E−86 | −1.78533752 | 0.001 | 0.025 | 2.54E−82 | Higher in Normal/Healthy Samples | I |
| 274 | PLBD2 | 1.20E−121 | −1.92666971 | 0.002 | 0.035 | 8.02E−118 | Higher in Normal/Healthy Samples | I |
| 275 | RPL10 | 7.64E−89 | −1.98552753 | 0 | 0.022 | 5.12E−85 | Higher in Normal/Healthy Samples | I |
| 276 | ARL6IP4 | 7.74E−14 | 0.44815827 | 0.017 | 0.009 | 5.19E−10 | Higher in Autistic Samples | I |
| 277 | AACS | 3.43E−24 | 0.79826845 | 0.011 | 0.003 | 2.30E−20 | Higher in Autistic Samples | I |
| 278 | RSRC2 | 1.31E−12 | 0.54803385 | 0.015 | 0.008 | 8.78E−09 | Higher in Autistic Samples | I |
| 279 | ZCCHC8 | 3.48E−18 | 0.63398565 | 0.013 | 0.005 | 2.34E−14 | Higher in Autistic Samples | I | p_val = p value;
pct.1 = percent of cells in autism sample
pct.2 = percent of cells in normal sample

TABLE 3

Tier 2 genes (ranked by Average log Fold Change (avg_logFC)).

| | GeneName | p_val | avg_logFC | pct.1 | pct.2 | p_val_adj | Marker Type | Tier |
|---|---|---|---|---|---|---|---|---|
| 1 | CTD-2363C16.1 | 7.13E−36 | 0.897974131 | 0.014 | 0.003 | 4.78E−32 | Higher in Autistic Samples | II |
| 2 | KLHL12 | 2.55E−40 | 0.896768124 | 0.016 | 0.003 | 1.71E−36 | Higher in Autistic Samples | II |
| 3 | CEP152 | 4.04E−42 | 0.895887735 | 0.021 | 0.006 | 2.71E−38 | Higher in Autistic Samples | II |
| 4 | RP11-295M18.6 | 6.20E−43 | 0.891397527 | 0.023 | 0.007 | 4.16E−39 | Higher in Autistic Samples | II |
| 5 | AC084219.4 | 2.51E−45 | 0.891304579 | 0.025 | 0.008 | 1.68E−41 | Higher in Autistic Samples | II |
| 6 | HDAC4 | 2.20E−57 | 0.887589768 | 0.037 | 0.012 | 1.47E−53 | Higher in Autistic Samples | II |
| 7 | DPP3 | 7.10E−36 | 0.875382514 | 0.018 | 0.005 | 4.76E−32 | Higher in Autistic Samples | II |
| 8 | OVOS2 | 4.01E−31 | 0.866161766 | 0.017 | 0.005 | 2.69E−27 | Higher in Autistic Samples | II |
| 9 | MAMDC2-AS1 | 1.06E−35 | 0.866066761 | 0.02 | 0.006 | 7.08E−32 | Higher in Autistic Samples | II |
| 10 | FAM186A | 8.76E−29 | 0.866027722 | 0.015 | 0.004 | 5.87E−25 | Higher in Autistic Samples | II |
| 11 | ACSS1 | 4.48E−63 | 0.864268459 | 0.039 | 0.013 | 3.00E−59 | Higher in Autistic Samples | II |
| 12 | CDIP1 | 8.76E−30 | 0.864075806 | 0.018 | 0.006 | 5.87E−26 | Higher in Autistic Samples | II |
| 13 | INPP5B | 2.10E−34 | 0.862542598 | 0.014 | 0.003 | 1.41E−30 | Higher in Autistic Samples | II |
| 14 | PPP1R12B | 8.15E−45 | 0.857301514 | 0.026 | 0.008 | 5.46E−41 | Higher in Autistic Samples | II |
| 15 | RP11-527L4.6 | 5.88E−32 | 0.856949468 | 0.013 | 0.003 | 3.94E−28 | Higher in Autistic Samples | II |
| 16 | ATP6V1A | 2.99E−50 | 0.855388822 | 0.035 | 0.013 | 2.01E−46 | Higher in Autistic Samples | II |
| 17 | EFCAB11 | 3.60E−28 | 0.852818632 | 0.013 | 0.003 | 2.42E−24 | Higher in Autistic Samples | II |
| 18 | VN1R2 | 1.28E−29 | 0.852378352 | 0.016 | 0.005 | 8.60E−26 | Higher in Autistic Samples | II |
| 19 | FAM179A | 6.82E−42 | 0.851964548 | 0.021 | 0.005 | 4.57E−38 | Higher in Autistic Samples | II |
| 20 | PELP1 | 4.77E−28 | 0.848646069 | 0.014 | 0.004 | 3.20E−24 | Higher in Autistic Samples | II |
| 21 | STOML2 | 1.68E−30 | 0.845106236 | 0.017 | 0.005 | 1.13E−26 | Higher in Autistic Samples | II |
| 22 | PCOLCE-AS1 | 3.72E−61 | 0.843571125 | 0.044 | 0.016 | 2.50E−57 | Higher in Autistic Samples | II |
| 23 | AC004490.1 | 4.00E−61 | 0.840446864 | 0.045 | 0.016 | 2.68E−57 | Higher in Autistic Samples | II |
| 24 | EVX2 | 1.63E−38 | 0.839364873 | 0.02 | 0.006 | 1.09E−34 | Higher in Autistic Samples | II |
| 25 | RP11-258F1.1 | 3.28E−31 | 0.835456577 | 0.015 | 0.004 | 2.20E−27 | Higher in Autistic Samples | II |
| 26 | CDKN1C | 3.70E−25 | 0.834553258 | 0.011 | 0.003 | 2.48E−21 | Higher in Autistic Samples | II |
| 27 | RP5-971N18.3 | 4.33E−37 | 0.830688886 | 0.022 | 0.007 | 2.90E−33 | Higher in Autistic Samples | II |
| 28 | LAPTM4A | 3.07E−61 | 0.830515303 | 0.045 | 0.016 | 2.06E−57 | Higher in Autistic Samples | II |
| 29 | RP11-369E15.3 | 5.69E−36 | 0.827619667 | 0.025 | 0.009 | 3.82E−32 | Higher in Autistic Samples | II |
| 30 | EIF5A2 | 7.64E−23 | 0.827123788 | 0.012 | 0.003 | 5.12E−19 | Higher in Autistic Samples | II |
| 31 | PTPRD | 2.29E−39 | 0.826868854 | 0.025 | 0.008 | 1.54E−35 | Higher in Autistic Samples | II |
| 32 | RNF139-AS1 | 6.21E−34 | 0.822103513 | 0.018 | 0.005 | 4.16E−30 | Higher in Autistic Samples | II |
| 33 | FAM71F1 | 9.05E−30 | 0.822074912 | 0.017 | 0.005 | 6.06E−26 | Higher in Autistic Samples | II |

TABLE 3-continued

Tier 2 genes (ranked by Average log Fold Change (avg_logFC)).

| | GeneName | p_val | avg_logFC | pct.1 | pct.2 | p_val_adj | Marker Type | Tier |
|---|---|---|---|---|---|---|---|---|
| 34 | CLK3 | 2.65E−31 | 0.816552791 | 0.019 | 0.006 | 1.78E−27 | Higher in Autistic Samples | II |
| 35 | UGT1A6 | 3.75E−35 | 0.81335746 | 0.02 | 0.006 | 2.51E−31 | Higher in Autistic Samples | II |
| 36 | C21orf91 | 6.61E−33 | 0.808135434 | 0.023 | 0.008 | 4.43E−29 | Higher in Autistic Samples | II |
| 37 | DES | 1.07E−32 | 0.805160839 | 0.02 | 0.006 | 7.17E−29 | Higher in Autistic Samples | II |
| 38 | IBA57-AS1 | 3.57E−25 | 0.801699816 | 0.011 | 0.003 | 2.40E−21 | Higher in Autistic Samples | II |
| 39 | HNRNPR | 1.65E−32 | 0.800670784 | 0.018 | 0.005 | 1.11E−28 | Higher in Autistic Samples | II |
| 40 | CCDC168 | 5.35E−21 | 0.794635234 | 0.013 | 0.005 | 3.58E−17 | Higher in Autistic Samples | II |
| 41 | AC013436.6 | 2.94E−38 | 0.788632298 | 0.023 | 0.007 | 1.97E−34 | Higher in Autistic Samples | II |
| 42 | ZNF32-AS3 | 4.81E−35 | 0.78711863 | 0.023 | 0.008 | 3.22E−31 | Higher in Autistic Samples | II |
| 43 | LINC01095 | 8.60E−25 | 0.78540252 | 0.016 | 0.006 | 5.77E−21 | Higher in Autistic Samples | II |
| 44 | MAPKAPK5-AS1 | 8.27E−29 | 0.783704852 | 0.016 | 0.005 | 5.55E−25 | Higher in Autistic Samples | II |
| 45 | RP11-2F20.1 | 2.06E−25 | 0.780365628 | 0.013 | 0.003 | 1.38E−21 | Higher in Autistic Samples | II |
| 46 | DGCR8 | 1.37E−42 | 0.766731421 | 0.03 | 0.011 | 9.18E−39 | Higher in Autistic Samples | II |
| 47 | AC007563.1 | 3.71E−40 | 0.764440456 | 0.029 | 0.01 | 2.49E−36 | Higher in Autistic Samples | II |
| 48 | UBE4A | 2.46E−26 | 0.761891103 | 0.018 | 0.006 | 1.65E−22 | Higher in Autistic Samples | II |
| 49 | AC004510.3 | 5.08E−42 | 0.756198467 | 0.035 | 0.014 | 3.41E−38 | Higher in Autistic Samples | II |
| 50 | SYNCRIP | 3.36E−22 | 0.75227011 | 0.011 | 0.003 | 2.25E−18 | Higher in Autistic Samples | II |
| 51 | HSPH1 | 6.17E−31 | 0.750491405 | 0.022 | 0.008 | 4.14E−27 | Higher in Autistic Samples | II |
| 52 | CTD-2206N4.2 | 1.85E−30 | 0.750272787 | 0.016 | 0.005 | 1.24E−26 | Higher in Autistic Samples | II |
| 53 | LINC00919 | 2.89E−22 | 0.746887369 | 0.014 | 0.005 | 1.94E−18 | Higher in Autistic Samples | II |
| 54 | RP11-17M16.2 | 1.54E−37 | 0.742940268 | 0.027 | 0.01 | 1.03E−33 | Higher in Autistic Samples | II |
| 55 | ADGRG1 | 4.43E−21 | 0.741770148 | 0.013 | 0.004 | 2.97E−17 | Higher in Autistic Samples | II |
| 56 | KRTCAP3 | 4.07E−45 | 0.741592523 | 0.039 | 0.016 | 2.73E−41 | Higher in Autistic Samples | II |
| 57 | JARID2-AS1 | 1.81E−21 | 0.739414915 | 0.011 | 0.003 | 1.21E−17 | Higher in Autistic Samples | II |
| 58 | CREB3L2 | 6.48E−23 | 0.738179704 | 0.012 | 0.003 | 4.34E−19 | Higher in Autistic Samples | II |
| 59 | AC092168.3 | 2.02E−27 | 0.737816115 | 0.015 | 0.005 | 1.36E−23 | Higher in Autistic Samples | II |
| 60 | RP11-493E12.1 | 1.04E−33 | 0.737183029 | 0.021 | 0.007 | 6.96E−30 | Higher in Autistic Samples | II |
| 61 | SETD9 | 5.67E−34 | 0.732350976 | 0.031 | 0.013 | 3.80E−30 | Higher in Autistic Samples | II |
| 62 | MRC2 | 1.46E−22 | 0.729698442 | 0.014 | 0.005 | 9.79E−19 | Higher in Autistic Samples | II |
| 63 | AC008937.3 | 9.01E−30 | 0.72874155 | 0.022 | 0.008 | 6.04E−26 | Higher in Autistic Samples | II |
| 64 | RP11-159D12.10 | 2.90E−26 | 0.726991619 | 0.015 | 0.004 | 1.95E−22 | Higher in Autistic Samples | II |
| 65 | CCSER1 | 2.20E−34 | 0.725197322 | 0.026 | 0.01 | 1.48E−30 | Higher in Autistic Samples | II |
| 66 | RP11-1018N14.1 | 2.42E−24 | 0.721466803 | 0.012 | 0.003 | 1.62E−20 | Higher in Autistic Samples | II |
| 67 | FILIP1L | 1.89E−26 | 0.718233414 | 0.017 | 0.006 | 1.27E−22 | Higher in Autistic Samples | II |
| 68 | KIAA1217 | 1.09E−26 | 0.716565594 | 0.015 | 0.005 | 7.31E−23 | Higher in Autistic Samples | II |
| 69 | RNFT2 | 2.65E−22 | 0.716482446 | 0.012 | 0.004 | 1.78E−18 | Higher in Autistic Samples | II |
| 70 | NDUFA11 | 1.13E−25 | 0.71459114 | 0.015 | 0.005 | 7.60E−22 | Higher in Autistic Samples | II |
| 71 | AC015971.2 | 3.36E−29 | 0.712116597 | 0.02 | 0.007 | 2.26E−25 | Higher in Autistic Samples | II |
| 72 | CDH23 | 1.78E−25 | 0.707983612 | 0.011 | 0.002 | 1.19E−21 | Higher in Autistic Samples | II |
| 73 | RP11-98D18.16 | 8.59E−50 | 0.707524422 | 0.047 | 0.02 | 5.76E−46 | Higher in Autistic Samples | II |
| 74 | HNRNPH1 | 1.13E−19 | 0.702454628 | 0.013 | 0.005 | 7.58E−16 | Higher in Autistic Samples | II |
| 75 | CTB-55O6.13 | 3.99E−28 | 0.6987786 | 0.022 | 0.008 | 2.67E−24 | Higher in Autistic Samples | II |
| 76 | P4HTM | 5.72E−18 | 0.697926892 | 0.013 | 0.005 | 3.83E−14 | Higher in Autistic Samples | II |
| 77 | SMIM6 | 2.05E−19 | 0.692372535 | 0.014 | 0.005 | 1.37E−15 | Higher in Autistic Samples | II |
| 78 | TTLL1 | 3.58E−26 | 0.688855383 | 0.015 | 0.005 | 2.40E−22 | Higher in Autistic Samples | II |
| 79 | UQCRB | 1.50E−33 | 0.686781061 | 0.029 | 0.012 | 1.00E−29 | Higher in Autistic Samples | II |
| 80 | AC097495.2 | 4.20E−33 | 0.68642708 | 0.027 | 0.011 | 2.82E−29 | Higher in Autistic Samples | II |
| 81 | RP11-796E2.4 | 2.56E−22 | 0.686154578 | 0.014 | 0.004 | 1.72E−18 | Higher in Autistic Samples | II |
| 82 | LYSMD2 | 3.11E−25 | 0.68479335 | 0.017 | 0.006 | 2.09E−21 | Higher in Autistic Samples | II |
| 83 | MGAT4C | 4.88E−17 | 0.680923267 | 0.011 | 0.004 | 3.27E−13 | Higher in Autistic Samples | II |
| 84 | RP11-862G15.1 | 5.78E−23 | 0.679307235 | 0.015 | 0.005 | 3.88E−19 | Higher in Autistic Samples | II |
| 85 | PFN3 | 4.11E−24 | 0.67882913 | 0.016 | 0.006 | 2.75E−20 | Higher in Autistic Samples | II |
| 86 | FAM212B | 3.64E−28 | 0.678516874 | 0.019 | 0.007 | 2.44E−24 | Higher in Autistic Samples | II |
| 87 | RBM15B | 3.90E−22 | 0.675644689 | 0.014 | 0.005 | 2.62E−18 | Higher in Autistic Samples | II |
| 88 | RNF103 | 5.93E−21 | 0.674707901 | 0.013 | 0.004 | 3.98E−17 | Higher in Autistic Samples | II |
| 89 | RP11-396F22.1 | 6.61E−20 | 0.670569286 | 0.015 | 0.006 | 4.43E−16 | Higher in Autistic Samples | II |
| 90 | C10orf82 | 6.87E−18 | 0.668441198 | 0.011 | 0.003 | 4.61E−14 | Higher in Autistic Samples | II |
| 91 | SYS1 | 9.30E−22 | 0.664815706 | 0.013 | 0.004 | 6.24E−18 | Higher in Autistic Samples | II |
| 92 | RP11-404L6.2 | 2.43E−16 | 0.664231526 | 0.011 | 0.004 | 1.63E−12 | Higher in Autistic Samples | II |
| 93 | DDX5 | 3.06E−33 | 0.663239748 | 0.027 | 0.011 | 2.05E−29 | Higher in Autistic Samples | II |
| 94 | LINC00906 | 5.20E−17 | 0.660910625 | 0.015 | 0.006 | 3.49E−13 | Higher in Autistic Samples | II |
| 95 | PSMD3 | 4.95E−23 | 0.660130713 | 0.016 | 0.006 | 3.32E−19 | Higher in Autistic Samples | II |
| 96 | PPP1R3E | 6.87E−31 | 0.659680528 | 0.024 | 0.009 | 4.60E−27 | Higher in Autistic Samples | II |
| 97 | PTK7 | 2.75E−37 | 0.653979608 | 0.04 | 0.018 | 1.84E−33 | Higher in Autistic Samples | II |
| 98 | LINC01487 | 1.52E−21 | 0.646643615 | 0.012 | 0.004 | 1.02E−17 | Higher in Autistic Samples | II |
| 99 | MAP3K14-AS1 | 4.25E−25 | 0.646068218 | 0.021 | 0.009 | 2.85E−21 | Higher in Autistic Samples | II |
| 100 | MRPL9 | 2.05E−19 | 0.645817092 | 0.016 | 0.006 | 1.38E−15 | Higher in Autistic Samples | II |
| 101 | ZFYVE28 | 3.26E−20 | 0.639079144 | 0.012 | 0.004 | 2.18E−16 | Higher in Autistic Samples | II |
| 102 | KRTDAP | 2.03E−20 | 0.639015979 | 0.018 | 0.008 | 1.36E−16 | Higher in Autistic Samples | II |
| 103 | OSBP2 | 8.17E−35 | 0.638550225 | 0.036 | 0.016 | 5.48E−31 | Higher in Autistic Samples | II |
| 104 | NUMBL | 1.93E−18 | 0.637931002 | 0.014 | 0.005 | 1.29E−14 | Higher in Autistic Samples | II |
| 105 | FKBP7 | 6.76E−20 | 0.635578663 | 0.012 | 0.004 | 4.53E−16 | Higher in Autistic Samples | II |
| 106 | LMX1A | 2.75E−21 | 0.634648326 | 0.014 | 0.005 | 1.84E−17 | Higher in Autistic Samples | II |
| 107 | TXNDC2 | 1.64E−15 | 0.634061291 | 0.013 | 0.006 | 1.10E−11 | Higher in Autistic Samples | II |
| 108 | ZCCHC8 | 3.48E−18 | 0.633985651 | 0.013 | 0.005 | 2.34E−14 | Higher in Autistic Samples | II |
| 109 | RP11-666A8.9 | 1.20E−16 | 0.633913897 | 0.013 | 0.005 | 8.03E−13 | Higher in Autistic Samples | II |

TABLE 3-continued

Tier 2 genes (ranked by Average log Fold Change (avg_logFC)).

| | GeneName | p_val | avg_logFC | pct.1 | pct.2 | p_val_adj | Marker Type | Tier |
|---|---|---|---|---|---|---|---|---|
| 110 | RP5-1051H14.2 | 1.38E−29 | 0.6327314 | 0.028 | 0.012 | 9.24E−26 | Higher in Autistic Samples | II |
| 111 | NRBP1 | 7.82E−23 | 0.628698623 | 0.022 | 0.01 | 5.24E−19 | Higher in Autistic Samples | II |
| 112 | FAM170B-AS1 | 1.36E−41 | 0.628142506 | 0.046 | 0.021 | 9.15E−38 | Higher in Autistic Samples | II |
| 113 | RP11-439E19.9 | 1.54E−20 | 0.626901942 | 0.017 | 0.007 | 1.03E−17 | Higher in Autistic Samples | II |
| 114 | RPL37 | 1.22E−31 | 0.62382701 | 0.029 | 0.012 | 8.16E−28 | Higher in Autistic Samples | II |
| 115 | MGST3 | 1.90E−18 | 0.623570247 | 0.012 | 0.004 | 1.27E−14 | Higher in Autistic Samples | II |
| 116 | CTD-2020K17.4 | 8.85E−30 | 0.620057691 | 0.03 | 0.014 | 5.93E−26 | Higher in Autistic Samples | II |
| 117 | SCRT1 | 3.38E−25 | 0.615728816 | 0.017 | 0.006 | 2.26E−21 | Higher in Autistic Samples | II |
| 118 | RP11-173A6.3 | 3.01E−24 | 0.615202627 | 0.015 | 0.005 | 2.02E−20 | Higher in Autistic Samples | II |
| 119 | FBXO34 | 3.11E−21 | 0.614307774 | 0.021 | 0.009 | 2.09E−17 | Higher in Autistic Samples | II |
| 120 | MRFAP1 | 3.43E−17 | 0.609163805 | 0.014 | 0.006 | 2.30E−13 | Higher in Autistic Samples | II |
| 121 | TRIM11 | 1.83E−42 | 0.608917658 | 0.048 | 0.023 | 1.23E−38 | Higher in Autistic Samples | II |
| 122 | PCBP4 | 4.25E−17 | 0.60859077 | 0.013 | 0.005 | 2.85E−13 | Higher in Autistic Samples | II |
| 123 | RANBP2 | 3.22E−14 | 0.602189905 | 0.011 | 0.004 | 2.16E−10 | Higher in Autistic Samples | II |
| 124 | FAM229A | 2.63E−27 | 0.600739289 | 0.027 | 0.012 | 1.76E−23 | Higher in Autistic Samples | II |
| 125 | EQTN | 1.11E−20 | 0.596549558 | 0.02 | 0.009 | 7.46E−17 | Higher in Autistic Samples | II |
| 126 | GOLGA6L10 | 1.30E−17 | 0.595699922 | 0.011 | 0.004 | 8.71E−14 | Higher in Autistic Samples | II |
| 127 | AC116609.1 | 5.31E−20 | 0.594174448 | 0.011 | 0.003 | 3.56E−16 | Higher in Autistic Samples | II |
| 128 | MTPAP | 1.87E−20 | 0.592606314 | 0.023 | 0.011 | 1.26E−16 | Higher in Autistic Samples | II |
| 129 | GSTO1 | 2.43E−32 | 0.592234044 | 0.034 | 0.016 | 1.63E−28 | Higher in Autistic Samples | II |
| 130 | PACS2 | 4.21E−20 | 0.590685619 | 0.019 | 0.008 | 2.82E−16 | Higher in Autistic Samples | II |
| 131 | CTD-3035K23.7 | 5.24E−23 | 0.587010025 | 0.021 | 0.009 | 3.51E−19 | Higher in Autistic Samples | II |
| 132 | RP11-73K9.2 | 1.01E−15 | 0.582526519 | 0.011 | 0.004 | 6.75E−12 | Higher in Autistic Samples | II |
| 133 | FAM153A | 9.92E−20 | 0.581605871 | 0.017 | 0.007 | 6.65E−16 | Higher in Autistic Samples | II |
| 134 | CCDC80 | 6.75E−33 | 0.573988346 | 0.038 | 0.018 | 4.53E−29 | Higher in Autistic Samples | II |
| 135 | ACTL7B | 1.30E−13 | 0.568003223 | 0.011 | 0.005 | 8.73E−10 | Higher in Autistic Samples | II |
| 136 | CFL1 | 8.58E−21 | 0.567655874 | 0.03 | 0.016 | 5.75E−17 | Higher in Autistic Samples | II |
| 137 | RP11-1O10.1 | 5.52E−24 | 0.566199485 | 0.025 | 0.012 | 3.70E−20 | Higher in Autistic Samples | II |
| 138 | GTSF1L | 1.49E−18 | 0.563332412 | 0.02 | 0.009 | 9.98E−15 | Higher in Autistic Samples | II |
| 139 | AC007557.4 | 4.32E−16 | 0.562140803 | 0.013 | 0.006 | 2.90E−12 | Higher in Autistic Samples | II |
| 140 | SPIRE1 | 1.10E−15 | 0.556359569 | 0.016 | 0.007 | 7.36E−12 | Higher in Autistic Samples | II |
| 141 | MRPS7 | 1.25E−14 | 0.555618347 | 0.02 | 0.01 | 8.35E−11 | Higher in Autistic Samples | II |
| 142 | EAF1-AS1 | 3.57E−17 | 0.552320083 | 0.015 | 0.007 | 2.39E−13 | Higher in Autistic Samples | II |
| 143 | RP11-545G3.1 | 3.48E−26 | 0.550869674 | 0.039 | 0.021 | 2.33E−22 | Higher in Autistic Samples | II |
| 144 | IQCF3 | 4.24E−17 | 0.549368897 | 0.017 | 0.008 | 2.85E−13 | Higher in Autistic Samples | II |
| 145 | CLIC5 | 1.04E−18 | 0.549365686 | 0.016 | 0.007 | 6.96E−15 | Higher in Autistic Samples | II |
| 146 | SLC37A1 | 2.10E−14 | 0.544599868 | 0.014 | 0.006 | 1.41E−10 | Higher in Autistic Samples | II |
| 147 | RP11-394A14.2 | 5.96E−13 | 0.535923676 | 0.012 | 0.005 | 4.00E−09 | Higher in Autistic Samples | II |
| 148 | MYH7B | 8.26E−13 | 0.534238569 | 0.016 | 0.008 | 5.54E−09 | Higher in Autistic Samples | II |
| 149 | FKBP3 | 7.33E−11 | 0.522020977 | 0.018 | 0.01 | 4.91E−07 | Higher in Autistic Samples | II |
| 150 | MINOS1 | 5.71E−14 | 0.517738708 | 0.015 | 0.007 | 3.83E−10 | Higher in Autistic Samples | II |
| 151 | CENPJ | 1.56E−09 | 0.515967056 | 0.011 | 0.006 | 1.05E−05 | Higher in Autistic Samples | II |
| 152 | CFAP44 | 5.47E−12 | 0.510319117 | 0.012 | 0.006 | 3.67E−08 | Higher in Autistic Samples | II |
| 153 | BRD2 | 1.09E−09 | 0.506559706 | 0.013 | 0.007 | 7.32E−06 | Higher in Autistic Samples | II |
| 154 | RP11-684B21.1 | 4.07E−12 | 0.503627132 | 0.012 | 0.005 | 2.73E−08 | Higher in Autistic Samples | II |
| 155 | AGAP1 | 3.04E−15 | 0.502363581 | 0.013 | 0.005 | 2.04E−11 | Higher in Autistic Samples | II |
| 156 | FARP2 | 4.92E−17 | 0.501113815 | 0.02 | 0.009 | 3.30E−13 | Higher in Autistic Samples | II |
| 157 | MIR7515HG | 3.28E−30 | 0.500777692 | 0.043 | 0.023 | 2.20E−26 | Higher in Autistic Samples | II |
| 158 | RP11-544A12.8 | 6.50E−14 | 0.500222998 | 0.012 | 0.005 | 4.36E−10 | Higher in Autistic Samples | II |
| 159 | KMO | 1.43E−22 | 0.496209432 | 0.027 | 0.013 | 9.60E−19 | Higher in Autistic Samples | II |
| 160 | FAM209A | 1.63E−10 | 0.494594921 | 0.012 | 0.006 | 1.09E−06 | Higher in Autistic Samples | II |
| 161 | TMEM160 | 2.72E−13 | 0.493454656 | 0.015 | 0.007 | 1.82E−09 | Higher in Autistic Samples | II |
| 162 | TAF5L | 6.49E−14 | 0.49183306 | 0.013 | 0.006 | 4.35E−10 | Higher in Autistic Samples | II |
| 163 | PSMA4 | 2.78E−18 | 0.490588459 | 0.016 | 0.006 | 1.86E−14 | Higher in Autistic Samples | II |
| 164 | LINC01198 | 3.68E−14 | 0.487809173 | 0.014 | 0.006 | 2.47E−10 | Higher in Autistic Samples | II |
| 165 | LDLRAD4 | 1.40E−17 | 0.487137113 | 0.02 | 0.009 | 9.36E−14 | Higher in Autistic Samples | II |
| 166 | LINC00442 | 2.54E−12 | 0.482295663 | 0.011 | 0.005 | 1.70E−08 | Higher in Autistic Samples | II |
| 167 | HYAL1 | 2.07E−11 | 0.481837873 | 0.012 | 0.005 | 1.39E−07 | Higher in Autistic Samples | II |
| 168 | ATPAF1 | 2.52E−22 | 0.470421884 | 0.038 | 0.022 | 1.69E−18 | Higher in Autistic Samples | II |
| 169 | C20orf144 | 1.20E−15 | 0.46336823 | 0.024 | 0.013 | 8.07E−12 | Higher in Autistic Samples | II |
| 170 | ARF4-AS1 | 6.48E−13 | 0.457966573 | 0.016 | 0.008 | 4.35E−09 | Higher in Autistic Samples | II |
| 171 | APOPT1 | 6.63E−15 | 0.455781057 | 0.016 | 0.008 | 4.44E−11 | Higher in Autistic Samples | II |
| 172 | DNAAF3 | 6.29E−24 | 0.453674076 | 0.049 | 0.029 | 4.22E−20 | Higher in Autistic Samples | II |
| 173 | EIF5A | 4.48E−10 | 0.447839367 | 0.013 | 0.007 | 3.00E−06 | Higher in Autistic Samples | II |
| 174 | NFIB | 8.42E−10 | 0.436721714 | 0.011 | 0.006 | 5.65E−06 | Higher in Autistic Samples | II |
| 175 | HPCA | 4.94E−12 | 0.426402625 | 0.016 | 0.008 | 3.31E−08 | Higher in Autistic Samples | II |
| 176 | CSPP1 | 1.83E−14 | 0.426320803 | 0.024 | 0.014 | 1.23E−10 | Higher in Autistic Samples | II |
| 177 | IPO5 | 6.91E−09 | 0.423768378 | 0.014 | 0.008 | 4.64E−05 | Higher in Autistic Samples | II |
| 178 | RP11-360D2.1 | 3.45E−09 | 0.421688867 | 0.012 | 0.006 | 2.31E−05 | Higher in Autistic Samples | II |
| 179 | KATNBL1 | 2.64E−15 | 0.421383795 | 0.033 | 0.021 | 1.77E−11 | Higher in Autistic Samples | II |
| 180 | EIF2B4 | 2.44E−10 | 0.420581304 | 0.013 | 0.007 | 1.63E−06 | Higher in Autistic Samples | II |
| 181 | WI2-2373I1.2 | 7.03E−13 | 0.404253912 | 0.029 | 0.018 | 4.72E−09 | Higher in Autistic Samples | II |
| 182 | POLB | 1.41E−09 | 0.40375342 | 0.013 | 0.007 | 9.45E−06 | Higher in Autistic Samples | II |
| 183 | FAM229B | 1.16E−12 | 0.396923894 | 0.029 | 0.018 | 7.79E−09 | Higher in Autistic Samples | II |
| 184 | RP11-326K13.4 | 1.31E−19 | 0.392243725 | 0.032 | 0.017 | 8.80E−16 | Higher in Autistic Samples | II |
| 185 | FAM81B | 2.19E−09 | 0.386609924 | 0.021 | 0.013 | 1.47E−05 | Higher in Autistic Samples | II |

TABLE 3-continued

Tier 2 genes (ranked by Average log Fold Change (avg_logFC)).

| | GeneName | p_val | avg_logFC | pct.1 | pct.2 | p_val_adj | Marker Type | Tier |
|---|---|---|---|---|---|---|---|---|
| 186 | PLCE1-AS2 | 5.55E-10 | 0.383274466 | 0.016 | 0.009 | 3.72E-06 | Higher in Autistic Samples | II |
| 187 | BAZ2A | 7.69E-11 | 0.37671031 | 0.011 | 0.005 | 5.15E-07 | Higher in Autistic Samples | II |
| 188 | GNAI2 | 1.46E-12 | 0.375198431 | 0.023 | 0.013 | 9.81E-09 | Higher in Autistic Samples | II |
| 189 | ZEB1 | 1.48E-06 | 0.36698259 | 0.013 | 0.008 | 0.00991351 | Higher in Autistic Samples | II |
| 190 | FAM83C | 1.01E-06 | 0.358730444 | 0.013 | 0.008 | 0.00675847 | Higher in Autistic Samples | II |
| 191 | NDUFS8 | 2.16E-08 | 0.358335946 | 0.016 | 0.009 | 0.00014499 | Higher in Autistic Samples | II |
| 192 | DYNLL1 | 1.24E-06 | 0.352857489 | 0.013 | 0.008 | 0.00828422 | Higher in Autistic Samples | II |
| 193 | HMGB4 | 3.63E-08 | 0.33517096 | 0.025 | 0.017 | 0.00024351 | Higher in Autistic Samples | II |
| 194 | LMNTD2 | 5.62E-06 | 0.333241557 | 0.013 | 0.008 | 0.03767966 | Higher in Autistic Samples | II |
| 195 | C1orf43 | 8.54E-08 | 0.332161115 | 0.013 | 0.008 | 0.00057247 | Higher in Autistic Samples | II |
| 196 | LINC00943 | 2.09E-07 | 0.327729013 | 0.018 | 0.012 | 0.00139957 | Higher in Autistic Samples | II |
| 197 | RP1-266L20.2 | 8.28E-09 | 0.326966545 | 0.014 | 0.008 | 5.55E-05 | Higher in Autistic Samples | II |
| 198 | SAMD4A | 8.26E-10 | 0.326473702 | 0.025 | 0.016 | 5.54E-06 | Higher in Autistic Samples | II |
| 199 | SNHG9 | 1.41E-07 | 0.320829493 | 0.017 | 0.011 | 0.0009471 | Higher in Autistic Samples | II |
| 200 | TLE4 | 3.57E-07 | 0.31875096 | 0.015 | 0.01 | 0.00239168 | Higher in Autistic Samples | II |
| 201 | CITED4 | 1.59E-08 | 0.317941004 | 0.019 | 0.012 | 0.00010637 | Higher in Autistic Samples | II |
| 202 | HDAC11 | 8.96E-12 | 0.316154448 | 0.036 | 0.024 | 6.01E-08 | Higher in Autistic Samples | II |
| 203 | RP11-192H23.7 | 6.54E-09 | 0.313614152 | 0.016 | 0.009 | 4.39E-05 | Higher in Autistic Samples | II |
| 204 | TMEM191C | 2.78E-06 | 0.312829836 | 0.02 | 0.014 | 0.0186523 | Higher in Autistic Samples | II |
| 205 | TUBGCP4 | 1.88E-11 | 0.308411203 | 0.027 | 0.017 | 1.26E-07 | Higher in Autistic Samples | II |
| 206 | PGP | 9.13E-12 | 0.308180878 | 0.032 | 0.021 | 6.12E-08 | Higher in Autistic Samples | II |
| 207 | PRM3 | 2.43E-07 | 0.307244714 | 0.012 | 0.007 | 0.00163149 | Higher in Autistic Samples | II |
| 208 | NDUFB6 | 7.03E-08 | 0.296909047 | 0.012 | 0.007 | 0.00047111 | Higher in Autistic Samples | II |
| 209 | RND2 | 3.95E-07 | 0.2958768 | 0.025 | 0.018 | 0.00265125 | Higher in Autistic Samples | II |
| 210 | WDR74 | 6.33E-08 | 0.289090485 | 0.021 | 0.014 | 0.00042409 | Higher in Autistic Samples | II |
| 211 | RP11-666O2.2 | 2.36E-08 | 0.277986666 | 0.026 | 0.018 | 0.00015835 | Higher in Autistic Samples | II |
| 212 | PIN1 | 1.96E-07 | 0.274396674 | 0.021 | 0.014 | 0.00131396 | Higher in Autistic Samples | II |
| 213 | ZNRD1 | 3.11E-06 | 0.27399136 | 0.011 | 0.006 | 0.02084318 | Higher in Autistic Samples | II |
| 214 | TAF10 | 1.15E-07 | 0.265176951 | 0.023 | 0.016 | 0.00077286 | Higher in Autistic Samples | II |
| 215 | H3F3B | 3.21E-11 | 0.26244744 | 0.044 | 0.031 | 2.15E-07 | Higher in Autistic Samples | II |
| 216 | COX7C | 2.07E-06 | 0.257332905 | 0.012 | 0.007 | 0.01384988 | Higher in Autistic Samples | II |
| 217 | C3orf22 | 1.08E-06 | -0.26613926 | 0.032 | 0.042 | 0.00720796 | Higher in Normal/Healthy Samples | II |
| 218 | CLPB | 3.05E-10 | -0.275447642 | 0.036 | 0.049 | 2.04E-06 | Higher in Normal/Healthy Samples | II |
| 219 | NDUFA13 | 2.63E-12 | -0.279517919 | 0.023 | 0.036 | 1.76E-08 | Higher in Normal/Healthy Samples | II |
| 220 | MYL6B | 2.92E-06 | -0.281164822 | 0.02 | 0.027 | 0.0195819 | Higher in Normal/Healthy Samples | II |
| 221 | AURKAIP1 | 1.14E-07 | -0.281831438 | 0.035 | 0.045 | 0.00076432 | Higher in Normal/Healthy Samples | II |
| 222 | TMBIM6 | 5.62E-11 | -0.282430846 | 0.034 | 0.047 | 3.77E-07 | Higher in Normal/Healthy Samples | II |
| 223 | GKAP1 | 7.82E-09 | -0.294901148 | 0.006 | 0.012 | 5.24E-05 | Higher in Normal/Healthy Samples | II |
| 224 | CEP85L | 1.51E-07 | -0.302615808 | 0.017 | 0.025 | 0.00101338 | Higher in Normal/Healthy Samples | II |
| 225 | DUSP15 | 2.24E-10 | -0.308518587 | 0.024 | 0.035 | 1.50E-06 | Higher in Normal/Healthy Samples | II |
| 226 | TMEM38B | 2.07E-08 | -0.308856067 | 0.014 | 0.021 | 0.0001388 | Higher in Normal/Healthy Samples | II |
| 227 | RP11-109E10.1 | 2.92E-07 | -0.310564624 | 0.009 | 0.014 | 0.00195682 | Higher in Normal/Healthy Samples | II |
| 228 | RNF139 | 3.57E-09 | -0.313425388 | 0.015 | 0.023 | 2.39E-05 | Higher in Normal/Healthy Samples | II |
| 229 | ZMIZ2 | 2.21E-06 | -0.320869732 | 0.016 | 0.023 | 0.01481379 | Higher in Normal/Healthy Samples | II |
| 230 | CIB2 | 8.74E-07 | -0.32356951 | 0.008 | 0.013 | 0.00585915 | Higher in Normal/Healthy Samples | II |
| 231 | GDPD5 | 1.71E-06 | -0.326046248 | 0.011 | 0.017 | 0.01144693 | Higher in Normal/Healthy Samples | II |
| 232 | RCOR3 | 1.24E-06 | -0.327510002 | 0.006 | 0.011 | 0.0083402 | Higher in Normal/Healthy Samples | II |
| 233 | PPM1G | 3.23E-08 | -0.328006066 | 0.018 | 0.027 | 0.00021656 | Higher in Normal/Healthy Samples | II |
| 234 | C7orf73 | 2.33E-06 | -0.32976221 | 0.011 | 0.017 | 0.01560061 | Higher in Normal/Healthy Samples | II |
| 235 | ZNF706 | 7.66E-15 | -0.330659287 | 0.028 | 0.043 | 5.14E-11 | Higher in Normal/Healthy Samples | II |
| 236 | SNX13 | 5.23E-07 | -0.331427023 | 0.008 | 0.013 | 0.00350463 | Higher in Normal/Healthy Samples | II |
| 237 | DZIP1 | 1.30E-07 | -0.332355497 | 0.01 | 0.016 | 0.00086975 | Higher in Normal/Healthy Samples | II |
| 238 | HBP1 | 5.41E-07 | -0.336074223 | 0.007 | 0.012 | 0.00362506 | Higher in Normal/Healthy Samples | II |
| 239 | ZNF571-AS1 | 6.62E-07 | -0.346212044 | 0.013 | 0.019 | 0.00444126 | Higher in Normal/Healthy Samples | II |
| 240 | CPTP | 1.54E-06 | -0.34650817 | 0.01 | 0.015 | 0.01029542 | Higher in Normal/Healthy Samples | II |
| 241 | C9orf73 | 2.90E-07 | -0.350299182 | 0.01 | 0.016 | 0.00194462 | Higher in Normal/Healthy Samples | II |
| 242 | BAG5 | 7.55E-10 | -0.352066628 | 0.012 | 0.02 | 5.06E-06 | Higher in Normal/Healthy Samples | II |
| 243 | IZUMO4 | 1.80E-07 | -0.352182518 | 0.014 | 0.021 | 0.00120392 | Higher in Normal/Healthy Samples | II |
| 244 | C6orf120 | 2.10E-06 | -0.353343031 | 0.007 | 0.012 | 0.01405928 | Higher in Normal/Healthy Samples | II |
| 245 | MFAP3L | 7.71E-13 | -0.358023693 | 0.022 | 0.035 | 5.17E-09 | Higher in Normal/Healthy Samples | II |
| 246 | ZC3H15 | 5.61E-08 | -0.358418732 | 0.008 | 0.013 | 0.00037602 | Higher in Normal/Healthy Samples | II |
| 247 | LRRD1 | 1.73E-15 | -0.360725632 | 0.02 | 0.033 | 1.16E-11 | Higher in Normal/Healthy Samples | II |
| 248 | ENO1 | 1.21E-07 | -0.362403422 | 0.012 | 0.018 | 0.00081186 | Higher in Normal/Healthy Samples | II |
| 249 | C9orf16 | 2.50E-10 | -0.363986176 | 0.027 | 0.038 | 1.68E-06 | Higher in Normal/Healthy Samples | II |
| 250 | NAT6 | 1.42E-06 | -0.364300871 | 0.013 | 0.019 | 0.00948987 | Higher in Normal/Healthy Samples | II |
| 251 | BRK1 | 5.08E-07 | -0.365524073 | 0.01 | 0.015 | 0.00340578 | Higher in Normal/Healthy Samples | II |
| 252 | POLD2 | 6.09E-06 | -0.36625975 | 0.007 | 0.011 | 0.04080064 | Higher in Normal/Healthy Samples | II |
| 253 | SORBS3 | 1.10E-10 | -0.368057444 | 0.016 | 0.025 | 7.40E-07 | Higher in Normal/Healthy Samples | II |
| 254 | RPL23A | 4.93E-07 | -0.375147158 | 0.009 | 0.014 | 0.00330833 | Higher in Normal/Healthy Samples | II |
| 255 | AGPAT2 | 3.82E-07 | -0.375380447 | 0.013 | 0.02 | 0.00256039 | Higher in Normal/Healthy Samples | II |
| 256 | SMPD2 | 5.49E-06 | -0.377768545 | 0.009 | 0.014 | 0.03679237 | Higher in Normal/Healthy Samples | II |
| 257 | DMWD | 5.09E-07 | -0.379042906 | 0.008 | 0.013 | 0.00341447 | Higher in Normal/Healthy Samples | II |
| 258 | ODC1 | 6.66E-10 | -0.382122009 | 0.012 | 0.02 | 4.47E-06 | Higher in Normal/Healthy Samples | II |
| 259 | PCGF5 | 1.20E-09 | -0.383582561 | 0.007 | 0.014 | 8.06E-06 | Higher in Normal/Healthy Samples | II |
| 260 | AC007325.4 | 1.89E-08 | -0.386007192 | 0.007 | 0.013 | 0.00012651 | Higher in Normal/Healthy Samples | II |
| 261 | CCDC37-AS1 | 5.80E-11 | -0.388188744 | 0.021 | 0.032 | 3.89E-07 | Higher in Normal/Healthy Samples | II |

TABLE 3-continued

Tier 2 genes (ranked by Average log Fold Change (avg_logFC)).

| | GeneName | p_val | avg_logFC | pct.1 | pct.2 | p_val_adj | Marker Type | Tier |
|---|---|---|---|---|---|---|---|---|
| 262 | PEX10 | 2.70E−06 | −0.388197307 | 0.006 | 0.011 | 0.01812557 | Higher in Normal/Healthy Samples | II |
| 263 | ACTL10 | 2.52E−07 | −0.388814781 | 0.009 | 0.015 | 0.00168893 | Higher in Normal/Healthy Samples | II |
| 264 | PAOX | 7.76E−11 | −0.389408555 | 0.018 | 0.028 | 5.20E−07 | Higher in Normal/Healthy Samples | II |
| 265 | ACTL7A | 6.54E−06 | −0.389460986 | 0.009 | 0.013 | 0.04384962 | Higher in Normal/Healthy Samples | II |
| 266 | KDM5B | 4.86E−09 | −0.390473064 | 0.005 | 0.011 | 3.26E−05 | Higher in Normal/Healthy Samples | II |
| 267 | C11orf68 | 1.07E−07 | −0.392185758 | 0.007 | 0.012 | 0.00071593 | Higher in Normal/Healthy Samples | II |
| 268 | USP2 | 5.47E−13 | −0.393443745 | 0.017 | 0.028 | 3.67E−09 | Higher in Normal/Healthy Samples | II |
| 269 | TMEM120A | 4.16E−09 | −0.395129849 | 0.013 | 0.021 | 2.79E−05 | Higher in Normal/Healthy Samples | II |
| 270 | EIF4E | 4.65E−13 | −0.395833845 | 0.017 | 0.028 | 3.12E−09 | Higher in Normal/Healthy Samples | II |
| 271 | EPN1 | 1.97E−08 | −0.3964072 | 0.011 | 0.017 | 0.00013238 | Higher in Normal/Healthy Samples | II |
| 272 | TCP1 | 1.44E−11 | −0.398356032 | 0.012 | 0.021 | 9.68E−08 | Higher in Normal/Healthy Samples | II |
| 273 | UBAC1 | 3.72E−09 | −0.398535908 | 0.005 | 0.011 | 2.49E−05 | Higher in Normal/Healthy Samples | II |
| 274 | TTC7A | 7.49E−12 | −0.400503945 | 0.018 | 0.029 | 5.02E−08 | Higher in Normal/Healthy Samples | II |
| 275 | C10orf62 | 9.61E−15 | −0.401872089 | 0.03 | 0.045 | 6.45E−11 | Higher in Normal/Healthy Samples | II |
| 276 | RUVBL2 | 3.36E−06 | −0.404257232 | 0.006 | 0.011 | 0.0225145 | Higher in Normal/Healthy Samples | II |
| 277 | MAD2L2 | 2.50E−11 | −0.405915612 | 0.018 | 0.028 | 1.68E−07 | Higher in Normal/Healthy Samples | II |
| 278 | AP2B1 | 2.64E−10 | −0.405925561 | 0.006 | 0.013 | 1.77E−06 | Higher in Normal/Healthy Samples | II |
| 279 | MAATS1 | 1.45E−08 | −0.406977959 | 0.006 | 0.011 | 9.74E−05 | Higher in Normal/Healthy Samples | II |
| 280 | RAD23B | 8.63E−09 | −0.407698825 | 0.007 | 0.013 | 5.79E−05 | Higher in Normal/Healthy Samples | II |
| 281 | PPP2R2B | 1.33E−08 | −0.412014417 | 0.007 | 0.012 | 8.91E−05 | Higher in Normal/Healthy Samples | II |
| 282 | ST13 | 1.73E−08 | −0.415151858 | 0.005 | 0.011 | 0.00011588 | Higher in Normal/Healthy Samples | II |
| 283 | KLHDC3 | 2.79E−08 | −0.417567076 | 0.006 | 0.012 | 0.0001868 | Higher in Normal/Healthy Samples | II |
| 284 | EEF1D | 2.25E−08 | −0.423829621 | 0.008 | 0.013 | 0.00015114 | Higher in Normal/Healthy Samples | II |
| 285 | PTDSS2 | 2.73E−10 | −0.424885906 | 0.013 | 0.021 | 1.83E−06 | Higher in Normal/Healthy Samples | II |
| 286 | SLC5A2 | 5.50E−10 | −0.425408936 | 0.016 | 0.025 | 3.69E−06 | Higher in Normal/Healthy Samples | II |
| 287 | TP53I11 | 8.86E−14 | −0.425656445 | 0.023 | 0.036 | 5.94E−10 | Higher in Normal/Healthy Samples | II |
| 288 | SLC2A8 | 5.01E−10 | −0.42686856 | 0.011 | 0.019 | 3.36E−06 | Higher in Normal/Healthy Samples | II |
| 289 | C12orf50 | 7.46E−12 | −0.426968734 | 0.009 | 0.017 | 5.00E−08 | Higher in Normal/Healthy Samples | II |
| 290 | RPL36 | 4.20E−08 | −0.429276937 | 0.008 | 0.013 | 0.00028178 | Higher in Normal/Healthy Samples | II |
| 291 | STARD10 | 2.76E−13 | −0.430084615 | 0.022 | 0.035 | 1.85E−09 | Higher in Normal/Healthy Samples | II |
| 292 | TBC1D10B | 3.31E−06 | −0.43109398 | 0.006 | 0.011 | 0.02219064 | Higher in Normal/Healthy Samples | II |
| 293 | CDHR2 | 6.82E−07 | −0.432719335 | 0.006 | 0.011 | 0.00457118 | Higher in Normal/Healthy Samples | II |
| 294 | ACE | 2.07E−16 | −0.432739067 | 0.029 | 0.045 | 1.39E−12 | Higher in Normal/Healthy Samples | II |
| 295 | ITPKA | 6.09E−06 | −0.433760309 | 0.006 | 0.011 | 0.04081744 | Higher in Normal/Healthy Samples | II |
| 296 | DGCR14 | 1.56E−09 | −0.43582176 | 0.007 | 0.013 | 1.05E−05 | Higher in Normal/Healthy Samples | II |
| 297 | RNF38 | 6.48E−17 | −0.441081552 | 0.022 | 0.037 | 4.35E−13 | Higher in Normal/Healthy Samples | II |
| 298 | UBQLN3 | 3.28E−08 | −0.445456908 | 0.007 | 0.013 | 0.00022021 | Higher in Normal/Healthy Samples | II |
| 299 | DDX20 | 1.34E−10 | −0.445796799 | 0.008 | 0.015 | 8.96E−07 | Higher in Normal/Healthy Samples | II |
| 300 | CCDC169 | 2.05E−13 | −0.446394184 | 0.007 | 0.015 | 1.37E−09 | Higher in Normal/Healthy Samples | II |
| 301 | PARP6 | 1.71E−08 | −0.449586156 | 0.006 | 0.011 | 0.00011454 | Higher in Normal/Healthy Samples | II |
| 302 | PODXL2 | 1.77E−08 | −0.450414673 | 0.008 | 0.014 | 0.00011871 | Higher in Normal/Healthy Samples | II |
| 303 | RAB11FIP5 | 1.74E−12 | −0.450868306 | 0.014 | 0.024 | 1.17E−08 | Higher in Normal/Healthy Samples | II |
| 304 | PDXK | 3.52E−11 | −0.452905241 | 0.018 | 0.028 | 2.36E−07 | Higher in Normal/Healthy Samples | II |
| 305 | PPDPF | 3.32E−15 | −0.455520016 | 0.019 | 0.032 | 2.23E−11 | Higher in Normal/Healthy Samples | II |
| 306 | FAM217A | 8.22E−12 | −0.458251433 | 0.006 | 0.013 | 5.51E−08 | Higher in Normal/Healthy Samples | II |
| 307 | GGN | 5.42E−08 | −0.458831863 | 0.007 | 0.013 | 0.00036352 | Higher in Normal/Healthy Samples | II |
| 308 | GABRG3-AS1 | 6.52E−14 | −0.458893334 | 0.011 | 0.021 | 4.37E−10 | Higher in Normal/Healthy Samples | II |
| 309 | RPS15 | 5.89E−07 | −0.45938237 | 0.01 | 0.016 | 0.00395079 | Higher in Normal/Healthy Samples | II |
| 310 | TPI1 | 9.95E−22 | −0.463917552 | 0.024 | 0.042 | 6.67E−18 | Higher in Normal/Healthy Samples | II |
| 311 | AZIN2 | 9.14E−14 | −0.463988282 | 0.013 | 0.023 | 6.12E−10 | Higher in Normal/Healthy Samples | II |
| 312 | RBCK1 | 6.09E−08 | −0.467158496 | 0.007 | 0.013 | 0.0004084 | Higher in Normal/Healthy Samples | II |
| 313 | DPP7 | 8.64E−16 | −0.468283511 | 0.02 | 0.034 | 5.79E−12 | Higher in Normal/Healthy Samples | II |
| 314 | MLF1 | 2.52E−16 | −0.468306273 | 0.014 | 0.026 | 1.69E−12 | Higher in Normal/Healthy Samples | II |
| 315 | ELOF1 | 2.62E−14 | −0.471507045 | 0.018 | 0.03 | 1.76E−10 | Higher in Normal/Healthy Samples | II |
| 316 | PDXDC1 | 2.70E−09 | −0.471894075 | 0.006 | 0.012 | 1.81E−05 | Higher in Normal/Healthy Samples | II |
| 317 | KTN1 | 2.47E−12 | −0.478796917 | 0.006 | 0.013 | 1.65E−08 | Higher in Normal/Healthy Samples | II |
| 318 | ICA1 | 1.54E−13 | −0.481573936 | 0.007 | 0.015 | 1.03E−09 | Higher in Normal/Healthy Samples | II |
| 319 | OPLAH | 4.39E−10 | −0.484188344 | 0.014 | 0.022 | 2.95E−06 | Higher in Normal/Healthy Samples | II |
| 320 | BZW1 | 4.92E−13 | −0.486297964 | 0.004 | 0.011 | 3.30E−09 | Higher in Normal/Healthy Samples | II |
| 321 | RAD21 | 3.13E−16 | −0.498489193 | 0.012 | 0.023 | 2.10E−12 | Higher in Normal/Healthy Samples | II |
| 322 | SPZ1 | 1.18E−16 | −0.502456893 | 0.013 | 0.024 | 7.91E−13 | Higher in Normal/Healthy Samples | II |
| 323 | RTN4 | 6.64E−22 | −0.50292602 | 0.015 | 0.03 | 4.45E−18 | Higher in Normal/Healthy Samples | II |
| 324 | CDIPT-AS1 | 7.68E−10 | −0.505475462 | 0.008 | 0.015 | 5.15E−06 | Higher in Normal/Healthy Samples | II |
| 325 | SHARPIN | 3.27E−23 | −0.512428508 | 0.025 | 0.044 | 2.19E−19 | Higher in Normal/Healthy Samples | II |
| 326 | ZFAND3 | 1.32E−15 | −0.515371447 | 0.007 | 0.015 | 8.82E−12 | Higher in Normal/Healthy Samples | II |
| 327 | ARF1 | 4.41E−12 | −0.516942297 | 0.006 | 0.013 | 2.95E−08 | Higher in Normal/Healthy Samples | II |
| 328 | FNDC8 | 2.24E−10 | −0.517470332 | 0.005 | 0.011 | 1.50E−06 | Higher in Normal/Healthy Samples | II |
| 329 | TOLLIP | 3.13E−11 | −0.517906549 | 0.006 | 0.013 | 2.10E−07 | Higher in Normal/Healthy Samples | II |
| 330 | MIS12 | 1.90E−13 | −0.518240755 | 0.006 | 0.014 | 1.27E−09 | Higher in Normal/Healthy Samples | II |
| 331 | ATAD1 | 2.49E−14 | −0.520866093 | 0.007 | 0.015 | 1.67E−10 | Higher in Normal/Healthy Samples | II |
| 332 | MEIOC | 4.49E−18 | −0.522855397 | 0.014 | 0.027 | 3.01E−14 | Higher in Normal/Healthy Samples | II |
| 333 | RP11-2C24.7 | 1.80E−14 | −0.524423913 | 0.005 | 0.013 | 1.21E−10 | Higher in Normal/Healthy Samples | II |
| 334 | CCDC187 | 6.64E−16 | −0.527693332 | 0.017 | 0.03 | 4.45E−12 | Higher in Normal/Healthy Samples | II |
| 335 | CTSF | 1.74E−13 | −0.531325855 | 0.011 | 0.021 | 1.17E−09 | Higher in Normal/Healthy Samples | II |
| 336 | SPPL2B | 1.64E−09 | −0.535132151 | 0.006 | 0.012 | 1.10E−05 | Higher in Normal/Healthy Samples | II |
| 337 | TTLL10 | 5.96E−14 | −0.536910393 | 0.009 | 0.018 | 4.00E−10 | Higher in Normal/Healthy Samples | II |

TABLE 3-continued

Tier 2 genes (ranked by Average log Fold Change (avg_logFC)).

| | GeneName | p_val | avg_logFC | pct.1 | pct.2 | p_val_adj | Marker Type | Tier |
|---|---|---|---|---|---|---|---|---|
| 338 | HAGLR | 1.00E-12 | -0.545928865 | 0.007 | 0.014 | 6.73E-09 | Higher in Normal/Healthy Samples | II |
| 339 | CCHCR1 | 1.32E-12 | -0.546192185 | 0.004 | 0.011 | 8.83E-09 | Higher in Normal/Healthy Samples | II |
| 340 | CYB5R4 | 6.37E-19 | -0.546412624 | 0.012 | 0.024 | 4.27E-15 | Higher in Normal/Healthy Samples | II |
| 341 | FBXL13 | 3.70E-12 | -0.547559543 | 0.005 | 0.011 | 2.48E-08 | Higher in Normal/Healthy Samples | II |
| 342 | CCDC7.1 | 1.18E-11 | -0.547607733 | 0.005 | 0.011 | 7.89E-08 | Higher in Normal/Healthy Samples | II |
| 343 | RPS9 | 1.92E-11 | -0.550260955 | 0.005 | 0.011 | 1.29E-07 | Higher in Normal/Healthy Samples | II |
| 344 | CABS1 | 3.18E-33 | -0.551227184 | 0.025 | 0.049 | 2.13E-29 | Higher in Normal/Healthy Samples | II |
| 345 | RNF11 | 3.45E-13 | -0.551680578 | 0.005 | 0.011 | 2.32E-09 | Higher in Normal/Healthy Samples | II |
| 346 | FAM104A | 5.38E-13 | -0.552892562 | 0.006 | 0.013 | 3.60E-09 | Higher in Normal/Healthy Samples | II |
| 347 | EIF5 | 7.99E-16 | -0.553323138 | 0.008 | 0.017 | 5.35E-12 | Higher in Normal/Healthy Samples | II |
| 348 | DYRK1B | 1.10E-23 | -0.553856835 | 0.02 | 0.037 | 7.36E-20 | Higher in Normal/Healthy Samples | II |
| 349 | ZMYM2 | 1.72E-13 | -0.556414884 | 0.005 | 0.012 | 1.15E-09 | Higher in Normal/Healthy Samples | II |
| 350 | C21orf2 | 1.15E-10 | -0.559495438 | 0.005 | 0.011 | 7.68E-07 | Higher in Normal/Healthy Samples | II |
| 351 | DDX3Y | 3.49E-17 | -0.559789178 | 0.007 | 0.017 | 2.34E-13 | Higher in Normal/Healthy Samples | II |
| 352 | C1orf159 | 4.93E-10 | -0.560924279 | 0.005 | 0.011 | 3.31E-06 | Higher in Normal/Healthy Samples | II |
| 353 | DNAJC18 | 5.22E-18 | -0.562321014 | 0.011 | 0.023 | 3.50E-14 | Higher in Normal/Healthy Samples | II |
| 354 | ZDHHC3 | 1.02E-23 | -0.562681815 | 0.015 | 0.03 | 6.87E-20 | Higher in Normal/Healthy Samples | II |
| 355 | IL13 | 1.45E-15 | -0.563000324 | 0.008 | 0.017 | 9.74E-12 | Higher in Normal/Healthy Samples | II |
| 356 | GINM1 | 6.27E-16 | -0.563723407 | 0.007 | 0.016 | 4.20E-12 | Higher in Normal/Healthy Samples | II |
| 357 | CDV3 | 1.91E-16 | -0.566323802 | 0.006 | 0.015 | 1.28E-12 | Higher in Normal/Healthy Samples | II |
| 358 | ZFAND4 | 1.04E-15 | -0.567885943 | 0.005 | 0.012 | 7.00E-12 | Higher in Normal/Healthy Samples | II |
| 359 | C12orf75 | 1.59E-14 | -0.56993021 | 0.004 | 0.011 | 1.06E-10 | Higher in Normal/Healthy Samples | II |
| 360 | CCPG1 | 1.43E-13 | -0.578194996 | 0.005 | 0.012 | 9.60E-10 | Higher in Normal/Healthy Samples | II |
| 361 | STK35 | 2.70E-15 | -0.57939314 | 0.004 | 0.011 | 1.81E-11 | Higher in Normal/Healthy Samples | II |
| 362 | AF131216.1 | 1.61E-19 | -0.579629874 | 0.011 | 0.023 | 1.08E-15 | Higher in Normal/Healthy Samples | II |
| 363 | FAM76B | 1.86E-14 | -0.583938981 | 0.006 | 0.013 | 1.24E-10 | Higher in Normal/Healthy Samples | II |
| 364 | FAM234A | 2.99E-14 | -0.585401482 | 0.006 | 0.013 | 2.00E-10 | Higher in Normal/Healthy Samples | II |
| 365 | PSMF1 | 1.56E-17 | -0.58803575 | 0.008 | 0.018 | 1.04E-13 | Higher in Normal/Healthy Samples | II |
| 366 | TEX38 | 5.91E-30 | -0.588121021 | 0.023 | 0.044 | 3.96E-26 | Higher in Normal/Healthy Samples | II |
| 367 | GTSF1 | 2.18E-15 | -0.588296105 | 0.005 | 0.013 | 1.46E-11 | Higher in Normal/Healthy Samples | II |
| 368 | VPRBP | 4.18E-18 | -0.589077934 | 0.008 | 0.018 | 2.80E-14 | Higher in Normal/Healthy Samples | II |
| 369 | RNF32 | 7.79E-17 | -0.589642772 | 0.006 | 0.014 | 5.22E-13 | Higher in Normal/Healthy Samples | II |
| 370 | LCA5L | 9.01E-16 | -0.5991473 | 0.004 | 0.011 | 6.04E-12 | Higher in Normal/Healthy Samples | II |
| 371 | RPL41 | 7.36E-10 | -0.602499287 | 0.006 | 0.013 | 4.93E-06 | Higher in Normal/Healthy Samples | II |
| 372 | CYB5R2 | 2.79E-14 | -0.604836386 | 0.004 | 0.011 | 1.87E-10 | Higher in Normal/Healthy Samples | II |
| 373 | MROH7 | 2.34E-23 | -0.612039307 | 0.014 | 0.029 | 1.57E-19 | Higher in Normal/Healthy Samples | II |
| 374 | TSPAN16 | 9.70E-14 | -0.615162565 | 0.008 | 0.016 | 6.50E-10 | Higher in Normal/Healthy Samples | II |
| 375 | LRTOMT | 2.66E-25 | -0.618325887 | 0.015 | 0.031 | 1.78E-21 | Higher in Normal/Healthy Samples | II |
| 376 | AHCY | 8.35E-14 | -0.619852266 | 0.005 | 0.013 | 5.60E-10 | Higher in Normal/Healthy Samples | II |
| 377 | EGLN2 | 2.27E-27 | -0.619961779 | 0.02 | 0.039 | 1.52E-23 | Higher in Normal/Healthy Samples | II |
| 378 | AC012594.1 | 1.04E-27 | -0.621303579 | 0.014 | 0.031 | 6.95E-24 | Higher in Normal/Healthy Samples | II |
| 379 | USPL1 | 1.95E-18 | -0.627884464 | 0.005 | 0.014 | 1.31E-14 | Higher in Normal/Healthy Samples | II |
| 380 | DDX3X | 2.99E-39 | -0.634046314 | 0.022 | 0.047 | 2.01E-35 | Higher in Normal/Healthy Samples | II |
| 381 | ITCH | 7.39E-21 | -0.634068867 | 0.007 | 0.017 | 4.95E-17 | Higher in Normal/Healthy Samples | II |
| 382 | WBP2NL | 1.11E-30 | -0.634490865 | 0.017 | 0.037 | 7.44E-27 | Higher in Normal/Healthy Samples | II |
| 383 | RPL19 | 7.38E-15 | -0.634607289 | 0.005 | 0.013 | 4.94E-11 | Higher in Normal/Healthy Samples | II |
| 384 | CAMLG | 1.91E-16 | -0.63864688 | 0.004 | 0.012 | 1.28E-12 | Higher in Normal/Healthy Samples | II |
| 385 | NBR1 | 1.81E-21 | -0.643406974 | 0.005 | 0.016 | 1.21E-17 | Higher in Normal/Healthy Samples | II |
| 386 | ARHGAP5 | 1.71E-22 | -0.644672655 | 0.006 | 0.016 | 1.15E-18 | Higher in Normal/Healthy Samples | II |
| 387 | RAB3IP | 4.25E-35 | -0.645173704 | 0.016 | 0.037 | 2.85E-31 | Higher in Normal/Healthy Samples | II |
| 388 | IGSF11-AS1 | 1.47E-28 | -0.645377162 | 0.014 | 0.031 | 9.84E-25 | Higher in Normal/Healthy Samples | II |
| 389 | SERF2 | 1.27E-14 | -0.648709055 | 0.008 | 0.017 | 8.55E-11 | Higher in Normal/Healthy Samples | II |
| 390 | C6orf201 | 4.18E-23 | -0.649507823 | 0.008 | 0.021 | 2.80E-19 | Higher in Normal/Healthy Samples | II |
| 391 | COL9A3 | 1.91E-26 | -0.651253332 | 0.014 | 0.031 | 1.28E-22 | Higher in Normal/Healthy Samples | II |
| 392 | BRWD1-AS2 | 9.00E-26 | -0.651681402 | 0.017 | 0.033 | 6.03E-22 | Higher in Normal/Healthy Samples | II |
| 393 | CENPU | 1.28E-29 | -0.656745531 | 0.012 | 0.028 | 8.58E-26 | Higher in Normal/Healthy Samples | II |
| 394 | TMEM215 | 2.44E-19 | -0.658600799 | 0.007 | 0.017 | 1.63E-15 | Higher in Normal/Healthy Samples | II |
| 395 | STT3B | 1.25E-18 | -0.662526501 | 0.004 | 0.012 | 8.37E-15 | Higher in Normal/Healthy Samples | II |
| 396 | DHX57 | 6.71E-23 | -0.667565958 | 0.008 | 0.02 | 4.50E-19 | Higher in Normal/Healthy Samples | II |
| 397 | RMND5B | 9.28E-20 | -0.669443993 | 0.007 | 0.018 | 6.22E-16 | Higher in Normal/Healthy Samples | II |
| 398 | SKP1 | 4.85E-38 | -0.671382891 | 0.022 | 0.047 | 3.25E-34 | Higher in Normal/Healthy Samples | II |
| 399 | SLC25A39 | 7.49E-24 | -0.672533788 | 0.01 | 0.023 | 5.02E-20 | Higher in Normal/Healthy Samples | II |
| 400 | CFAP221 | 4.75E-18 | -0.675437954 | 0.003 | 0.011 | 3.18E-14 | Higher in Normal/Healthy Samples | II |
| 401 | PHACTR2-AS1 | 1.15E-18 | -0.67665738 | 0.004 | 0.013 | 7.70E-15 | Higher in Normal/Healthy Samples | II |
| 402 | ZDHHC19 | 4.28E-24 | -0.677790839 | 0.009 | 0.023 | 2.87E-20 | Higher in Normal/Healthy Samples | II |
| 403 | RPL15 | 8.00E-19 | -0.679301621 | 0.006 | 0.015 | 5.36E-15 | Higher in Normal/Healthy Samples | II |
| 404 | ISG20L2 | 3.04E-36 | -0.681951911 | 0.02 | 0.042 | 2.04E-32 | Higher in Normal/Healthy Samples | II |
| 405 | ESPN | 6.16E-20 | -0.682988965 | 0.01 | 0.021 | 4.13E-16 | Higher in Normal/Healthy Samples | II |
| 406 | PRKCZ | 2.48E-20 | -0.683675451 | 0.006 | 0.016 | 1.66E-16 | Higher in Normal/Healthy Samples | II |
| 407 | COPS5 | 3.52E-17 | -0.684744127 | 0.004 | 0.011 | 2.36E-13 | Higher in Normal/Healthy Samples | II |
| 408 | TSPAN1 | 5.09E-22 | -0.685070602 | 0.006 | 0.017 | 3.41E-18 | Higher in Normal/Healthy Samples | II |
| 409 | ZNF688 | 7.07E-27 | -0.69087381 | 0.01 | 0.025 | 4.74E-23 | Higher in Normal/Healthy Samples | II |
| 410 | RP11-73G16.3 | 1.23E-16 | -0.691562484 | 0.004 | 0.011 | 8.23E-13 | Higher in Normal/Healthy Samples | II |

TABLE 3-continued

Tier 2 genes (ranked by Average log Fold Change (avg_logFC)).

|     | GeneName | p_val | avg_logFC | pct.1 | pct.2 | p_val_adj | Marker Type | Tier |
| --- | --- | --- | --- | --- | --- | --- | --- | --- |
| 411 | DCAF10 | 1.09E−18 | −0.695355785 | 0.003 | 0.011 | 7.28E−15 | Higher in Normal/Healthy Samples | II |
| 412 | C17orf50 | 3.21E−18 | −0.695631494 | 0.006 | 0.016 | 2.15E−14 | Higher in Normal/Healthy Samples | II |
| 413 | YPEL5 | 1.55E−25 | −0.696578764 | 0.011 | 0.025 | 1.04E−21 | Higher in Normal/Healthy Samples | II | p_val = p value;
pct.1 = percent of cells in autism sample
pct.2 = percent of cells in normal sample

TABLE 4

Tier 1 genes (ranked by pct.1 = percent of cells in autism sample).

|    | GeneName | p_val | avg_logFC | pct.1 | pct.2 | p_val_adj | Marker Type | Tier |
| --- | --- | --- | --- | --- | --- | --- | --- | --- |
| 1 | BACE1-AS | 3.02E−252 | 2.69943217 | 0.053 | 0 | 2.02E−248 | Higher in Autistic Samples | I |
| 2 | UNC119B | 4.96E−212 | 2.15807648 | 0.053 | 0.003 | 3.32E−208 | Higher in Autistic Samples | I |
| 3 | RP11-338I21.1 | 3.66E−204 | 2.03741605 | 0.055 | 0.004 | 2.45E−200 | Higher in Autistic Samples | I |
| 4 | TIGAR | 5.68E−217 | 1.57265589 | 0.079 | 0.014 | 3.81E−213 | Higher in Autistic Samples | I |
| 5 | TPCN1 | 9.43E−153 | 1.52579159 | 0.051 | 0.007 | 6.32E−149 | Higher in Autistic Samples | I |
| 6 | RP11-567M16.6 | 4.94E−155 | 1.44823789 | 0.059 | 0.011 | 3.31E−151 | Higher in Autistic Samples | I |
| 7 | CAHM | 1.03E−155 | 1.41078764 | 0.06 | 0.011 | 6.92E−152 | Higher in Autistic Samples | I |
| 8 | EVX1-AS | 5.04E−210 | 1.28028931 | 0.094 | 0.022 | 3.38E−206 | Higher in Autistic Samples | I |
| 9 | CDIPT | 1.46E−153 | 1.23227388 | 0.071 | 0.017 | 9.80E−150 | Higher in Autistic Samples | I |
| 10 | RP11-991C1.2 | 3.40E−129 | 1.2240326 | 0.058 | 0.013 | 2.28E−125 | Higher in Autistic Samples | I |
| 11 | CLCN3 | 7.10E−228 | 1.19956391 | 0.119 | 0.034 | 4.76E−224 | Higher in Autistic Samples | I |
| 12 | GABARAPL1 | 1.43E−222 | 1.18890115 | 0.114 | 0.032 | 9.61E−219 | Higher in Autistic Samples | I |
| 13 | ATF3 | 8.08E−194 | 1.17842018 | 0.093 | 0.023 | 5.42E−190 | Higher in Autistic Samples | I |
| 14 | CTD-2196E14.5 | 5.65E−135 | 1.15666112 | 0.062 | 0.015 | 3.79E−131 | Higher in Autistic Samples | I |
| 15 | CSTL1 | 6.31E−217 | 1.13537488 | 0.115 | 0.033 | 4.23E−213 | Higher in Autistic Samples | I |
| 16 | EFCAB12 | 9.49E−174 | 1.11100499 | 0.092 | 0.026 | 6.36E−170 | Higher in Autistic Samples | I |
| 17 | VGLL3 | 3.70E−171 | 1.10310738 | 0.096 | 0.029 | 2.48E−167 | Higher in Autistic Samples | I |
| 18 | HSPB6 | 5.21E−272 | 1.09876061 | 0.148 | 0.044 | 3.49E−268 | Higher in Autistic Samples | I |
| 19 | TMSB4X | 5.05E−172 | 1.05244275 | 0.1 | 0.031 | 3.39E−168 | Higher in Autistic Samples | I |
| 20 | KDM2B | 1.05E−105 | 1.05085169 | 0.058 | 0.017 | 7.01E−102 | Higher in Autistic Samples | I |
| 21 | SORCS3-AS1 | 3.01E−157 | 1.02011787 | 0.103 | 0.036 | 2.02E−153 | Higher in Autistic Samples | I |
| 22 | RP11-140K17.3 | 1.43E−132 | 0.97418834 | 0.081 | 0.026 | 9.60E−129 | Higher in Autistic Samples | I |
| 23 | GLRX2 | 2.18E−241 | 0.97103377 | 0.171 | 0.064 | 1.46E−237 | Higher in Autistic Samples | I |
| 24 | DAG1 | 0 | 0.95419564 | 0.212 | 0.077 | 0 | Higher in Autistic Samples | I |
| 25 | WDR20 | 2.29E−124 | 0.95414166 | 0.087 | 0.031 | 1.53E−120 | Higher in Autistic Samples | I |
| 26 | DHDDS | 1.11E−92 | 0.9325072 | 0.059 | 0.02 | 7.41E−89 | Higher in Autistic Samples | I |
| 27 | LRRC52 | 3.01E−116 | 0.9320726 | 0.076 | 0.026 | 2.02E−112 | Higher in Autistic Samples | I |
| 28 | MIR762HG | 4.94E−226 | 0.89464445 | 0.171 | 0.066 | 3.31E−222 | Higher in Autistic Samples | I |
| 29 | RP11-315I20.1 | 9.52E−74 | 0.81224041 | 0.057 | 0.022 | 6.38E−70 | Higher in Autistic Samples | I |
| 30 | TADA2A | 3.27E−90 | 0.74340972 | 0.078 | 0.032 | 2.19E−86 | Higher in Autistic Samples | I |
| 31 | MEST | 8.32E−68 | 0.71354339 | 0.063 | 0.027 | 5.58E−64 | Higher in Autistic Samples | I |
| 32 | RP11-480I12.10 | 3.78E−59 | 0.68708428 | 0.053 | 0.022 | 2.54E−55 | Higher in Autistic Samples | I |
| 33 | TMCO2 | 2.87E−71 | 0.67872596 | 0.088 | 0.044 | 1.92E−67 | Higher in Autistic Samples | I |
| 34 | ZFP36L1 | 2.05E−74 | 0.67610838 | 0.081 | 0.037 | 1.37E−70 | Higher in Autistic Samples | I |
| 35 | ATP1B3 | 1.83E−173 | 0.64339015 | 0.221 | 0.115 | 1.23E−169 | Higher in Autistic Samples | I |
| 36 | CRAMP1 | 1.19E−67 | 0.60669297 | 0.081 | 0.039 | 7.96E−64 | Higher in Autistic Samples | I |
| 37 | SPTY2D1-AS1 | 1.38E−92 | 0.59500785 | 0.156 | 0.09 | 9.25E−89 | Higher in Autistic Samples | I |
| 38 | TNP1 | 5.14E−125 | 0.59133532 | 0.199 | 0.112 | 3.44E−121 | Higher in Autistic Samples | I |
| 39 | AC007557.1 | 3.02E−99 | 0.59123502 | 0.153 | 0.084 | 2.02E−95 | Higher in Autistic Samples | I |
| 40 | ACAP1 | 3.36E−31 | 0.57124888 | 0.051 | 0.028 | 2.25E−27 | Higher in Autistic Samples | I |
| 41 | MARCKS | 7.66E−77 | 0.52885638 | 0.127 | 0.071 | 5.13E−73 | Higher in Autistic Samples | I |
| 42 | CTD-2568A17.1 | 1.85E−40 | 0.35883504 | 0.175 | 0.128 | 1.24E−36 | Higher in Autistic Samples | I |
| 43 | PRM1 | 5.95E−194 | 0.3057173 | 0.665 | 0.537 | 3.99E−190 | Higher in Autistic Samples | I |
| 44 | TCEB2 | 5.52E−14 | 0.27295501 | 0.066 | 0.048 | 3.70E−10 | Higher in Autistic Samples | I |
| 45 | TMEM31 | 6.82E−06 | 0.17468959 | 0.064 | 0.053 | 0.045728194 | Higher in Autistic Samples | I |
| 46 | MEX3D | 9.56E−06 | 0.09287349 | 0.142 | 0.126 | 0.064110994 | Higher in Autistic Samples | I |
| 47 | PHOSPHO1 | 8.73E−08 | −0.1908199 | 0.096 | 0.112 | 0.000585029 | Higher in Normal/Healthy Samples | I |
| 48 | ETNK2 | 5.40E−08 | −0.1960796 | 0.054 | 0.067 | 0.000362253 | Higher in Normal/Healthy Samples | I |
| 49 | SLC39A13 | 5.79E−05 | −0.2065259 | 0.044 | 0.053 | 0.38792739 | Higher in Normal/Healthy Samples | I |
| 50 | C17orf74 | 1.83E−09 | −0.2123785 | 0.074 | 0.091 | 1.23E−05 | Higher in Normal/Healthy Samples | I |
| 51 | DGCR6L | 2.33E−13 | −0.2124644 | 0.139 | 0.165 | 1.56E−09 | Higher in Normal/Healthy Samples | I |
| 52 | CRIP2 | 1.97E−05 | −0.217182 | 0.042 | 0.051 | 0.132077564 | Higher in Normal/Healthy Samples | I |
| 53 | ODF3L2 | 2.70E−09 | −0.2412868 | 0.066 | 0.082 | 1.81E−05 | Higher in Normal/Healthy Samples | I |
| 54 | CIB1 | 1.28E−12 | −0.2424624 | 0.075 | 0.095 | 8.59E−09 | Higher in Normal/Healthy Samples | I |
| 55 | NUPR2 | 4.93E−94 | −0.3259469 | 0.349 | 0.44 | 3.31E−90 | Higher in Normal/Healthy Samples | I |
| 56 | C16orf82 | 5.81E−32 | −0.3277931 | 0.089 | 0.127 | 3.89E−28 | Higher in Normal/Healthy Samples | I |
| 57 | UBXN6 | 1.51E−14 | −0.3307218 | 0.047 | 0.065 | 1.01E−10 | Higher in Normal/Healthy Samples | I |
| 58 | DNAJC4 | 7.46E−54 | −0.3425147 | 0.213 | 0.275 | 5.00E−50 | Higher in Normal/Healthy Samples | I |
| 59 | UBA52 | 1.65E−26 | −0.3675711 | 0.082 | 0.114 | 1.11E−22 | Higher in Normal/Healthy Samples | I |
| 60 | REEP6 | 6.29E−35 | −0.4119588 | 0.082 | 0.12 | 4.22E−31 | Higher in Normal/Healthy Samples | I |

TABLE 4-continued

Tier 1 genes (ranked by pct.1 = percent of cells in autism sample).

|    | GeneName | p_val | avg_logFC | pct.1 | pct.2 | p_val_adj | Marker Type | Tier |
|----|----------|-------|-----------|-------|-------|-----------|-------------|------|
| 61 | LELP1 | 2.83E−64 | −0.4189181 | 0.137 | 0.202 | 1.90E−60 | Higher in Normal/Healthy Samples | I |
| 62 | RANGAP1 | 9.28E−27 | −0.4326911 | 0.051 | 0.078 | 6.22E−23 | Higher in Normal/Healthy Samples | I |
| 63 | TNFAIP8L1 | 2.02E−20 | −0.4416062 | 0.035 | 0.055 | 1.36E−16 | Higher in Normal/Healthy Samples | I |
| 64 | ARL4A | 3.24E−46 | −0.4560769 | 0.047 | 0.084 | 2.17E−42 | Higher in Normal/Healthy Samples | I |
| 65 | PRM2 | 0 | −0.4714612 | 0.771 | 0.888 | 0 | Higher in Normal/Healthy Samples | I |
| 66 | TPGS2 | 1.19E−31 | −0.4824332 | 0.043 | 0.071 | 7.96E−28 | Higher in Normal/Healthy Samples | I |
| 67 | CSNK1G2 | 2.54E−30 | −0.5031487 | 0.036 | 0.062 | 1.70E−26 | Higher in Normal/Healthy Samples | I |
| 68 | LPIN1 | 2.29E−32 | −0.5060187 | 0.03 | 0.055 | 1.54E−28 | Higher in Normal/Healthy Samples | I |
| 69 | ZNHIT2 | 2.10E−26 | −0.5087596 | 0.034 | 0.057 | 1.41E−22 | Higher in Normal/Healthy Samples | I |
| 70 | PCSK4 | 8.83E−38 | −0.5090088 | 0.058 | 0.093 | 5.92E−34 | Higher in Normal/Healthy Samples | I |
| 71 | PCYT2 | 4.06E−78 | −0.5132676 | 0.116 | 0.183 | 2.72E−74 | Higher in Normal/Healthy Samples | I |
| 72 | OAZ3 | 7.74E−32 | −0.5320387 | 0.029 | 0.053 | 5.19E−28 | Higher in Normal/Healthy Samples | I |
| 73 | TPPP2 | 2.04E−40 | −0.5489612 | 0.038 | 0.069 | 1.37E−36 | Higher in Normal/Healthy Samples | I |
| 74 | SMCP | 4.80E−251 | −0.5590082 | 0.319 | 0.469 | 3.22E−247 | Higher in Normal/Healthy Samples | I |
| 75 | FBXW5 | 3.86E−62 | −0.5606896 | 0.073 | 0.123 | 2.59E−58 | Higher in Normal/Healthy Samples | I |
| 76 | TCP11 | 5.93E−53 | −0.5654578 | 0.046 | 0.085 | 3.97E−49 | Higher in Normal/Healthy Samples | I |
| 77 | BOD1L2 | 2.80E−75 | −0.5694686 | 0.064 | 0.119 | 1.88E−71 | Higher in Normal/Healthy Samples | I |
| 78 | CARHSP1 | 5.92E−119 | −0.5893111 | 0.126 | 0.214 | 3.97E−115 | Higher in Normal/Healthy Samples | I |
| 79 | GLUL | 2.99E−103 | −0.6325155 | 0.088 | 0.161 | 2.01E−99 | Higher in Normal/Healthy Samples | I |
| 80 | C2orf57 | 3.94E−43 | −0.640038 | 0.03 | 0.06 | 2.64E−39 | Higher in Normal/Healthy Samples | I |
| 81 | SMKR1 | 5.78E−97 | −0.6523097 | 0.06 | 0.122 | 3.88E−93 | Higher in Normal/Healthy Samples | I |
| 82 | PTP4A1 | 1.21E−72 | −0.6592552 | 0.048 | 0.097 | 8.11E−69 | Higher in Normal/Healthy Samples | I |
| 83 | CCSER2 | 3.15E−48 | −0.6593097 | 0.024 | 0.054 | 2.11E−44 | Higher in Normal/Healthy Samples | I |
| 84 | AQP5 | 3.83E−69 | −0.6728068 | 0.049 | 0.095 | 2.57E−65 | Higher in Normal/Healthy Samples | I |
| 85 | MPC2 | 2.68E−63 | −0.6794335 | 0.036 | 0.075 | 1.80E−59 | Higher in Normal/Healthy Samples | I |
| 86 | RGS22 | 3.68E−67 | −0.6797034 | 0.039 | 0.081 | 2.47E−63 | Higher in Normal/Healthy Samples | I |
| 87 | PKM | 2.27E−48 | −0.6916785 | 0.032 | 0.064 | 1.52E−44 | Higher in Normal/Healthy Samples | I |
| 88 | MOSPD3 | 2.41E−63 | −0.6999246 | 0.046 | 0.089 | 1.61E−59 | Higher in Normal/Healthy Samples | I |
| 89 | RPL13 | 5.40E−42 | −0.7040074 | 0.025 | 0.052 | 3.62E−38 | Higher in Normal/Healthy Samples | I |
| 90 | SH3GL3 | 8.54E−64 | −0.7163834 | 0.033 | 0.072 | 5.73E−60 | Higher in Normal/Healthy Samples | I |
| 91 | CXCL16 | 5.22E−104 | −0.7189309 | 0.068 | 0.134 | 3.50E−100 | Higher in Normal/Healthy Samples | I |
| 92 | TSPAN6 | 5.77E−148 | −0.748282 | 0.076 | 0.163 | 3.87E−144 | Higher in Normal/Healthy Samples | I |
| 93 | CCNY | 2.96E−98 | −0.7583202 | 0.045 | 0.102 | 1.98E−94 | Higher in Normal/Healthy Samples | I |
| 94 | PROCA1 | 8.46E−124 | −0.8214334 | 0.054 | 0.124 | 5.67E−120 | Higher in Normal/Healthy Samples | I |
| 95 | ABHD1 | 3.73E−91 | −0.8308931 | 0.041 | 0.093 | 2.50E−87 | Higher in Normal/Healthy Samples | I |
| 96 | TSSK6 | 0 | −0.8404547 | 0.258 | 0.472 | 0 | Higher in Normal/Healthy Samples | I |
| 97 | FKBP8 | 4.42E−73 | −0.8717067 | 0.024 | 0.061 | 2.96E−69 | Higher in Normal/Healthy Samples | I |
| 98 | MFF | 8.62E−87 | −0.8825129 | 0.028 | 0.073 | 5.78E−83 | Higher in Normal/Healthy Samples | I |
| 99 | GNAS | 2.47E−80 | −0.8930704 | 0.026 | 0.067 | 1.65E−76 | Higher in Normal/Healthy Samples | I |
| 100 | SPATA18 | 1.06E−74 | −0.9236969 | 0.018 | 0.053 | 7.12E−71 | Higher in Normal/Healthy Samples | I |
| 101 | TSSK2 | 2.65E−101 | −0.9244019 | 0.032 | 0.083 | 1.77E−97 | Higher in Normal/Healthy Samples | I |
| 102 | ACSBG2 | 1.79E−89 | −0.9764337 | 0.019 | 0.06 | 1.20E−85 | Higher in Normal/Healthy Samples | I |
| 103 | PAFAH1B1 | 4.00E−96 | −1.0045238 | 0.019 | 0.062 | 2.68E−92 | Higher in Normal/Healthy Samples | I |
| 104 | GAPDH | 1.28E−112 | −1.0575774 | 0.025 | 0.077 | 8.55E−109 | Higher in Normal/Healthy Samples | I |
| 105 | CCDC91 | 5.76E−184 | −1.1119456 | 0.034 | 0.113 | 3.86E−180 | Higher in Normal/Healthy Samples | I |
| 106 | DCUN1D1 | 1.26E−305 | −1.1444081 | 0.054 | 0.18 | 8.43E−302 | Higher in Normal/Healthy Samples | I |
| 107 | CRISP2 | 0 | −1.1621639 | 0.237 | 0.598 | 0 | Higher in Normal/Healthy Samples | I |
| 108 | VRK3 | 1.91E−114 | −1.2025322 | 0.017 | 0.064 | 1.28E−110 | Higher in Normal/Healthy Samples | I |
| 109 | AKAP1 | 5.91E−128 | −1.2360163 | 0.018 | 0.069 | 3.96E−124 | Higher in Normal/Healthy Samples | I | p_val = p value;
avg_logFC = Average log Fold Change
pct.2 = percent of cells in normal sample

TABLE 5

Genes used in the Gene Signature set part 1

|    | ID | Symbol | Entrez Gene Name | Location | Type(s) |
|----|----|--------|------------------|----------|---------|
| 1 | AACS | AACS | acetoacetyl-CoA synthetase | Cytoplasm | enzyme |
| 2 | ABHD1 | ABHD1 | abhydrolase domain containing 1 | Other | other |
| 3 | ACAP1 | ACAP1 | ArfGAP with coiled-coil, ankyrin repeat and PH domains 1 | Plasma Membr. | other |
| 4 | ACE | ACE | angiotensin I converting enzyme | Plasma Membr. | peptidase |
| 5 | ACSBG2 | ACSBG2 | acyl-CoA synthetase bubblegum family member 2 | Cytoplasm | enzyme |
| 6 | ACSS1 | ACSS1 | acyl-CoA synthetase short chain family member 1 | Cytoplasm | enzyme |
| 7 | ACTL10 | ACTL10 | actin like 10 | Extrcellr Spce | other |
| 8 | ACTL7A | ACTL7A | actin like 7A | Nucleus | other |
| 9 | ACTL7B | ACTL7B | actin like 7B | Cytoplasm | other |
| 10 | ADGRG1 | ADGRG1 | adhesion G protein-coupled receptor G1 | Plasma Membr. | G-protein coupled receptor |
| 11 | ADO | ADO | 2-aminoethanethiol dioxygenase | Cytoplasm | enzyme |
| 12 | AGAP1 | AGAP1 | ArfGAP with GTPase domain, ankyrin repeat and PH domain 1 | Cytoplasm | enzyme |

TABLE 5-continued

Genes used in the Gene Signature set part 1

| ID | Symbol | Entrez Gene Name | Location | Type(s) |
|---|---|---|---|---|
| 13 | AGPAT2 | AGPAT2 | 1-acylglycerol-3-phosphate O-acyltransferase 2 | Cytoplasm | enzyme |
| 14 | AHCY | AHCY | adenosylhomocysteinase | Cytoplasm | enzyme |
| 15 | AKAP1 | AKAP1 | A-kinase anchoring protein 1 | Cytoplasm | other |
| 16 | ANKRD12 | ANKRD12 | ankyrin repeat domain 12 | Nucleus | other |
| 17 | AP2B1 | AP2B1 | adaptor related protein complex 2 beta 1 subunit | Plasma Membr. | transporter |
| 18 | APOL6 | APOL6 | apolipoprotein L6 | Extrcellr Spce | transporter |
| 19 | APOPT1 | APOPT1 | apoptogenic 1, mitochondrial | Cytoplasm | other |
| 20 | AQP5 | AQP5 | aquaporin 5 | Plasma Membr. | transporter |
| 21 | ARF1 | ARF1 | ADP ribosylation factor 1 | Cytoplasm | enzyme |
| 22 | ARF4-AS1 | ARF4-AS1 | ADP ribosylation factor 4 | Other | other |
| 23 | ARHGAP5 | ARHGAP5 | Rho GTPase activating protein 5 | Cytoplasm | enzyme |
| 24 | ARL4A | ARL4A | ADP ribosylation factor like GTPase 4A | Nucleus | enzyme |
| 25 | ARL4C | ARL4C | ADP ribosylation factor like GTPase 4C | Nucleus | enzyme |
| 26 | ARL6IP4 | ARL6IP4 | ADP ribosylation factor like GTPase 6 interacting protein 4 | Nucleus | other |
| 27 | ATAD1 | ATAD1 | ATPase family, AAA domain containing 1 | Plasma Membr. | enzyme |
| 28 | ATF3 | ATF3 | activating transcription factor 3 | Nucleus | transcription regulator |
| 29 | ATP1B3 | ATP1B3 | ATPase Na+/K+ transporting subunit beta 3 | Plasma Membr. | transporter |
| 30 | ATP6V1A | ATP6V1A | ATPase H+ transporting V1 subunit A | Plasma Membr. | transporter |
| 31 | ATPAF1 | ATPAF1 | ATP synthase mitochondrial F1 complex assembly factor 1 | Cytoplasm | other |
| 32 | AURKAIP1 | AURKAIP1 | aurora kinase A interacting protein 1 | Nucleus | enzyme |
| 33 | AZIN2 | AZIN2 | antizyme inhibitor 2 | Cytoplasm | enzyme |
| 34 | BACE1-AS | BACE1-AS | BACE1 antisense RNA | Other | other |
| 35 | BAG5 | BAG5 | BCL2 associated athanogene 5 | Cytoplasm | other |
| 36 | BAZ1A | BAZ1A | bromodomain adjacent to zinc finger domain 1A | Nucleus | other |
| 37 | BAZ2A | BAZ2A | bromodomain adjacent to zinc finger domain 2A | Nucleus | transcription regulator |
| 38 | BOD1L2 | BOD1L2 | biorientation of chromosomes in cell division 1 like 2 | Other | other |
| 39 | BPIFA3 | BPIFA3 | BPI fold containing family A member 3 | Other | other |
| 40 | BRD2 | BRD2 | bromodomain containing 2 | Nucleus | kinase |
| 41 | BRK1 | BRK1 | BRICK1, SCAR/WAVE actin nucleating complex subunit | Cytoplasm | other |
| 42 | BRWD1-AS2 | BRWD1-AS2 | BRWD1 antisense RNA 2 | Other | other |
| 43 | BSG | BSG | basigin (Ok blood group) | Plasma Membr. | transporter |
| 44 | BZW1 | BZW1 | basic leucine zipper and W2 domains 1 | Cytoplasm | translation regulator |
| 45 | C10orf62 | C10orf62 | chromosome 10 open reading frame 62 | Other | other |
| 46 | C10orf82 | C10orf82 | chromosome 10 open reading frame 82 | Other | other |
| 47 | C10orf90 | C10orf90 | chromosome 10 open reading frame 90 | Cytoplasm | other |
| 48 | C11orf68 | C11orf68 | chromosome 11 open reading frame 68 | Other | other |
| 49 | C12orf50 | C12orf50 | chromosome 12 open reading frame 50 | Other | other |
| 50 | C12orf75 | C12orf75 | chromosome 12 open reading frame 75 | Other | other |
| 51 | C16orf82 | C16orf82 | chromosome 16 open reading frame 82 | Other | other |
| 52 | C17orf50 | C17orf50 | chromosome 17 open reading frame 50 | Other | other |
| 53 | C17orf97 | C17orf97 | chromosome 17 open reading frame 97 | Other | other |
| 54 | C1orf159 | C1orf159 | chromosome 1 open reading frame 159 | Other | other |
| 55 | C1orf43 | C1orf43 | chromosome 1 open reading frame 43 | Other | other |
| 56 | C20orf144 | C20orf144 | chromosome 20 open reading frame 144 | Other | other |
| 57 | C21orf2 | C21orf2 | chromosome 21 open reading frame 2 | Cytoplasm | other |
| 58 | C21orf91 | C21orf91 | chromosome 21 open reading frame 91 | Other | other |
| 59 | C3 | C3 | complement C3 | Extrcellr Spce | peptidase |
| 60 | C3orf22 | C3orf22 | chromosome 3 open reading frame 22 | Other | other |
| 61 | C6orf120 | C6orf120 | chromosome 6 open reading frame 120 | Cytoplasm | other |
| 62 | C6orf201 | C6orf201 | chromosome 6 open reading frame 201 | Other | other |
| 63 | C9orf16 | C9orf16 | chromosome 9 open reading frame 16 | Other | other |
| 64 | C9orf3 | C9orf3 | chromosome 9 open reading frame 3 | Cytoplasm | peptidase |
| 65 | CABS1 | CABS1 | calcium binding protein, spermatid associated 1 | Extrcellr Spce | other |
| 66 | CABYR | CABYR | calcium binding tyrosine phosphorylation regulated | Cytoplasm | other |
| 67 | CAHM | CAHM | colon adenocarcinoma hypermethylated (non-protein coding) | Other | other |
| 68 | CAMLG | CAMLG | calcium modulating ligand | Cytoplasm | other |
| 69 | CARHSP1 | CARHSP1 | calcium regulated heat stable protein 1 | Cytoplasm | other |
| 70 | CCDC136 | CCDC136 | coiled-coil domain containing 136 | Cytoplasm | other |
| 71 | CCDC155 | CCDC155 | coiled-coil domain containing 155 | Nucleus | other |
| 72 | CCDC168 | CCDC168 | coiled-coil domain containing 168 | Other | other |
| 73 | CCDC169 | CCDC169 | coiled-coil domain containing 169 | Other | other |
| 74 | CCDC187 | CCDC187 | coiled-coil domain containing 187 | Other | other |
| 75 | CCDC37-AS1 | CCDC37-AS1 | CCDC37 antisense RNA 1 (head to head) | Other | other |
| 76 | CCDC7 | CCDC7 | coiled-coil domain containing 7 | Other | other |
| 77 | CCDC80 | CCDC80 | coiled-coil domain containing 80 | Nucleus | other |
| 78 | CCDC91 | CCDC91 | coiled-coil domain containing 91 | Cytoplasm | other |
| 79 | CCHCR1 | CCHCR1 | coiled-coil alpha-helical rod protein 1 | Cytoplasm | other |
| 80 | CCNY | CCNY | cyclin Y | Nucleus | other |
| 81 | CCPG1 | CCPG1 | cell cycle progression 1 | Other | other |
| 82 | CCSER1 | CCSER1 | coiled-coil serine rich protein 1 | Other | other |
| 83 | CCSER2 | CCSER2 | coiled-coil serine rich protein 2 | Other | other |
| 84 | CDC42BPA | CDC42BPA | CDC42 binding protein kinase alpha | Cytoplasm | kinase |

TABLE 5-continued

Genes used in the Gene Signature set part 1

| ID | Symbol | Entrez Gene Name | Location | Type(s) |
|---|---|---|---|---|
| 85 CDH23 | CDH23 | cadherin related 23 | Plasma Membr. | transporter |
| 86 CDHR2 | CDHR2 | cadherin related family member 2 | Plasma Membr. | other |
| 87 CDIP1 | CDIP1 | cell death inducing p53 target 1 | Nucleus | other |
| 88 CDIPT | CDIPT | CDP-diacylglycerol--inositol 3-phosphatidyltransferase | Cytoplasm | enzyme |
| 89 CDIPT-AS1 | CDIPT-AS1 | CDIPT antisense RNA 1 (head to head) | Other | other |
| 90 CDK19 | CDK19 | cyclin dependent kinase 19 | Nucleus | kinase |
| 91 CDKN1C | CDKN1C | cyclin dependent kinase inhibitor 1C | Nucleus | other |
| 92 CDV3 | CDV3 | CDV3 homolog | Cytoplasm | other |
| 93 CENPJ | CENPJ | centromere protein J | Nucleus | transcription regulator |
| 94 CENPU | CENPU | centromere protein U | Nucleus | other |
| 95 CEP152 | CEP152 | centrosomal protein 152 | Cytoplasm | other |
| 96 CEP85L | CEP85L | centrosomal protein 85 like | Cytoplasm | other |
| 97 CFAP157 | CFAP157 | cilia and flagella associated protein 157 | Cytoplasm | other |
| 98 CFAP221 | CFAP221 | cilia and flagella associated protein 221 | Extrcellr Spce | other |
| 99 CFAP44 | CFAP44 | cilia and flagella associated protein 44 | Extrcellr Spce | other |
| 100 CFL1 | CFL1 | cofilin 1 | Nucleus | other |
| 101 CIB2 | CIB2 | calcium and integrin binding family member 2 | Plasma Membr. | kinase |
| 102 CITED4 | CITED4 | Cbp/p300 interacting transactivator with Glu/Asp rich carboxy-terminal domain 4 | Nucleus | transcription regulator |
| 103 CLCN3 | CLCN3 | chloride voltage-gated channel 3 | Plasma Membr. | ion channel |
| 104 CLIC5 | CLIC5 | chloride intracellular channel 5 | Cytoplasm | ion channel |
| 105 CLK3 | CLK3 | CDC like kinase 3 | Nucleus | kinase |
| 106 CLPB | CLPB | ClpB homolog, mitochondrial AAA ATPase chaperonin | Nucleus | transcription regulator |
| 107 CLU | CLU | clusterin | Cytoplasm | other |
| 108 COL9A3 | COL9A3 | collagen type IX alpha 3 chain | Extrcellr Spce | other |
| 109 COPS5 | COPS5 | COP9 signalosome subunit 5 | Nucleus | transcription regulator |
| 110 COX7C | COX7C | cytochrome c oxidase subunit 7C | Cytoplasm | enzyme |
| 111 COX8C | COX8C | cytochrome c oxidase subunit 8C | Cytoplasm | enzyme |
| 112 CPTP | CPTP | ceramide-1-phosphate transfer protein | Cytoplasm | transporter |
| 113 CRAMP1 | CRAMP1 | cramped chromatin regulator homolog 1 | Other | other |
| 114 CRAT | CRAT | carnitine O-acetyltransferase | Cytoplasm | enzyme |
| 115 CREB3L2 | CREB3L2 | cAMP responsive element binding protein 3 like 2 | Nucleus | transcription regulator |
| 116 CRISP2 | CRISP2 | cysteine rich secretory protein 2 | Extrcellr Spce | other |
| 117 CSNK1G2 | CSNK1G2 | casein kinase 1 gamma 2 | Cytoplasm | kinase |
| 118 CSPP1 | CSPP1 | centrosome and spindle pole associated protein 1 | Cytoplasm | other |
| 119 CSTL1 | CSTL1 | cystatin like 1 | Extrcellr Spce | other |
| 120 CTSF | CTSF | cathepsin F | Cytoplasm | peptidase |
| 121 CUL3 | CUL3 | cullin 3 | Nucleus | enzyme |
| 122 CXCL16 | CXCL16 | C-X-C motif chemokine ligand 16 | Extrcellr Spce | cytokine |
| 123 CYB5R2 | CYB5R2 | cytochrome b5 reductase 2 | Cytoplasm | enzyme |
| 124 CYB5R4 | CYB5R4 | cytochrome b5 reductase 4 | Cytoplasm | enzyme |
| 125 DAG1 | DAG1 | dystroglycan 1 | Plasma Membr. | transmembrane receptor |
| 126 VPRBP | DCAF1 | DDB1 and CUL4 associated factor 1 | Nucleus | kinase |
| 127 DCAF10 | DCAF10 | DDB1 and CUL4 associated factor 10 | Nucleus | other |
| 128 DCC | DCC | DCC netrin 1 receptor | Plasma Membr. | transmembrane receptor |
| 129 DCUN1D1 | DCUN1D1 | defective in cullin neddylation 1 domain containing 1 | Nucleus | other |
| 130 DDX20 | DDX20 | DEAD-box helicase 20 | Nucleus | transcription regulator |
| 131 DDX3X | DDX3X | DEAD-box helicase 3, X-linked | Cytoplasm | enzyme |
| 132 DDX3Y | DDX3Y | DEAD-box helicase 3, Y-linked | Cytoplasm | enzyme |
| 133 DDX5 | DDX5 | DEAD-box helicase 5 | Nucleus | enzyme |
| 134 DES | DES | desmin | Cytoplasm | other |
| 135 DGCR8 | DGCR8 | DGCR8, microprocessor complex subunit | Nucleus | enzyme |
| 136 DHDDS | DHDDS | dehydrodolichyl diphosphate synthase subunit | Cytoplasm | enzyme |
| 137 DHX57 | DHX57 | DExH-box helicase 57 | Extrcellr Spce | other |
| 138 DMWD | DMWD | DM1 locus, WD repeat containing | Nucleus | other |
| 139 DNAAF3 | DNAAF3 | dynein axonemal assembly factor 3 | Other | other |
| 140 DNAJB4 | DNAJB4 | DnaJ heat shock protein family (Hsp40) member B4 | Nucleus | other |
| 141 DNAJB7 | DNAJB7 | DnaJ heat shock protein family (Hsp40) member B7 | Other | other |
| 142 DNAJC18 | DNAJC18 | DnaJ heat shock protein family (Hsp40) member C18 | Other | enzyme |
| 143 DNAJC4 | DNAJC4 | DnaJ heat shock protein family (Hsp40) member C4 | Cytoplasm | other |
| 144 DPP3 | DPP3 | dipeptidyl peptidase 3 | Cytoplasm | peptidase |
| 145 DPP7 | DPP7 | dipeptidyl peptidase 7 | Cytoplasm | peptidase |
| 146 DUSP15 | DUSP15 | dual specificity phosphatase 15 | Cytoplasm | phosphatase |
| 147 DYNLL1 | DYNLL1 | dynein light chain LC8-type 1 | Cytoplasm | other |
| 148 DYNLL2 | DYNLL2 | dynein light chain LC8-type 2 | Cytoplasm | other |
| 149 DYRK1B | DYRK1B | dual specificity tyrosine phosphorylation regulated kinase 1B | Nucleus | kinase |
| 150 DZIP1 | DZIP1 | DAZ interacting zinc finger protein 1 | Cytoplasm | other |
| 151 EAF1 | EAF1 | ELL associated factor 1 | Nucleus | transcription regulator |
| 152 EAF1-AS1 | EAF1-AS1 | EAF1 antisense RNA 1 | Other | other |
| 153 EEF1D | EEF1D | eukaryotic translation elongation factor 1 delta | Cytoplasm | translation regulator |
| 154 EFCAB11 | EFCAB11 | EF-hand calcium binding domain 11 | Other | other |
| 155 EFCAB12 | EFCAB12 | EF-hand calcium binding domain 12 | Other | other |
| 156 EFCAB14 | EFCAB14 | EF-hand calcium binding domain 14 | Other | other |
| 157 EGLN2 | EGLN2 | egl-9 family hypoxia inducible factor 2 | Cytoplasm | enzyme |

TABLE 5-continued

Genes used in the Gene Signature set part 1

| ID | Symbol | Entrez Gene Name | Location | Type(s) |
|---|---|---|---|---|
| 158 EIF2B4 | EIF2B4 | eukaryotic translation initiation factor 2B subunit delta | Cytoplasm | other |
| 159 EIF4E | EIF4E | eukaryotic translation initiation factor 4E | Cytoplasm | translation regulator |
| 160 EIF5 | EIF5 | eukaryotic translation initiation factor 5 | Cytoplasm | translation regulator |
| 161 EIF5A | EIF5A | eukaryotic translation initiation factor 5A | Cytoplasm | translation regulator |
| 162 EIF5A2 | EIF5A2 | eukaryotic translation initiation factor 5A2 | Cytoplasm | translation regulator |
| 163 TCEB2 | ELOB | elongin B | Nucleus | transcription regulator |
| 164 ELOF1 | ELOF1 | elongation factor 1 homolog | Nucleus | other |
| 165 ENO1 | ENO1 | enolase 1 | Cytoplasm | enzyme |
| 166 EPN1 | EPN1 | epsin 1 | Plasma Membr. | transporter |
| 167 EQTN | EQTN | equatorin | Cytoplasm | other |
| 168 ESPN | ESPN | espin | Cytoplasm | other |
| 169 DGCR14 | ESS2 | ess-2 splicing factor homolog | Nucleus | other |
| 170 EVX1-AS | EVX1-AS | EVX1 antisense RNA | Other | other |
| 171 EVX2 | EVX2 | even-skipped homeobox 2 | Nucleus | transcription regulator |
| 172 FAM104A | FAM104A | family with sequence similarity 104 member A | Other | other |
| 173 FAM153A | FAM153A/B | family with sequence similarity 153 member B | Other | other |
| 174 FAM170B-AS1 | FAM170B-AS1 | FAM170B antisense RNA 1 | Other | other |
| 175 FAM186A | FAM186A | family with sequence similarity 186 member A | Other | other |
| 176 FAM209A | FAM209A | family with sequence similarity 209 member A | Other | other |
| 177 FAM212B | FAM212B | family with sequence similarity 212 member B | Nucleus | other |
| 178 FAM217A | FAM217A | family with sequence similarity 217 member A | Extrcellr Spce | other |
| 179 FAM220A | FAM220A | family with sequence similarity 220 member A | Nucleus | other |
| 180 FAM229A | FAM229A | family with sequence similarity 229 member A | Other | other |
| 181 FAM229B | FAM229B | family with sequence similarity 229 member B | Other | other |
| 182 FAM234A | FAM234A | family with sequence similarity 234 member A | Plasma Membr. | other |
| 183 FAM71F1 | FAM71F1 | family with sequence similarity 71 member F1 | Other | other |
| 184 FAM76B | FAM76B | family with sequence similarity 76 member B | Nucleus | other |
| 185 FAM81B | FAM81B | family with sequence similarity 81 member B | Nucleus | other |
| 186 FAM83C | FAM83C | family with sequence similarity 83 member C | Other | other |
| 187 FANK1 | FANK1 | fibronectin type III and ankyrin repeat domains 1 | Nucleus | transcription regulator |
| 188 FARP2 | FARP2 | FERM, ARH/RhoGEF and pleckstrin domain protein 2 | Cytoplasm | other |
| 189 FBXL13 | FBXL13 | F-box and leucine rich repeat protein 13 | Cytoplasm | enzyme |
| 190 FBXO34 | FBXO34 | F-box protein 34 | Other | other |
| 191 FBXW5 | FBXW5 | F-box and WD repeat domain containing 5 | Cytoplasm | enzyme |
| 192 FILIP1L | FILIP1L | filamin A interacting protein 1 like | Nucleus | other |
| 193 FKBP3 | FKBP3 | FK506 binding protein 3 | Nucleus | enzyme |
| 194 FKBP7 | FKBP7 | FK506 binding protein 7 | Cytoplasm | enzyme |
| 195 FKBP8 | FKBP8 | FK506 binding protein 8 | Cytoplasm | other |
| 196 FNDC8 | FNDC8 | fibronectin type III domain containing 8 | Nucleus | other |
| 197 FSCB | FSCB | fibrous sheath CABYR binding protein | Other | other |
| 198 FTH1 | FTH1 | ferritin heavy chain 1 | Cytoplasm | enzyme |
| 199 FUNDC2 | FUNDC2 | FUN14 domain containing 2 | Cytoplasm | other |
| 200 FXR1 | FXR1 | FMR1 autosomal homolog 1 | Cytoplasm | other |
| 201 GABARAPL1 | GABARAPL1 | GABA type A receptor associated protein like 1 | Cytoplasm | other |
| 202 GABRG3-AS1 | GABRG3-AS1 | GABRG3 antisense RNA 1 | Other | other |
| 203 GAPDH | GAPDH | glyceraldehyde-3-phosphate dehydrogenase | Cytoplasm | enzyme |
| 204 GDPD5 | GDPD5 | glycerophosphodiester phosphodiesterase domain containing 5 | Plasma Membr. | enzyme |
| 205 GGN | GGN | gametogenetin | Nucleus | other |
| 206 GINM1 | GINM1 | glycoprotein integral membrane 1 | Cytoplasm | other |
| 207 GKAP1 | GKAP1 | G kinase anchoring protein 1 | Cytoplasm | other |
| 208 GLRX2 | GLRX2 | glutaredoxin 2 | Cytoplasm | enzyme |
| 209 GLUL | GLUL | glutamate-ammonia ligase | Cytoplasm | enzyme |
| 210 GMFG | GMFG | glia maturation factor gamma | Cytoplasm | growth factor |
| 211 GNAI2 | GNAI2 | G protein subunit alpha i2 | Plasma Membr. | enzyme |
| 212 GNAS | GNAS | GNAS complex locus | Plasma Membr. | enzyme |
| 213 GOLGA6L10 | GOLGA6L9 | golgin A6 family-like 9 | Other | other |
| 214 GPR137 | GPR137 | G protein-coupled receptor 137 | Other | other |
| 215 GSG1 | GSG1 | germ cell associated 1 | Cytoplasm | other |
| 216 GSTO1 | GSTO1 | glutathione S-transferase omega 1 | Cytoplasm | enzyme |
| 217 GTSF1 | GTSF1 | gametocyte specific factor 1 | Cytoplasm | other |
| 218 GTSF1L | GTSF1L | gametocyte specific factor 1 like | Other | other |
| 219 H3F3B | H3F3A/H3F3B | H3 histone family member 3A | Nucleus | other |
| 220 HAGLR | HAGLR | HOXD antisense growth-associated long non-coding RNA | Other | other |
| 221 HBP1 | HBP1 | HMG-box transcription factor 1 | Nucleus | transcription regulator |
| 222 HDAC11 | HDAC11 | histone deacetylase 11 | Nucleus | transcription regulator |
| 223 HDAC4 | HDAC4 | histone deacetylase 4 | Nucleus | transcription regulator |
| 224 HDLBP | HDLBP | high density lipoprotein binding protein | Nucleus | transporter |
| 225 HMGB4 | HMGB4 | high mobility group box 4 | Nucleus | other |
| 226 HNRNPH1 | HNRNPH1 | heterogeneous nuclear ribonucleoprotein H1 | Nucleus | other |
| 227 HNRNPR | HNRNPR | heterogeneous nuclear ribonucleoprotein R | Nucleus | other |
| 228 HPCA | HPCA | hippocalcin | Cytoplasm | other |
| 229 HSPA4L | HSPA4L | heat shock protein family A (Hsp70) member 4 like | Cytoplasm | other |
| 230 HSPB6 | HSPB6 | heat shock protein family B (small) member 6 | Cytoplasm | other |
| 231 HSPH1 | HSPH1 | heat shock protein family H (Hsp110) member 1 | Cytoplasm | other |

TABLE 5-continued

Genes used in the Gene Signature set part 1

| ID | Symbol | Entrez Gene Name | Location | Type(s) |
|---|---|---|---|---|
| 232 | HYAL1 | HYAL1 | hyaluronoglucosaminidase 1 | Cytoplasm | enzyme |
| 233 | IBA57-AS1 | IBA57-AS1 | IBA57 antisense RNA 1 (head to head) | Other | other |
| 234 | ICA1 | ICA1 | islet cell autoantigen 1 | Cytoplasm | other |
| 235 | IGSF11-AS1 | IGSF11-AS1 | IGSF11 antisense RNA 1 | Other | other |
| 236 | IL13 | IL13 | interleukin 13 | Extrcellr Spce | cytokine |
| 237 | IL6R | IL6R | interleukin 6 receptor | Plasma Membr. | transmembrane receptor |
| 238 | INCA1 | INCA1 | inhibitor of CDK, cyclin A1 interacting protein 1 | Nucleus | other |
| 239 | INPP5B | INPP5B | inositol polyphosphate-5-phosphatase B | Plasma Membr. | phosphatase |
| 240 | INPP5K | INPP5K | inositol polyphosphate-5-phosphatase K | Cytoplasm | phosphatase |
| 241 | IPO5 | IPO5 | importin 5 | Nucleus | transporter |
| 242 | IQCF3 | IQCF3 | IQ motif containing F3 | Other | other |
| 243 | ISG20L2 | ISG20L2 | interferon stimulated exonuclease gene 20 like 2 | Nucleus | enzyme |
| 244 | ITCH | ITCH | itchy E3 ubiquitin protein ligase | Nucleus | enzyme |
| 245 | ITPKA | ITPKA | inositol-trisphosphate 3-kinase A | Cytoplasm | kinase |
| 246 | IZUMO4 | IZUMO4 | IZUMO family member 4 | Nucleus | other |
| 247 | JARID2-AS1 | JARID2-AS1 | JARID2 antisense RNA 1 | Other | other |
| 248 | KATNBL1 | KATNBL1 | katanin regulatory subunit B1 like 1 | Nucleus | other |
| 249 | KDM2B | KDM2B | lysine demethylase 2B | Nucleus | enzyme |
| 250 | KDM5B | KDM5B | lysine demethylase 5B | Nucleus | transcription regulator |
| 251 | KIAA1217 | KIAA1217 | KIAA1217 | Cytoplasm | other |
| 252 | KLHDC3 | KLHDC3 | kelch domain containing 3 | Cytoplasm | other |
| 253 | KLHL12 | KLHL12 | kelch like family member 12 | Cytoplasm | other |
| 254 | KMO | KMO | kynurenine 3-monooxygenase | Cytoplasm | enzyme |
| 255 | KRT15 | KRT15 | keratin 15 | Cytoplasm | other |
| 256 | KRTCAP3 | KRTCAP3 | keratinocyte associated protein 3 | Other | other |
| 257 | KRTDAP | KRTDAP | keratinocyte differentiation associated protein | Extrcellr Spce | other |
| 258 | KTN1 | KTN1 | kinectin 1 | Plasma Membr. | transmembrane receptor |
| 259 | LAPTM4A | LAPTM4A | lysosomal protein transmembrane 4 alpha | Cytoplasm | other |
| 260 | LCA5L | LCA5L | LCA5L, lebercilin like | Extrcellr Spce | other |
| 261 | LDLRAD4 | LDLRAD4 | low density lipoprotein receptor class A domain containing 4 | Cytoplasm | other |
| 262 | LELP1 | LELP1 | late cornified envelope like proline rich 1 | Other | other |
| 263 | LHX2 | LHX2 | LIM homeobox 2 | Nucleus | transcription regulator |
| 264 | LINC00442 | LINC00442 | long intergenic non-protein coding RNA 442 | Other | other |
| 265 | LINC00901 | LINC00901 | long intergenic non-protein coding RNA 901 | Other | other |
| 266 | LINC00906 | LINC00906 | long intergenic non-protein coding RNA 906 | Other | other |
| 267 | LINC00919 | LINC00919 | long intergenic non-protein coding RNA 919 | Other | other |
| 268 | LINC00943 | LINC00943 | long intergenic non-protein coding RNA 943 | Other | other |
| 269 | LINC01095 | LINC01095 | long intergenic non-protein coding RNA 1095 | Other | other |
| 270 | LINC01198 | LINC01198 | long intergenic non-protein coding RNA 1198 | Other | other |
| 271 | LINC01487 | LINC01487 | long intergenic non-protein coding RNA 1487 | Other | other |
| 272 | LMNTD2 | LMNTD2 | lamin tail domain containing 2 | Other | other |
| 273 | LMX1A | LMX1A | LIM homeobox transcription factor 1 alpha | Nucleus | transcription regulator |
| 274 | LPIN1 | LPIN1 | lipin 1 | Nucleus | phosphatase |
| 275 | LRRC52 | LRRC52 | leucine rich repeat containing 52 | Plasma Membr. | ion channel |
| 276 | LRRD1 | LRRD1 | leucine rich repeats and death domain containing 1 | Other | other |
| 277 | LRTOMT | LRTOMT | leucine rich transmembrane and O-methyltransferase domain | Plasma Membr. | enzyme |
| 278 | LYSMD2 | LYSMD2 | LysM domain containing 2 | Other | other |
| 279 | MAATS1 | MAATS1 | MYCBP associated and testis expressed 1 | Cytoplasm | other |
| 280 | MAD2L2 | MAD2L2 | mitotic arrest deficient 2 like 2 | Nucleus | enzyme |
| 281 | MALSU1 | MALSU1 | mitochondrial assembly of ribosomal large subunit 1 | Extrcellr Spce | other |
| 282 | MAMDC2-AS1 | MAMDC2-AS1 | MAMDC2 antisense RNA 1 | Other | other |
| 283 | MAP2K2 | MAP2K2 | mitogen-activated protein kinase kinase 2 | Cytoplasm | kinase |
| 284 | MAP3K14-AS1 | MAP3K14-AS1 | MAP3K14 antisense RNA 1 | Other | other |
| 285 | MAPK3 | MAPK3 | mitogen-activated protein kinase 3 | Cytoplasm | kinase |
| 286 | MAPKAPK5-AS1 | MAPKAPK5-AS1 | MAPKAPK5 antisense RNA 1 | Other | other |
| 287 | MAPT-AS1 | MAPT-AS1 | MAPT antisense RNA 1 | Other | other |
| 288 | MARCKS | MARCKS | myristoylated alanine rich protein kinase C substrate | Plasma Membr. | other |
| 289 | MED30 | MED30 | mediator complex subunit 30 | Nucleus | transcription regulator |
| 290 | MEIOC | MEIOC | meiosis specific with coiled-coil domain | Cytoplasm | other |
| 291 | MEIS1 | MEIS1 | Meis homeobox 1 | Nucleus | transcription regulator |
| 292 | MEST | MEST | mesoderm specific transcript | Cytoplasm | peptidase |
| 293 | METAP1 | METAP1 | methionyl aminopeptidase 1 | Cytoplasm | peptidase |
| 294 | MFAP3L | MFAP3L | microfibril associated protein 3 like | Other | other |
| 295 | MFF | MFF | mitochondrial fission factor | Cytoplasm | other |
| 296 | MGAT4C | MGAT4C | MGAT4 family member C | Cytoplasm | enzyme |
| 297 | MGST3 | MGST3 | microsomal glutathione S-transferase 3 | Cytoplasm | enzyme |
| 298 | MINOS1 | MINOS1 | mitochondrial inner membrane organizing system 1 | Cytoplasm | other |
| 299 | MIR7515HG | MIR7515HG | MIR7515 host gene | Other | other |
| 300 | MIR762HG | MIR762HG | MIR762 host gene | Other | other |
| 301 | MIS12 | MIS12 | MIS12, kinetochore complex component | Nucleus | other |
| 302 | MLF1 | MLF1 | myeloid leukemia factor 1 | Nucleus | other |
| 303 | MOSPD3 | MOSPD3 | motile sperm domain containing 3 | Other | other |
| 304 | MPC2 | MPC2 | mitochondrial pyruvate carrier 2 | Plasma Membr. | other |
| 305 | MRC2 | MRC2 | mannose receptor C type 2 | Plasma Membr. | transmembrane receptor |

TABLE 5-continued

Genes used in the Gene Signature set part 1

| ID | Symbol | Entrez Gene Name | Location | Type(s) |
|---|---|---|---|---|
| 306 MRFAP1 | MRFAP1 | Morf4 family associated protein 1 | Nucleus | other |
| 307 MROH7 | MROH7 | maestro heat like repeat family member 7 | Extrcellr Spce | other |
| 308 MRPL9 | MRPL9 | mitochondrial ribosomal protein L9 | Cytoplasm | translation regulator |
| 309 MRPS7 | MRPS7 | mitochondrial ribosomal protein S7 | Cytoplasm | other |
| 310 MS4A14 | MS4A14 | membrane spanning 4-domains A14 | Other | other |
| 311 MT-ATP6 | MT-ATP6 | ATP synthase F0 subunit 6 | Cytoplasm | transporter |
| 312 MT-CO1 | MT-CO1 | cytochrome c oxidase subunit I | Cytoplasm | enzyme |
| 313 MT-CO2 | MT-CO2 | cytochrome c oxidase subunit II | Cytoplasm | enzyme |
| 314 MT-CO3 | MT-CO3 | cytochrome c oxidase III | Cytoplasm | enzyme |
| 315 MT-ND2 | MT-ND2 | MTND2 | Cytoplasm | enzyme |
| 316 MTFR1L | MTFR1L | mitochondrial fission regulator 1 like | Other | other |
| 317 MTPAP | MTPAP | mitochondrial poly(A) polymerase | Cytoplasm | enzyme |
| 318 MYH7B | MYH7B | myosin heavy chain 7B | Other | other |
| 319 MYL6B | MYL6B | myosin light chain 6B | Cytoplasm | other |
| 320 NAT6 | NAT6 | N-acetyltransferase 6 | Cytoplasm | other |
| 321 NBR1 | NBR1 | NBR1, autophagy cargo receptor | Cytoplasm | other |
| 322 NDUFA11 | NDUFA11 | NADH:ubiquinone oxidoreductase subunit A11 | Cytoplasm | enzyme |
| 323 NDUFA13 | NDUFA13 | NADH:ubiquinone oxidoreductase subunit A13 | Cytoplasm | enzyme |
| 324 NDUFB6 | NDUFB6 | NADH:ubiquinone oxidoreductase subunit B6 | Cytoplasm | enzyme |
| 325 NDUFS8 | NDUFS8 | NADH:ubiquinone oxidoreductase core subunit S8 | Cytoplasm | enzyme |
| 326 NECAP2 | NECAP2 | NECAP endocytosis associated 2 | Cytoplasm | other |
| 327 PVRL3 | NECTIN3 | nectin cell adhesion molecule 3 | Plasma Membr. | other |
| 328 NFIB | NFIB | nuclear factor I B | Nucleus | transcription regulator |
| 329 NNAT | NNAT | neuronatin | Plasma Membr. | transporter |
| 330 NOLC1 | NOLC1 | nucleolar and coiled-body phosphoprotein 1 | Nucleus | transcription regulator |
| 331 NRAV | NRAV | negative regulator of antiviral response (non-protein coding) | Other | other |
| 332 NRBP1 | NRBP1 | nuclear receptor binding protein 1 | Nucleus | kinase |
| 333 NRDE2 | NRDE2 | NRDE-2, necessary for RNA interference, domain containing | Other | other |
| 334 NSUN4 | NSUN4 | NOP2/Sun RNA methyltransferase family member 4 | Cytoplasm | enzyme |
| 335 NT5C1B | NT5C1B | 5'-nucleotidase, cytosolic IB | Cytoplasm | phosphatase |
| 336 NUMBL | NUMBL | NUMB like, endocytic adaptor protein | Cytoplasm | other |
| 337 NUPR2 | NUPR2 | nuclear protein 2, transcriptional regulator | Nucleus | other |
| 338 OAZ3 | OAZ3 | ornithine decarboxylase antizyme 3 | Cytoplasm | transporter |
| 339 ODC1 | ODC1 | ornithine decarboxylase 1 | Cytoplasm | enzyme |
| 340 OPLAH | OPLAH | 5-oxoprolinase, ATP-hydrolysing | Cytoplasm | enzyme |
| 341 OR2H1 | OR2H1 | olfactory receptor family 2 subfamily H member 1 | Plasma Membr. | G-protein coupled receptor |
| 342 OSBP2 | OSBP2 | oxysterol binding protein 2 | Cytoplasm | other |
| 343 OVOS2 | OVOS2 | ovostatin 2 | Extrcellr Spce | other |
| 344 P4HTM | P4HTM | prolyl 4-hydroxylase, transmembrane | Cytoplasm | enzyme |
| 345 PACS2 | PACS2 | phosphofurin acidic cluster sorting protein 2 | Cytoplasm | other |
| 346 PAFAH1B1 | PAFAH1B1 | platelet activating factor acetylhydrolase 1b regulatory subunit | Cytoplasm | enzyme |
| 347 PAOX | PAOX | polyamine oxidase | Cytoplasm | enzyme |
| 348 PARP6 | PARP6 | poly(ADP-ribose) polymerase family member 6 | Other | other |
| 349 PCBP4 | PCBP4 | poly(rC) binding protein 4 | Nucleus | other |
| 350 PCGF5 | PCGF5 | polycomb group ring finger 5 | Cytoplasm | other |
| 351 PCOLCE-AS1 | PCOLCE-AS1 | PCOLCE antisense RNA 1 | Other | other |
| 352 PCSK4 | PCSK4 | proprotein convertase subtilisin/kexin type 4 | Extrcellr Spce | peptidase |
| 353 PCYT2 | PCYT2 | phosphate cytidylyltransferase 2, ethanolamine | Cytoplasm | enzyme |
| 354 PDXDC1 | PDXDC1 | pyridoxal dependent decarboxylase domain containing 1 | Cytoplasm | other |
| 355 PDXK | PDXK | pyridoxal kinase | Cytoplasm | kinase |
| 356 PDZD8 | PDZD8 | PDZ domain containing 8 | Extrcellr Spce | other |
| 357 PELP1 | PELP1 | proline, glutamate and leucine rich protein 1 | Nucleus | other |
| 358 PEX10 | PEX10 | peroxisomal biogenesis factor 10 | Cytoplasm | other |
| 359 PFN3 | PFN3 | profilin 3 | Other | other |
| 360 PGK2 | PGK2 | phosphoglycerate kinase 2 | Cytoplasm | kinase |
| 361 PGP | PGP | phosphoglycolate phosphatase | Cytoplasm | enzyme |
| 362 PHACTR2-AS1 | PHACTR2-AS1 | PHACTR2 antisense RNA 1 | Other | other |
| 363 PHKB | PHKB | phosphorylase kinase regulatory subunit beta | Cytoplasm | kinase |
| 364 PHKG2 | PHKG2 | phosphorylase kinase catalytic subunit gamma 2 | Cytoplasm | kinase |
| 365 PIBF1 | PIBF1 | progesterone immunomodulatory binding factor 1 | Nucleus | other |
| 366 PIN1 | PIN1 | peptidylprolyl cis/trans isomerase, NIMA-interacting 1 | Nucleus | enzyme |
| 367 PKM | PKM | pyruvate kinase M1/2 | Cytoplasm | kinase |
| 368 PLBD2 | PLBD2 | phospholipase B domain containing 2 | Extrcellr Spce | other |
| 369 PLCE1-AS2 | PLCE1-AS2 | PLCE1 antisense RNA 2 | Other | other |
| 370 PODXL2 | PODXL2 | podocalyxin like 2 | Plasma Membr. | other |
| 371 POLB | POLB | DNA polymerase beta | Nucleus | enzyme |
| 372 POLD2 | POLD2 | DNA polymerase delta 2, accessory subunit | Nucleus | enzyme |
| 373 POLR1D | POLR1D | RNA polymerase I subunit D | Nucleus | enzyme |
| 374 PPDPF | PPDPF | pancreatic progenitor cell differentiation and proliferation factor | Other | other |
| 375 PPM1G | PPM1G | protein phosphatase, Mg2+/Mn2+ dependent 1G | Nucleus | phosphatase |
| 376 PPP1R12B | PPP1R12B | protein phosphatase 1 regulatory subunit 12B | Cytoplasm | phosphatase |

TABLE 5-continued

Genes used in the Gene Signature set part 1

| ID | Symbol | Entrez Gene Name | Location | Type(s) |
|---|---|---|---|---|
| 377 PPP1R3E | PPP1R3E | protein phosphatase 1 regulatory subunit 3E | Cytoplasm | other |
| 378 PPP2R1B | PPP2R1B | protein phosphatase 2 scaffold subunit Abeta | Plasma Membr. | phosphatase |
| 379 PPP2R2B | PPP2R2B | protein phosphatase 2 regulatory subunit Bbeta | Cytoplasm | phosphatase |
| 380 PPP2R5A | PPP2R5A | protein phosphatase 2 regulatory subunit B'alpha | Cytoplasm | phosphatase |
| 381 PRC1-AS1 | PRC1-AS1 | PRC1 antisense RNA 1 | Other | other |
| 382 PRKCZ | PRKCZ | protein kinase C zeta | Cytoplasm | kinase |
| 383 PRM1 | PRM1 | protamine 1 | Nucleus | other |
| 384 PRM2 | PRM2 | protamine 2 | Nucleus | other |
| 385 PRM3 | PRM3 | protamine 3 | Nucleus | other |
| 386 PROCA1 | PROCA1 | protein interacting with cyclin A1 | Cytoplasm | other |
| 387 PSMA4 | PSMA4 | proteasome subunit alpha 4 | Cytoplasm | peptidase |
| 388 PSMD3 | PSMD3 | proteasome 26S subunit, non-ATPase 3 | Cytoplasm | other |
| 389 PSMD6 | PSMD6 | proteasome 26S subunit, non-ATPase 6 | Cytoplasm | enzyme |
| 390 PSMF1 | PSMF1 | proteasome inhibitor subunit 1 | Cytoplasm | other |
| 391 PTDSS2 | PTDSS2 | phosphatidylserine synthase 2 | Cytoplasm | enzyme |
| 392 PTK7 | PTK7 | protein tyrosine kinase 7 (inactive) | Plasma Membr. | kinase |
| 393 PTOV1 | PTOV1 | prostate tumor overexpressed 1 | Nucleus | other |
| 394 PTP4A1 | PTP4A1 | protein tyrosine phosphatase type IVA, member 1 | Cytoplasm | phosphatase |
| 395 PTPRD | PTPRD | protein tyrosine phosphatase, receptor type D | Plasma Membr. | phosphatase |
| 396 PWRN1 | PWRN1 | Prader-Willi region non-protein coding RNA 1 | Other | other |
| 397 RAB11FIP5 | RAB11FIP5 | RAB11 family interacting protein 5 | Cytoplasm | other |
| 398 RAB1A | RAB1A | RAB1A, member RAS oncogene family | Cytoplasm | enzyme |
| 399 RAB35 | RAB35 | RAB35, member RAS oncogene family | Cytoplasm | enzyme |
| 400 RAB3IP | RAB3IP | RAB3A interacting protein | Cytoplasm | other |
| 401 RAD21 | RAD21 | RAD21 cohesin complex component | Nucleus | transcription regulator |
| 402 RAD23B | RAD23B | RAD23 homolog B, nucleotide excision repair protein | Nucleus | other |
| 403 RANBP2 | RANBP2 | RAN binding protein 2 | Nucleus | enzyme |
| 404 RANGAP1 | RANGAP1 | Ran GTPase activating protein 1 | Nucleus | other |
| 405 RARA-AS1 | RARA-AS1 | RARA antisense RNA 1 | Other | other |
| 406 RBBP6 | RBBP6 | RB binding protein 6, ubiquitin ligase | Nucleus | enzyme |
| 407 RBCK1 | RBCK1 | RANBP2-type and C3HC4-type zinc finger containing 1 | Cytoplasm | transcription regulator |
| 408 RBM15B | RBM15B | RNA binding motif protein 15B | Nucleus | other |
| 409 RCOR3 | RCOR3 | REST corepressor 3 | Nucleus | other |
| 410 REEP6 | REEP6 | receptor accessory protein 6 | Plasma Membr. | other |
| 411 RFPL3S | RFPL3S | RFPL3 antisense | Other | other |
| 412 RGS22 | RGS22 | regulator of G protein signaling 22 | Cytoplasm | other |
| 413 RIOK3 | RIOK3 | RIO kinase 3 | Cytoplasm | kinase |
| 414 RMND5B | RMND5B | required for meiotic nuclear division 5 homolog B | Other | other |
| 415 RND2 | RND2 | Rho family GTPase 2 | Cytoplasm | enzyme |
| 416 RNF103 | RNF103 | ring finger protein 103 | Cytoplasm | enzyme |
| 417 RNF11 | RNF11 | ring finger protein 11 | Cytoplasm | enzyme |
| 418 RNF138 | RNF138 | ring finger protein 138 | Nucleus | enzyme |
| 419 RNF139 | RNF139 | ring finger protein 139 | Cytoplasm | enzyme |
| 420 RNF139-AS1 | RNF139-AS1 | RNF139 antisense RNA 1 (head to head) | Other | other |
| 421 RNF32 | RNF32 | ring finger protein 32 | Cytoplasm | other |
| 422 RNF38 | RNF38 | ring finger protein 38 | Nucleus | enzyme |
| 423 RNFT2 | RNFT2 | ring finger protein, transmembrane 2 | Other | other |
| 424 RPL10 | RPL10 | ribosomal protein L10 | Cytoplasm | translation regulator |
| 425 RPL12 | RPL12 | ribosomal protein L12 | Nucleus | other |
| 426 RPL13 | RPL13 | ribosomal protein L13 | Nucleus | other |
| 427 RPL13A | RPL13A | ribosomal protein L13a | Cytoplasm | other |
| 428 RPL15 | RPL15 | ribosomal protein L15 | Cytoplasm | other |
| 429 RPL19 | RPL19 | ribosomal protein L19 | Cytoplasm | other |
| 430 RPL23A | RPL23A | ribosomal protein L23a | Cytoplasm | other |
| 431 RPL29 | RPL29 | ribosomal protein L29 | Cytoplasm | other |
| 432 RPL3 | RPL3 | ribosomal protein L3 | Nucleus | other |
| 433 RPL36 | RPL36 | ribosomal protein L36 | Cytoplasm | other |
| 434 RPL37 | RPL37 | ribosomal protein L37 | Cytoplasm | other |
| 435 RPL37A | RPL37A | ribosomal protein L37a | Cytoplasm | other |
| 436 RPL41 | RPL41 | ribosomal protein L41 | Cytoplasm | other |
| 437 RPL8 | RPL8 | ribosomal protein L8 | Cytoplasm | other |
| 438 RPLP1 | RPLP1 | ribosomal protein lateral stalk subunit P1 | Cytoplasm | other |
| 439 RPS15 | RPS15 | ribosomal protein S15 | Cytoplasm | other |
| 440 RPS18 | RPS18 | ribosomal protein S18 | Cytoplasm | other |
| 441 RPS27A | RPS27A | ribosomal protein S27a | Cytoplasm | other |
| 442 RPS4X | RPS4X | ribosomal protein S4, X-linked | Cytoplasm | other |
| 443 RPS6 | RPS6 | ribosomal protein S6 | Cytoplasm | other |
| 444 RPS8 | RPS8 | ribosomal protein S8 | Cytoplasm | other |
| 445 RPS9 | RPS9 | ribosomal protein S9 | Cytoplasm | translation regulator |
| 446 RSRC2 | RSRC2 | arginine and serine rich coiled-coil 2 | Other | other |
| 447 RTN4 | RTN4 | reticulon 4 | Cytoplasm | other |
| 448 RUVBL2 | RUVBL2 | RuvB like AAA ATPase 2 | Nucleus | transcription regulator |
| 449 S100A7A | S100A7A | S100 calcium binding protein A7A | Cytoplasm | other |

TABLE 5-continued

Genes used in the Gene Signature set part 1

| ID | Symbol | Entrez Gene Name | Location | Type(s) |
|---|---|---|---|---|
| 450 SAMD4A | SAMD4A | sterile alpha motif domain containing 4A | Cytoplasm | translation regulator |
| 451 SARAF | SARAF | store-operated calcium entry associated regulatory factor | Cytoplasm | other |
| 452 SCRT1 | SCRT1 | scratch family transcriptional repressor 1 | Nucleus | transcription regulator |
| 453 SEC14L1 | SEC14L1 | SEC14 like lipid binding 1 | Cytoplasm | transporter |
| 454 SEMG1 | SEMG1 | semenogelin I | Extrcellr Spce | other |
| 455 SERF2 | SERF2 | small EDRK-rich factor 2 | Other | other |
| 456 SERPINB6 | SERPINB6 | serpin family B member 6 | Cytoplasm | other |
| 457 SETD9 | SETD9 | SET domain containing 9 | Nucleus | enzyme |
| 458 SH3GL3 | SH3GL3 | SH3 domain containing GRB2 like 3, endophilin A3 | Cytoplasm | other |
| 459 SHARPIN | SHARPIN | SHANK associated RH domain interactor | Plasma Membr. | other |
| 460 SIPA1L1 | SIPA1L1 | signal induced proliferation associated 1 like 1 | Cytoplasm | other |
| 461 SKP1 | SKP1 | S-phase kinase associated protein 1 | Nucleus | transcription regulator |
| 462 SLAIN2 | SLAIN2 | SLAIN motif family member 2 | Cytoplasm | other |
| 463 SLC25A39 | SLC25A39 | solute carrier family 25 member 39 | Cytoplasm | other |
| 464 SLC2A8 | SLC2A8 | solute carrier family 2 member 8 | Plasma Membr. | transporter |
| 465 SLC37A1 | SLC37A1 | solute carrier family 37 member 1 | Plasma Membr. | transporter |
| 466 SLC38A7 | SLC38A7 | solute carrier family 38 member 7 | Plasma Membr. | transporter |
| 467 SLC5A2 | SLC5A2 | solute carrier family 5 member 2 | Plasma Membr. | transporter |
| 468 SLFNL1 | SLFNL1 | schlafen like 1 | Other | other |
| 469 SMCP | SMCP | sperm mitochondria associated cysteine rich protein | Cytoplasm | other |
| 470 SMIM6 | SMIM6 | small integral membrane protein 6 | Other | other |
| 471 SMKR1 | SMKR1 | small lysine rich protein 1 | Other | other |
| 472 SMPD2 | SMPD2 | sphingomyelin phosphodiesterase 2 | Cytoplasm | enzyme |
| 473 SNHG9 | SNHG9 | small nucleolar RNA host gene 9 | Other | other |
| 474 SNX13 | SNX13 | sorting nexin 13 | Cytoplasm | transporter |
| 475 SORBS3 | SORBS3 | sorbin and SH3 domain containing 3 | Cytoplasm | other |
| 476 SORCS3-AS1 | SORCS3-AS1 | SORCS3 antisense RNA 1 | Other | other |
| 477 SPATA18 | SPATA18 | spermatogenesis associated 18 | Cytoplasm | other |
| 478 SPATA3 | SPATA3 | spermatogenesis associated 3 | Other | other |
| 479 SPATC1L | SPATC1L | spermatogenesis and centriole associated 1 like | Other | other |
| 480 SPCS1 | SPCS1 | signal peptidase complex subunit 1 | Cytoplasm | peptidase |
| 481 SPIRE1 | SPIRE1 | spire type actin nucleation factor 1 | Cytoplasm | other |
| 482 SPPL2B | SPPL2B | signal peptide peptidase like 2B | Plasma Membr. | peptidase |
| 483 SPTBN2 | SPTBN2 | spectrin beta, non-erythrocytic 2 | Cytoplasm | other |
| 484 SPTY2D1-AS1 | SPTY2D1OS | SPTY2D1 opposite strand | Other | other |
| 485 SPZ1 | SPZ1 | spermatogenic leucine zipper 1 | Nucleus | transcription regulator |
| 486 SRP54 | SRP54 | signal recognition particle 54 | Cytoplasm | other |
| 487 SRPK2 | SRPK2 | SRSF protein kinase 2 | Nucleus | kinase |
| 488 SSUH2 | SSUH2 | ssu-2 homolog (C. elegans) | Cytoplasm | other |
| 489 ST13 | ST13 | ST13, Hsp70 interacting protein | Cytoplasm | other |
| 490 STARD10 | STARD10 | StAR related lipid transfer domain containing 10 | Cytoplasm | other |
| 491 STK32C | STK32C | serine/threonine kinase 32C | Other | kinase |
| 492 STK35 | STK35 | serine/threonine kinase 35 | Cytoplasm | kinase |
| 493 C7orf73 | STMP1 | short transmembrane mitochondrial protein 1 | Other | other |
| 494 STOML2 | STOML2 | stomatin like 2 | Plasma Membr. | other |
| 495 C9orf173 | STPG3 | sperm-tail PG-rich repeat containing 3 | Other | other |
| 496 STT3B | STT3B | STT3B, catalytic subunit of the oligosaccharyltransferase complex | Cytoplasm | enzyme |
| 497 SYNCRIP | SYNCRIP | synaptotagmin binding cytoplasmic RNA interacting protein | Nucleus | other |
| 498 SYS1 | SYS1 | SYS1, golgi trafficking protein | Cytoplasm | other |
| 499 TADA2A | TADA2A | transcriptional adaptor 2A | Nucleus | transcription regulator |
| 500 TAF10 | TAF10 | TATA-box binding protein associated factor 10 | Nucleus | transcription regulator |
| 501 TAF5L | TAF5L | TATA-box binding protein associated factor 5 like | Nucleus | transcription regulator |
| 502 TBC1D10B | TBC1D10B | TBC1 domain family member 10B | Plasma Membr. | enzyme |
| 503 TCP1 | TCP1 | t-complex 1 | Cytoplasm | other |
| 504 TCP11 | TCP11 | t-complex 11 | Cytoplasm | other |
| 505 TEPP | TEPP | testis, prostate and placenta expressed | Other | other |
| 506 TEX38 | TEX38 | testis expressed 38 | Other | other |
| 507 C2orf57 | TEX44 | testis expressed 44 | Cytoplasm | other |
| 508 TIGAR | TIGAR | TP53 induced glycolysis regulatory phosphatase | Cytoplasm | enzyme |
| 509 TLE4 | TLE4 | transducin like enhancer of split 4 | Nucleus | transcription regulator |
| 510 TMBIM6 | TMBIM6 | transmembrane BAX inhibitor motif containing 6 | Nucleus | other |
| 511 TMCO2 | TMCO2 | transmembrane and coiled-coil domains 2 | Nucleus | other |
| 512 TMEM120A | TMEM120A | transmembrane protein 120A | Other | other |
| 513 TMEM160 | TMEM160 | transmembrane protein 160 | Cytoplasm | other |
| 514 TMEM191C | TMEM191B/C | transmembrane protein 191C | Other | other |
| 515 TMEM215 | TMEM215 | transmembrane protein 215 | Other | other |
| 516 TMEM260 | TMEM260 | transmembrane protein 260 | Other | other |
| 517 TMEM38B | TMEM38B | transmembrane protein 38B | Nucleus | ion channel |
| 518 TMSB4X | TMSB10/TMSB4X | thymosin beta 4, X-linked | Cytoplasm | other |
| 519 TNFAIP8L1 | TNFAIP8L1 | TNF alpha induced protein 8 like 1 | Cytoplasm | other |
| 520 TNKS | TNKS | tankyrase | Nucleus | enzyme |
| 521 TNP1 | TNP1 | transition protein 1 | Nucleus | other |
| 522 FAM179A | TOGARAM2 | TOG array regulator of axonemal microtubules 2 | Other | other |

TABLE 5-continued

Genes used in the Gene Signature set part 1

| ID | Symbol | Entrez Gene Name | Location | Type(s) |
|---|---|---|---|---|
| 523 TOLLIP | TOLLIP | toll interacting protein | Cytoplasm | other |
| 524 TP53I11 | TP53I11 | tumor protein p53 inducible protein 11 | Other | other |
| 525 TP53TG5 | TP53TG5 | TP53 target 5 | Nucleus | other |
| 526 TPCN1 | TPCN1 | two pore segment channel 1 | Plasma Membr. | ion channel |
| 527 TPD52L3 | TPD52L3 | tumor protein D52 like 3 | Other | other |
| 528 TPGS2 | TPGS2 | tubulin polyglutamylase complex subunit 2 | Nucleus | other |
| 529 TPI1 | TPI1 | triosephosphate isomerase 1 | Cytoplasm | enzyme |
| 530 TPP2 | TPP2 | tripeptidyl peptidase 2 | Cytoplasm | peptidase |
| 531 TPPP2 | TPPP2 | tubulin polymerization promoting protein family member 2 | Nucleus | other |
| 532 TPT1 | TPT1 | tumor protein, translationally-controlled 1 | Cytoplasm | other |
| 533 TRABD | TRABD | TraB domain containing | Extrcellr Spce | other |
| 534 TRIM11 | TRIM11 | tripartite motif containing 11 | Cytoplasm | enzyme |
| 535 TRMT5 | TRMT5 | tRNA methyltransferase 5 | Cytoplasm | other |
| 536 TSPAN1 | TSPAN1 | tetraspanin 1 | Cytoplasm | other |
| 537 TSPAN16 | TSPAN16 | tetraspanin 16 | Other | other |
| 538 TSPAN6 | TSPAN6 | tetraspanin 6 | Plasma Membr. | other |
| 539 TSSK1B | TSSK1B | testis specific serine kinase 1B | Cytoplasm | kinase |
| 540 TSSK2 | TSSK2 | testis specific serine kinase 2 | Cytoplasm | kinase |
| 541 TSSK6 | TSSK6 | testis specific serine kinase 6 | Nucleus | kinase |
| 542 TTC7A | TTC7A | tetratricopeptide repeat domain 7A | Plasma Membr. | other |
| 543 TTLL1 | TTLL1 | tubulin tyrosine ligase like 1 | Extrcellr Spce | enzyme |
| 544 TTLL10 | TTLL10 | tubulin tyrosine ligase like 10 | Cytoplasm | enzyme |
| 545 TUBB4B | TUBB4B | tubulin beta 4B class IVb | Cytoplasm | other |
| 546 TUBGCP4 | TUBGCP4 | tubulin gamma complex associated protein 4 | Cytoplasm | other |
| 547 TXNDC2 | TXNDC2 | thioredoxin domain containing 2 | Cytoplasm | enzyme |
| 548 UBA5 | UBA5 | ubiquitin like modifier activating enzyme 5 | Cytoplasm | enzyme |
| 549 UBA52 | UBA52 | ubiquitin A-52 residue ribosomal protein fusion product 1 | Cytoplasm | enzyme |
| 550 UBAC1 | UBAC1 | UBA domain containing 1 | Nucleus | other |
| 551 UBE2D2 | UBE2D2 | ubiquitin conjugating enzyme E2 D2 | Cytoplasm | enzyme |
| 552 UBE2N | UBE2N | ubiquitin conjugating enzyme E2 N | Cytoplasm | enzyme |
| 553 UBE4A | UBE4A | ubiquitination factor E4A | Cytoplasm | enzyme |
| 554 UBQLN3 | UBQLN3 | ubiquilin 3 | Cytoplasm | other |
| 555 UBXN6 | UBXN6 | UBX domain protein 6 | Cytoplasm | other |
| 556 UGT1A6 | UGT1A6 | UDP glucuronosyltransferase family 1 member A6 | Cytoplasm | enzyme |
| 557 UNC119B | UNC119B | unc-119 lipid binding chaperone B | Cytoplasm | other |
| 558 UQCRB | UQCRB | ubiquinol-cytochrome c reductase binding protein | Cytoplasm | enzyme |
| 559 USP2 | USP2 | ubiquitin specific peptidase 2 | Cytoplasm | peptidase |
| 560 USP25 | USP25 | ubiquitin specific peptidase 25 | Cytoplasm | peptidase |
| 561 USPL1 | USPL1 | ubiquitin specific peptidase like 1 | Cytoplasm | peptidase |
| 562 VGLL3 | VGLL3 | vestigial like family member 3 | Other | other |
| 563 VN1R2 | VN1R2 | vomeronasal 1 receptor 2 | Plasma Membr. | G-protein coupled receptor |
| 564 VRK3 | VRK3 | vaccinia related kinase 3 | Nucleus | kinase |
| 565 VTI1B | VTI1B | vesicle transport through interaction with t-SNAREs 1B | Plasma Membr. | transporter |
| 566 VWA3B | VWA3B | von Willebrand factor A domain containing 3B | Other | other |
| 567 WASF1 | WASF1 | WAS protein family member 1 | Nucleus | other |
| 568 WBP2NL | WBP2NL | WBP2 N-terminal like | Cytoplasm | other |
| 569 WDR20 | WDR20 | WD repeat domain 20 | Nucleus | peptidase |
| 570 WDR55 | WDR55 | WD repeat domain 55 | Nucleus | other |
| 571 WDR74 | WDR74 | WD repeat domain 74 | Nucleus | other |
| 572 WI2-2373I1.2 | WI2-2373I1.2 | forkhead box L1-like | Other | other |
| 573 WTIP | WTIP | WT1 interacting protein | Nucleus | transcription regulator |
| 574 XPNPEP3 | XPNPEP3 | X-prolyl aminopeptidase 3 | Cytoplasm | peptidase |
| 575 YPEL5 | YPEL5 | yippee like 5 | Nucleus | other |
| 576 ZC3H15 | ZC3H15 | zinc finger CCCH-type containing 15 | Nucleus | other |
| 577 ZCCHC8 | ZCCHC8 | zinc finger CCHC-type containing 8 | Nucleus | other |
| 578 ZDHHC19 | ZDHHC19 | zinc finger DHHC-type containing 19 | Cytoplasm | other |
| 579 ZDHHC3 | ZDHHC3 | zinc finger DHHC-type containing 3 | Cytoplasm | peptidase |
| 580 ZEB1 | ZEB1 | zinc finger E-box binding homeobox 1 | Nucleus | transcription regulator |
| 581 ZFAND3 | ZFAND3 | zinc finger AN1-type containing 3 | Other | other |
| 582 ZFAND4 | ZFAND4 | zinc finger AN1-type containing 4 | Other | other |
| 583 ZFP36L1 | ZFP36L1 | ZFP36 ring finger protein like 1 | Nucleus | transcription regulator |
| 584 ZFYVE28 | ZFYVE28 | zinc finger FYVE-type containing 28 | Cytoplasm | other |
| 585 ZMIZ2 | ZMIZ2 | zinc finger MIZ-type containing 2 | Nucleus | transcription regulator |
| 586 ZMYM2 | ZMYM2 | zinc finger MYM-type containing 2 | Nucleus | kinase |
| 587 ZNF32-AS3 | ZNF32-AS3 | ZNF32 antisense RNA 3 | Other | other |
| 588 ZNF445 | ZNF445 | zinc finger protein 445 | Nucleus | transcription regulator |
| 589 ZNF571-AS1 | ZNF571-AS1 | ZNF571 antisense RNA 1 | Other | other |
| 590 ZNF688 | ZNF688 | zinc finger protein 688 | Other | other |
| 591 ZNF706 | ZNF706 | zinc finger protein 706 | Other | other |
| 592 ZNHIT2 | ZNHIT2 | zinc finger HIT-type containing 2 | Other | other |
| 593 ZNRD1 | ZNRD1 | zinc ribbon domain containing 1 | Nucleus | transcription regulator |

TABLE 6

Genes used in the Gene Signature set part 2

| Ensembl_ID | gene_name | gene_type |
|---|---|---|
| ENSG00000271933.1 | RP11-338I21.1 | antisense |
| ENSG00000261120.1 | RP11-62H20.1 | antisense |
| ENSG00000250303.2 | RP11-356J5.12 | processed_transcript |
| ENSG00000231496.1 | RP1-251M9.2 | lincRNA |
| ENSG00000236866.1 | AL157902.3 | antisense |
| ENSG00000248925.1 | CTD-2083E4.6 | antisense |
|  | RP11-567M16.6 |  |
| ENSG00000254254.1 | RP11-17A4.2 | antisense |
| ENSG00000267002.1 | RP11-242D8.1 | lincRNA |
| ENSG00000258866.1 | RP11-991C1.2 | lincRNA |
| ENSG00000236267.1 | AP006216.5 | antisense |
| ENSG00000246090.2 | RP11-696N14.1 | antisense |
| ENSG00000204929.7 | AC074391.1 | lincRNA |
|  | CTC-543D15.8 |  |
| ENSG00000273010.1 | RP11-96K19.5 | antisense |
| ENSG00000234222.2 | RP11-315I20.1 | antisense |
| ENSG00000232265.3 | XXyac-YX155B6.5 | lincRNA |
| ENSG00000272823.1 | RP11-295M18.6 | lincRNA |
| ENSG00000272562.1 | RP11-396C23.4 | antisense |
| ENSG00000223734.2 | RP11-644K8.1 | antisense |
| ENSG00000225205.1 | AC093818.1 | antisense |
| ENSG00000237166.1 | AC007163.3 | lincRNA |
| ENSG00000261734.1 | RP11-669C19.1 | lincRNA |
| ENSG00000248686.1 | RP11-557J10.5 | lincRNA |
| ENSG00000270697.1 | RP11-381K20.4 | lincRNA |
| ENSG00000253811.1 | CTD-2363C16.1 | antisense |
| ENSG00000228412.2 | RP4-625H18.2 | lincRNA |
| ENSG00000235781.1 | XXbac-BPG249D20.9 | antisense |
| ENSG00000272288.1 | RP11-140K17.3 | antisense |
| ENSG00000240859.1 | AC093627.10 | lincRNA |
| ENSG00000228596.1 | AC013436.6 | antisense |
| ENSG00000272267.1 | RP11-375N15.2 | antisense |
| ENSG00000254092.1 | RP11-369E15.3 | lincRNA |
| ENSG00000272256.1 | RP11-489E7.4 | antisense |
| ENSG00000254815.1 | RP11-496I9.1 | antisense |
| ENSG00000254594.1 | RP11-2F20.1 | lincRNA |
| ENSG00000245552.2 | RP11-712B9.2 | antisense |
| ENSG00000255546.1 | RP11-168K9.1 | lincRNA |
| ENSG00000262732.1 | CTD-2135D7.2 | antisense |
| ENSG00000261266.1 | CTD-2196E14.5 | antisense |
| ENSG00000266677.1 | RP11-258F1.1 | antisense |
| ENSG00000267420.1 | RP11-527L4.6 | lincRNA |
| ENSG00000265204.1 | RP11-403A21.3 | antisense |
| ENSG00000267122.1 | AC004490.1 | antisense |
| ENSG00000186019.10 | AC084219.4 | antisense |
| ENSG00000229766.2 | RP5-971N18.3 | antisense |
| ENSG00000233277.1 | RP5-1030M6.3 | lincRNA |
| ENSG00000234967.1 | RP11-347D21.1 | lincRNA |
| ENSG00000268288.1 | RP11-98D18.16 | antisense |
| ENSG00000232113.1 | RP11-360D2.1 | antisense |
| ENSG00000260021.1 | RP11-480I12.10 | antisense |
| ENSG00000260698.1 | RP11-439E19.9 | lincRNA |
| ENSG00000227713.1 | AC116609.1 | lincRNA |
| ENSG00000271889.1 | RP11-493E12.1 | lincRNA |
| ENSG00000234255.4 | AC012370.3 | lincRNA |
| ENSG00000237576.1 | AC097495.2 | antisense |
| ENSG00000228363.2 | AC015971.2 | antisense |
| ENSG00000234169.1 | AC092168.3 | lincRNA |
| ENSG00000231898.4 | AC012594.1 | antisense |
| ENSG00000231597.1 | AC007557.4 | antisense |
| ENSG00000236295.1 | AC007563.1 | antisense |
| ENSG00000223874.1 | AC007557.1 | protein_coding |
| ENSG00000260526.1 | RP11-73K9.2 | antisense |
| ENSG00000249818.1 | RP11-73G16.3 | lincRNA |
| ENSG00000225230.1 | AC008937.3 | antisense |
| ENSG00000253787.1 | RP11-404L6.2 | protein_coding |
| ENSG00000232236.1 | RP1-266L20.2 | antisense |
| ENSG00000241449.1 | RP11-545G3.1 | lincRNA |
| ENSG00000246851.1 | RP11-544A12.8 | antisense |
| ENSG00000228636.1 | RP5-1051H14.2 | lincRNA |
| ENSG00000254823.1 | RP11-109E10.1 | lincRNA |
| ENSG00000257718.1 | RP11-396F22.1 | antisense |
| ENSG00000245904.2 | RP11-796E2.4 | antisense |
| ENSG00000219926.6 | RP11-394A14.2 | lincRNA |
| ENSG00000258742.1 | RP11-862G15.1 | lincRNA |
| ENSG00000259245.1 | RP11-684B21.1 | lincRNA |

TABLE 6-continued

Genes used in the Gene Signature set part 2

| Ensembl_ID | gene_name | gene_type |
|---|---|---|
| ENSG00000259878.1 | RP11-1O10.1 | lincRNA |
| ENSG00000264044.1 | RP11-192H23.7 | antisense |
| ENSG00000266013.1 | CTD-2206N4.2 | lincRNA |
| ENSG00000233483.2 | CTD-2020K17.4 | antisense |
| ENSG00000249383.1 | RP11-1018N14.1 | lincRNA |
| ENSG00000266290.1 | RP11-159D12.10 | lincRNA |
| ENSG00000267078.1 | RP11-666A8.9 | antisense |
| ENSG00000263823.1 | RP11-326K13.4 | antisense |
| ENSG00000265778.1 | RP11-17M16.2 | antisense |
| ENSG00000267308.1 | AC004510.3 | lincRNA |
| ENSG00000261341.1 | CTD-2568A17.1 | lincRNA |
|  | CTC-543D15.8 |  |
|  | RP11-173A6.3 |  |
|  | CTD-3035K23.7 |  |
|  | RP11-666O2.2 |  |
|  | AC007325.4 |  |
|  | RP11-2C24.7 |  |
|  | CCDC7.1 |  |
|  | AF131216.1 |  |
|  | RP11-14J7.7 |  |

What is claimed is:

1. A method comprising
isolating single sperm cells from a sperm sample;
constructing single cell RNA-Seq libraries, direct RNA measurement libraries, or cDNA libraries from the isolated single sperm cells;
generating a gene expression profile of each of MIR762HG, RP11-315I20.1, TADA2A, MEST, RP11-480I12.10, TMCO2, ZFP36L1, ATP1B3, CRAMP1, SPTY2D1-AS1, TNP1, AC007557.1, ACAP1, MARCKS, CTD-2568A17.1, PRM1, TCEB2, and TMEM31 based on the constructed single cell RNA-Seq libraries, direct RNA measurement libraries, or cDNA libraries;
comparing expression levels of the genes in the gene expression profile with reference expression levels of the same genes in a control healthy sperm sample;
determining that none of the genes in the expression profile are upregulated compared to the level of expression of the respective same gene in a healthy control sperm sample; and
utilizing the sperm sample for in vitro fertilization.

2. The method of claim 1, wherein single cell RNA-Seq libraries are constructed from the isolated single sperm cells, and wherein the method further comprises analyzing the sequences of the single-cell RNA-seq libraries for mutations.

3. The method of claim 2, wherein the mutations comprise Single Nucleotide Polymorphisms (SNPs), insertions, deletions, or copy-number variations.

4. The method of claim 1, wherein the sperm is a human sperm sample.

5. The method of claim 1, wherein the gene expression profile further comprises at least one additional gene selected from the group consisting of BACE1-AS, UNC119B, RP11-338I21.1, MEIS1, WDR55, IL6R, RP11-62H20.1, RP11-356J5.12, RP1-251M9.2, DNAJB4, MALSU1, EFCAB14, C3, RAB35, DNAJB7, DYNLL2, TIGAR, SSUH2, TPCN1, AL157902.3, STK32C, MED30, CTD-2083E4.6, LHX2, RP11-567M16.6, PHKB, CAHM, RP11-17A4.2, SIPA1L1, TMEM260, CDC42BPA, EVX1-AS, RP11-242D8.1, CDIPT, RP11-991C1.2, AP006216.5, RP11-696N14.1, TRABD, AC074391.1, CLCN3, RP11-644K8.1, GABARAPL1, ATF3, RFPL3S, CTD-2196E14.5, RP11-49619.1, RP11-347D21.1, TRMT5, RP11-712B9.2, CSTL1, XXbac-BPG249D20.9, RP11-669C19.1, NRDE2, MAPT-AS1, EFCAB12, VGLL3, DCC, HSPB6, S100A7A, CTD-2135D7.2, KRT15, RP11-403A21.3, RP11-396C23.4, C10orf90, GMFG, KDM2B, TMSB4X, RP11-381K20.4, OR2H1, ZNF445, TEPP, CTC-543D15.8, CCDC155, MAPK3, RP5-1030M6.3, SORCS3-AS1, RP11-489E7.4, AC007163.3, XXyac-YX155B6.5, TP53TG5, C9orf3, APOL6, ARL4C, AC093627.10, SERPINB6, PIBF1, CDK19, RBBP6, RP11-140K17.3, EAF1, GLRX2, RP11-557J10.5, DAG1, RP11-96K19.5, WDR20, AC093818.1, NECAP2, RP11-375N15.2, DHDDS, LRRC52, WTIP, TNKS, CFAP157, COX8C, XPNPEP3, NOLC1, RARA-AS1, RP4-625H18.2, FANK1, PPP2R1B, RP11-168K9.1, ARL6IP4, AACS, RSRC2, ZCCHC8, CTD-2363C16.1, KLHL12, CEP152, RP11-295M18.6, AC084219.4, HDAC4, DPP3, OVOS2, MAMDC2-AS1, FAM186A, ACSS1, CDIP1, INPP5B, PPP1R12B, RP11-527L4.6, ATP6VIA, EFCAB11, VN1R2, FAM179A, PELP1, STOML2, PCOLCE-AS1, AC004490.1, EVX2, RP11-258F1.1, CDKN1C, RP5-971N18.3, LAPTM4A, RP11-369E15.3, EIF5A2, PTPRD, RNF139-AS1, FAM71F1, CLK3, UGT1A6, C21orf91, DES, IBA57-AS1, HNRNPR, CCDC168, AC013436.6, ZNF32-AS3, LINC01095, MAPKAPK5-AS1, RP11-2F20.1, DGCR8, AC007563.1, UBE4A, AC004510.3, SYNCRIP, HSPH1, CTD-2206N4.2, LINC00919, RP11-17M16.2, ADGRG1, KRTCAP3, JARID2-AS1, CREB3L2, AC092168.3, RP11-493E12.1, SETD9, MRC2, AC008937.3, RP11-159D12.10, CCSER1, RP11-1018N14.1, FILIP1L, KIAA1217, RNFT2, NDUFA11, AC015971.2, CDH23, RP11-98D18.16, HNRNPH1, CTB-5506.13, P4HTM, SMIM6, TTLL1, UQCRB, AC097495.2, RP11-796E2.4, LYSMD2, MGAT4C, RP11-862G15.1, PFN3, FAM212B, RBM15B, RNF103, RP11-396F22.1, C10orf82, SYS1, RP11-404L6.2, DDX5, LINC00906, PSMD3, PPP1R3E, PTK7, LINC01487, MAP3K14-AS1, MRPL9, ZFYVE28, KRTDAP, OSBP2, NUMBL, FKBP7, LMX1A, TXNDC2, ZCCHC8, RP11-666A8.9, RP5-1051H14.2, NRBP1, FAM170B-AS1, RP11-439E19.9, RPL37, MGST3, CTD-2020K17.4, SCRT1, RP11-173A6.3, FBXO34, MRFAP1, TRIM11, PCBP4, RANBP2, FAM229A, EQTN, GOLGA6L10, AC116609.1, MTPAP, GSTO1, PACS2, CTD-3035K23.7, RP11-73K9.2, FAM153A, CCDC80, ACTL7B, CFL1, RP11-1010.1, GTSF1L, AC007557.4, SPIRE1, MRPS7, EAF1-AS1, RP11-545G3.1, IQCF3, CLIC5, SLC37A1, RP11-394A14.2, MYH7B, FKBP3, MINOS1, CENPJ, CFAP44, BRD2, RP11-684B21.1, AGAP1, FARP2, MIR7515HG, RP11-544A12.8, KMO, FAM209A, TMEM160, TAF5L, PSMA4, LINC01198, LDLRAD4, LINC00442, HYAL1, ATPAF1, C20orf144, ARF4-AS1, APOPT1, DNAAF3, EIF5A, NFIB, HPCA, CSPP1, IPO5, RP11-360D2.1, KATNBL1, EIF2B4, WI2-237311.2, POLB, FAM229B, RP11-326K13.4, FAM81B, PLCE1-AS2, BAZ2A, GNAI2, ZEB1, FAM83C, NDUFS8, DYNLL1, HMGB4, LMNTD2, C1orf43, LINC00943, RP1-266L20.2, SAMD4A, SNHG9, TLE4, CITED4, HDAC11, RP11-192H23.7, TMEM191C, TUBGCP4, PGP, PRM3, NDUFB6, RND2, WDR74, RP11-66602.2, PIN1, ZNRD1, TAF10, H3F3B, of and COX7C.

6. The method of claim 5, wherein said at least one additional gene comprises at least 5 additional genes selected from the group.

7. The method of claim 5, wherein said at least one additional gene comprises at least 100 additional genes selected from the group.

8. The method of claim 5, wherein said at least one additional gene comprises at least 200 additional genes selected from the group.

9. The method of claim 5, wherein said at least one additional gene comprises at least 300 additional genes selected from the group.

10. The method of claim 5, wherein the at least one additional gene is selected from the group consisting of BACE1-AS, UNC119B, RP11-338I21.1, MEIS1, WDR55, IL6R, RP11-62H20.1, RP11-356J5.12, RP1-251M9.2, DNAJB4, MALSU1, EFCAB14, C3, RAB35, DNAJB7, DYNLL2, TIGAR, SSUH2, TPCN1, AL157902.3, STK32C, MED30, CTD-2083E4.6, LHX2, RP11-567M16.6, PHKB, CAHM, RP11-17A4.2, SIPA1L1, TMEM260, CDC42BPA, EVX1-AS, RP11-242D8.1, CDIPT, RP11-991C1.2, AP006216.5, RP11-696N14.1, TRABD, AC074391.1, CLCN3, RP11-644K8.1, GABARAPL1, ATF3, RFPL3S, CTD-2196E14.5, RP11-49619.1, RP11-347D21.1, TRMT5, RP11-712B9.2, CSTL1, XXbac-BPG249D20.9, RP11-669C19.1, NRDE2, MAPT-AS1, EFCAB12, VGLL3, DCC, HSPB6, S100A7A, CTD-2135D7.2, KRT15, RP11-403A21.3, RP11-396C23.4, C10orf90, GMFG, KDM2B, TMSB4X, RP11-381K20.4, OR2H1, ZNF445, TEPP, CTC-543D15.8, CCDC155, MAPK3, RP5-1030M6.3, SORCS3-AS1, RP11-489E7.4, AC007163.3, XXyac-YX155B6.5, TP53TG5, C9orf3, APOL6, ARL4C, AC093627.10, SERPINB6, PIBF1, CDK19, RBBP6, RP11-140K17.3, EAF1, GLRX2, RP11-557J10.5, DAG1, RP11-96K19.5, WDR20, AC093818.1, NECAP2, RP11-375N15.2, DHDDS, LRRC52, WTIP, TNKS, CFAP157, COX8C, XPNPEP3, NOLC1, RARA-AS1, RP4-625H18.2, FANK1, PPP2R1B, RP11-168K9.1, ARL6IP4, AACS, RSRC2, and ZCCHC8.

11. The method of claim 5, wherein the at least one additional gene is selected from the group consisting of CTD-2363C16.1, KLHL12, CEP152, RP11-295M18.6, AC084219.4, HDAC4, DPP3, OVOS2, MAMDC2-AS1, FAM186A, ACSS1, CDIP1, INPP5B, PPP1R12B, RP11-527L4.6, ATP6VIA, EFCAB11, VN1R2, FAM179A, PELP1, STOML2, PCOLCE-AS1, AC004490.1, EVX2, RP11-258F1.1, CDKN1C, RP5-971N18.3, LAPTM4A, RP11-369E15.3, EIF5A2, PTPRD, RNF139-AS1, FAM71F1, CLK3, UGT1A6, C21orf91, DES, IBA57-AS1, HNRNPR, CCDC168, AC013436.6, ZNF32-AS3, LINC01095, MAPKAPK5-AS1, RP11-2F20.1, DGCR8, AC007563.1, UBE4A, AC004510.3, SYNCRIP, HSPH1, CTD-2206N4.2, LINC00919, RP11-17M16.2, ADGRG1, KRTCAP3, JARID2-AS1, CREB3L2, AC092168.3, RP11-493E12.1, SETD9, MRC2, AC008937.3, RP11-159D12.10, CCSER1, RP11-1018N14.1, FILIP1L, KIAA1217, RNFT2, NDUFA11, AC015971.2, CDH23, RP11-98D18.16, HNRNPH1, CTB-5506.13, P4HTM, SMIM6, TTLL1, UQCRB, AC097495.2, RP11-796E2.4, LYSMD2, MGAT4C, RP11-862G15.1, PFN3, FAM212B, RBM15B, RNF103, RP11-396F22.1, C10orf82, SYS1, RP11-404L6.2, DDX5, LINC00906, PSMD3, PPP1R3E, PTK7, LINC01487, MAP3K14-AS1, MRPL9, ZFYVE28, KRTDAP, OSBP2, NUMBL, FKBP7, LMX1A, TXNDC2, ZCCHC8, RP11-666A8.9, RP5-1051H14.2, NRBP1, FAM170B-AS1, RP11-439E19.9, RPL37, MGST3, CTD-2020K17.4, SCRT1, RP11-173A6.3, FBXO34, MRFAP1, TRIM11, PCBP4, RANBP2, FAM229A, EQTN, GOLGA6L10, AC116609.1, MTPAP, GSTO1, PACS2, CTD-3035K23.7, RP11-73K9.2, FAM153A, CCDC80, ACTL7B, CFL1, RP11-1010.1, GTSF1L, AC007557.4, SPIRE1, MRPS7, EAF1-AS1, RP11-545G3.1, IQCF3, CLIC5, SLC37A1, RP11-394A14.2, MYH7B, FKBP3, MINOS1, CENPJ, CFAP44, BRD2, RP11-684B21.1, AGAP1, FARP2, MIR7515HG, RP11-544A12.8, KMO, FAM209A, TMEM160, TAF5L, PSMA4, LINC01198, LDLRAD4, LINC00442, HYAL1, ATPAF1, C20orf144, ARF4-AS1, APOPT1, DNAAF3, EIF5A, NFIB, HPCA, CSPP1, IPO5, RP11-360D2.1, KATNBL1, EIF2B4, WI2-237311.2, POLB, FAM229B, RP11-326K13.4, FAM81B, PLCE1-AS2, BAZ2A, GNAI2, ZEB1, FAM83C, NDUFS8, DYNLL1, HMGB4, LMNTD2, C1orf43, LINC00943, RP1-266L20.2, SAMD4A, SNHG9, TLE4, CITED4, HDAC11, RP11-192H23.7, TMEM191C, TUBGCP4, PGP, PRM3, NDUFB6, RND2, WDR74, RP11-66602.2, PIN1, ZNRD1, TAF10, H3F3B, and COX7C.

12. The method of claim 1, wherein the gene expression profile further comprises at least one additional gene selected from the group consisting of BACE1-AS, UNC119B, RP11-338I21.1, TIGAR, TPCN1, RP11-567M16.6, CAHM, EVX1-AS, CDIPT, RP11-991C1.2, CLCN3, GABARAPL1, ATF3, CTD-2196E14.5, CSTL1, EFCAB12, VGLL3, HSPB6, TMSB4X, KDM2B, SORCS3-AS1, RP11-140K17.3, GLRX2, DAG1, WDR20, DHDDS, LRRC52, and MEX3D.

13. The method of claim 1, further comprising, prior to the step of utilizing the sperm sample for in vitro fertilization, generating an additional gene expression profile based on the constructed single cell RNA-Seq libraries, direct RNA measurement libraries, or cDNA libraries, wherein the additional gene expression profile comprises at least one gene selected from the group consisting of PHOSPHO1, ETNK2, C17orf74, DGCR6L, ODF3L2, CIB1, NUPR2, C16orf82, UBXN6, DNAJC4, UBA52, REEP6, LELP1, RANGAP1, TNFAIP8L1, ARL4A, PRM2, TPGS2, CSNK1G2, LPIN1, ZNHIT2, PCSK4, PCYT2, OAZ3, TPPP2, SMCP, FBXW5, TCP11, BOD1L2, CARHSP1, GLUL, C2orf57, SMKR1, PTP4A1, CCSER2, AQP5, MPC2, RGS22, PKM, MOSPD3, CCDC136, AC012370.3, VTI1B, INCA1, SPAT-CIL, CXCL16, METAP1, USP25, SH3GL3, MAP2K2, CRAT, RPS27A, RPL29, RPL13, ANKRD12, TUBB4B, NRAV, FAM220A, FXR1, BSG, TSPAN6, RPL12, PWRN1, SRP54, CCNY, PVRL3, BPIFA3, PTOV1, ADO, NSUN4, SRPK2, RIOK3, SPCS1, GPR137, UBE2N, RPL8, WASFI, FUNDC2, HDLBP, SPTBN2, SLFNL1, GSG1, NT5C1B, PPP2R5A, PHKG2, PROCA1, INPP5K, PDZD8, ABHD1, SLAIN2, SPATA3, TSSK6, UBE2D2, PRC1-AS1, VWA3B, HSPA4L, FKBP8, MFF, LINC00901, GNAS, RNF138, CABYR, TSSKIB, TSSK2, SPATA18, RPS18, SLC38A7, TPD52L3, ACSBG2, RP11-14J7.7, RPLP1, TPP2, PSMD6, PAFAH1B1, UBA5, RPL37A, GAPDH, RPS8, C17orf97, CCDC91, SEC14L1, MTFRIL, DCU-NID1, RABIA, CRISP2, RPS6, PGK2, VRK3, BAZIA, TPT1, AKAP1, MS4A14, CCDC7, SEMG1, SARAF, RPL13A, FTH1, CUL3, POLRID, MT-CO2, FSCB, RPS4X, CLU, RPL3, PLBD2, RPL10, C3orf22, CLPB, NDUFA13, MYL6B, AURKAIP1, TMBIM6, GKAP1, CEP85L, DUSP15, TMEM38B, RP11-109E10.1, RNF139, ZMIZ2, CIB2, GDPD5, RCOR3, PPMIG, C7orf73, ZNF706, SNX13, DZIP1, HBP1, ZNF571-AS1, CPTP, C9orf173, BAG5, IZUMO4, C6orf120, MFAP3L, ZC3H15, LRRD1, ENO1, C9orf16, NAT6, BRK1, POLD2, SORBS3, RPL23A, AGPAT2, SMPD2, DMWD, ODC1, PCGF5, AC007325.4, CCDC37-AS1, PEX10, ACTL10, PAOX, ACTL7A, KDM5B, C11orf68, USP2, TMEM120A, EIF4E, EPN1, TCP1, UBACI, TTC7A, C10orf62, RUVBL2, MAD2L2, AP2B1, MAATS1, RAD23B, PPP2R2B, ST13, KLHDC3, EEF1D, PTDSS2, SLC5A2, TP53111, SLC2A8, C12orf50, RPL36, STARD10, TBC1D10B, CDHR2, ACE, ITPKA, DGCR14, RNF38, UBQLN3, DDX20, CCDC169, PARP6, PODXL2, RAB11FIP5, PDXK, PPDPF, FAM217A, GGN, GABRG3-AS1, RPS15, TPI1, AZIN2, RBCK1, DPP7, MLF1, ELOF1, PDXDC1, KTN1, ICA1, OPLAH, BZW1, RAD21, SPZ1, RTN4, CDIPT-AS1, SHARPIN, ZFAND3, ARF1, FNDC8, TOLLIP, MIS12, ATAD1, MEIOC, RP11-2C24.7, CCDC187, CTSF, SPPL2B, TTLL10, HAGLR, CCHCR1, CYB5R4, FBXL13, CCDC7.1, RPS9, CABS1, RNF11, FAM104A, EIF5, DYRKIB, ZMYM2, C21orf2, DDX3Y, C1orf159, DNAJC18, ZDHHC3, IL13, GINM1, CDV3, ZFAND4, C12orf75, CCPG1, STK35, AF131216.1, FAM76B, FAM234A, PSMF1, TEX38, GTSF1, VPRBP, RNF32, LCA5L, RPL41, CYB5R2, MROH7, TSPAN16, LRTOMT, AHCY, EGLN2, AC012594.1, USPL1, DDX3X, ITCH, WBP2NL, RPL19, CAMLG, NBR1, ARHGAP5, RAB3IP, IGSF11-AS1, SERF2, C6orf201, COL9A3, BRWD1-AS2, CENPU, TMEM215, STT3B, DHX57, RMND5B, SKP1, SLC25A39, CFAP221, PHACTR2-AS1, ZDHHC19, RPL15, ISG20L2, ESPN, PRKCZ, COPS5, TSPAN1, ZNF688, RP11-73G16.3, DCAF10, C17orf50, and YPEL5 and determining that none of the genes in the additional gene expression profile are downregulated compared to the level of expression of the respective same gene in a healthy control sperm sample.

14. The method of claim 13, wherein said at least one additional gene comprises at least 50 genes selected from the group.

15. The method of claim 13, wherein said at least one additional gene comprises at least 100 genes selected from the group.

16. The method of claim 13, wherein said at least one additional gene comprises at least 200 genes selected from the group.

17. The method of claim 13, wherein said at least one additional gene comprises at least 300 genes selected from the group.

18. The method of claim 13, wherein said at least one gene in the additional gene expression profile is selected from the group consisting of PHOSPHO1, ETNK2, C17orf74, DGCR6L, ODF3L2, CIB1, NUPR2, C16orf82, UBXN6, DNAJC4, UBA52, REEP6, LELP1, RANGAP1, TNFAIP8L1, ARL4A, PRM2, TPGS2, CSNK1G2, LPIN1, ZNHIT2, PCSK4, PCYT2, OAZ3, TPPP2, SMCP, FBXW5, TCP11, BODIL2, CARHSP1, GLUL, C2orf57, SMKR1, PTP4A1, CCSER2, AQP5, MPC2, RGS22, PKM, and MOSPD3.

19. The method of claim 1, further comprising, prior to the step of utilizing the sperm sample for in vitro fertilization, generating an additional gene expression profile based on the constructed single cell RNA-Seq libraries, direct RNA measurement libraries, or cDNA libraries, wherein the additional gene expression profile comprises at least one gene selected from the group consisting of CCDC136, AC012370.3, VTIIB, INCA1, SPATCIL, CXCL16, METAP1, USP25, SH3GL3, MAP2K2, CRAT, RPS27A, RPL29, RPL13, ANKRD12, TUBB4B, NRAV, FAM220A, FXR1, BSG, TSPAN6, RPL12, PWRN1, SRP54, CCNY, PVRL3, BPIFA3, PTOV1, ADO, NSUN4, SRPK2, RIOK3, SPCS1, GPR137, UBE2N, RPL8, WASF1, FUNDC2, HDLBP, SPTBN2, SLFNL1, GSG1, NT5C1B, PPP2R5A, PHKG2, PROCA1, INPP5K, PDZD8, ABHD1, SLAIN2, SPATA3, TSSK6, UBE2D2, PRC1-AS1, VWA3B, HSPA4L, FKBP8, MFF, LINC00901, GNAS, RNF138, CABYR, TSSKIB, TSSK2, SPATA18, RPS18, SLC38A7, TPD52L3, ACSBG2, RP11-14J7.7, RPLP1, TPP2, PSMD6, PAFAH1B1, UBA5, RPL37A, GAPDH, RPS8, C17orf97, CCDC91, SEC14L1, MTFRIL, DCUNID1, RABIA, CRISP2, RPS6, PGK2, VRK3, BAZIA, TPT1, AKAP1, MS4A14, CCDC7, SEMG1, SARAF, RPL13A, FTH1, CUL3, POLR1D, MT-CO2, FSCB, RPS4X, CLU, RPL3, PLBD2, and RPL10, and determining that none of the genes in the additional gene expression profile are downregulated compared to the level of expression of the respective same gene in a healthy control sperm sample.

20. The method of claim 1, further comprising prior to the step of utilizing the sperm sample for in vitro fertilization, generating an additional gene expression profile based on the constructed single cell RNA-Seq libraries, direct RNA measurement libraries, or cDNA libraries, wherein the additional gene expression profile comprises at least one gene selected from the group consisting of C3orf22, CLPB, NDUFA13, MYL6B, AURKAIP1, TMBIM6, GKAP1, CEP85L, DUSP15, TMEM38B, RP11-109E10.1, RNF139, ZMIZ2, CIB2, GDPD5, RCOR3, PPMIG, C7orf73, ZNF706, SNX13, DZIP1, HBP1, ZNF571-AS1, CPTP, C9orf173, BAG5, IZUMO4, C6orf120, MFAP3L, ZC3H15, LRRD1, ENO1, C9orf16, NAT6, BRK1, POLD2, SORBS3, RPL23A, AGPAT2, SMPD2, DMWD, ODC1, PCGF5, AC007325.4, CCDC37-AS1, PEX10, ACTL10, PAOX, ACTL7A, KDM5B, C11orf68, USP2, TMEM120A, EIF4E, EPN1, TCP1, UBACI, TTC7A, C10orf62, RUVBL2, MAD2L2, AP2B1, MAATS1, RAD23B, PPP2R2B, ST13, KLHDC3, EEF1D, PTDSS2, SLC5A2, TP53I11, SLC2A8, C12orf50, RPL36, STARD10, TBC1D10B, CDHR2, ACE, ITPKA, DGCR14, RNF38, UBQLN3, DDX20, CCDC169, PARP6, PODXL2, RAB11FIP5, PDXK, PPDPF, FAM217A, GGN, GABRG3-AS1, RPS15, TPI1, AZIN2, RBCK1, DPP7, MLF1, ELOF1, PDXDC1, KTN1, ICA1, OPLAH, BZW1, RAD21, SPZ1, RTN4, CDIPT-AS1, SHARPIN, ZFAND3, ARF1, FNDC8, TOLLIP, MIS12, ATAD1, MEIOC, RP11-2C24.7, CCDC187, CTSF, SPPL2B, TTLL10, HAGLR, CCHCR1, CYB5R4, FBXL13, CCDC7.1, RPS9, CABS1, RNF11, FAM104A, EIF5, DYRK1B, ZMYM2, C21orf2, DDX3Y, C1orf159, DNAJC18, ZDHHC3, IL13, GINM1, CDV3, ZFAND4, C12orf75, CCPG1, STK35, AF131216.1, FAM76B, FAM234A, PSMF1, TEX38, GTSF1, VPRBP, RNF32, LCA5L, RPL41, CYB5R2, MROH7, TSPAN16, LRTOMT, AHCY, EGLN2, AC012594.1, USPL1, DDX3X, ITCH, WBP2NL, RPL19, CAMLG, NBR1, ARHGAP5, RAB3IP, IGSF11-AS1, SERF2, C6orf201, COL9A3, BRWD1-AS2, CENPU, TMEM215, STT3B, DHX57, RMND5B, SKP1, SLC25A39, CFAP221, PHACTR2-AS1, ZDHHC19, RPL15, ISG20L2, ESPN, PRKCZ, COPS5, TSPAN1, ZNF688, RP11-73G16.3, DCAF10, C17orf50, and YPEL5, and determining that none of the genes in the additional gene expression profile are downregulated compared to the level of expression of the respective same gene in a healthy control sperm sample.

21. The method of claim 1, further comprising, prior to the step of utilizing the sperm sample for in vitro fertilization, determining that the ratio of PRM2/PRM1 is not less than 1.5.

* * * * *